US007001995B1

(12) United States Patent
Neeper et al.

(10) Patent No.: US 7,001,995 B1
(45) Date of Patent: Feb. 21, 2006

(54) SYNTHETIC HUMAN PAPILLOMAVIRUS GENES

(75) Inventors: Michael P Neeper, Collegeville, PA (US); William L. McClements, Doylestown, PA (US); Kathrin U. Jansen, Doylestown, PA (US); Loren D. Schultz, Harleysville, PA (US); Ling Chen, Blue Bell, PA (US); Xin-Min Wang, Schwenksville, PA (US)

(73) Assignee: Merck & Co., Inc., Rahway, NJ (US)

( * ) Notice: Subject to any disclaimer, the term of this patent is extended or adjusted under 35 U.S.C. 154(b) by 593 days.

(21) Appl. No.: 09/642,405

(22) Filed: Aug. 21, 2000

Related U.S. Application Data

(60) Provisional application No. 60/210,143, filed on Jun. 7, 2000, provisional application No. 60/150,728, filed on Aug. 25, 1999.

(51) Int. Cl.
*C07H 21/04* (2006.01)
*C12N 15/74* (2006.01)
*A61K 48/00* (2006.01)
*C12P 21/06* (2006.01)

(52) U.S. Cl. ................. 536/23.1; 435/320.1; 435/69.1; 424/93.21; 514/44

(58) Field of Classification Search .................. 514/44; 536/23.1; 435/320.1, 69.1; 424/93.21
See application file for complete search history.

(56) References Cited

U.S. PATENT DOCUMENTS

| | | | | |
|---|---|---|---|---|
| 5,679,509 A | | 10/1997 | Wheeler et al. | |
| 5,820,870 A | * | 10/1998 | Joyce et al. | |
| 5,874,304 A | * | 2/1999 | Zolotukhin et al. | 435/366 |
| 5,952,216 A | * | 9/1999 | Ludmerer | 435/235.1 |
| 6,019,978 A | * | 2/2000 | Ertl et al. | |
| 6,123,948 A | * | 9/2000 | Whittle et al. | |
| 6,159,729 A | * | 12/2000 | Hofmann et al. | |
| 6,399,383 B1 | * | 6/2002 | Apt et al. | 435/456 |
| 6,489,141 B1 | * | 12/2002 | Frazer et al. | 435/69.1 |

FOREIGN PATENT DOCUMENTS

| | | | |
|---|---|---|---|
| WO | WO 96/00583 | | 11/1996 |
| WO | WO 96/39178 | | 12/1996 |
| WO | WO 9902694 A1 | * | 1/1999 |

OTHER PUBLICATIONS

Donnelly et al. Protection against papillomavirus with a polynuicleotide vaccine pp. 314-320 1996.*

Bodey et al. Failure of cancer vaccines. The significant limitations of this approach to immunotherapy pp. 2665-2676 2000.*

McCluskie et al. Route and method of delivery of DNA vaccine influence immune responses in mice and non-human primates 1999.*

Orkin et al. Report and recommendations of the panel to assess the NIH investment in research on gene therapy pp. 1-41 1995.*

Rudinger Characteristics of the amino acids as components of a peptide hormone sequence pp. 1-8 1976.*

Bowie et al. Deciphering the message in protein sequences: tolerance to amino acid substitutions vol. 247 1990.*

Chemical compound Mar. 8, 2001.*

Moingeon et al. Challenges and issues in new vaccine development pp. 173-175 vol. 23 No. 4 2002.*

Bubenik, J. Int. J. Oncol 2002;20:207.*

Nakano et al. J Virol 1997;71:7101-09.*

He, Z., et al. Viral Recombinant Vaccines to the E6 and E7 Antigens of HPV-16, VIROLOGY. 270. 146-161, 2000.

Toes, R. E. M., et al, Protective Anti-Tumor Immunity . . . in a String of Beads Fashion, Proc. Natl. Acad. Scie. USA, vol. 94. pp. 14660-14665. Dec. 1997.

Borysiewicz, L. K., et al., A Recombinant Vaccinia Encoding Human Papillomavirus Types 16 and 18, E6 and E7 Proteins as Immunotherapy for Cervical Cancer, The Lancet, vol. 347, p. 1523-1527, Jun. 1, 1996.

Nimako, M. et al., Human Papillomavirus-specific Cytotoxic T Lymphocytes in Patients with Cervical Intraepithelial Neoplasia Grade III. Cancer Research, vol. 57, p. 4855-4861, Nov. 1, 1997.

Smahel, M., et al., DNA Vaccine Against Oncogenic Hamster Cells . . . Activated ras Oncogene, Oncology Reports vol. 6. p. 211-215, 1999.

Xu, Jianqing et al. Human Papillomavirus 16 7-specific CTL Induction through Mouse B7-1 Costiumulating with E7C Subgene Chin J. Microbiol Immunol. vol. 19, No. 3, p 227-231.

Kotecha, M. T., et al., Humoral Response Induced by Vaccination with Plasmid DNA Containing the HPV16 LI ORF IMMUNOLOGY vol. 95, No. Suppl. 1, p. 107, 1998.

Afghan, R.K., et al., Immune Responses Induced by Vaccination With Plasmid DNA Containing The HPV16 E7 ORF IMMUNOLOGY vol. 95, No. Suppl. 1, p. 106, 1998.

Zhou, Jian et al., Papillomavirus Capsid Protein Expression . . . and tRNA Availability, Jour of Virology, vol. 73, No. 6, p. 4972-4982, Jun. 1999.

(Continued)

*Primary Examiner*—Q. Janice Li
(74) *Attorney, Agent, or Firm*—Alysia A. Finnegan; Joanne M. Giesser

(57) ABSTRACT

Synthetic DNA molecules encoding papillomavirus proteins are provided. The codons of the synthetic molecules are codons preferred by the projected host cell. The synthetic molecules may be used as a polynucleotide vaccine which provides effective immunoprophylaxis against papillomavirus infection through stimulation of neutralizing antibody and cell-mediated immunity.

15 Claims, 33 Drawing Sheets

OTHER PUBLICATIONS

Chen, C. H., et al. Boosting with Recombinant Vaccinia . . . expressing DNA Vaccines, VACCINE, vol. 18, p. 2015-2022, 2000.

Lathe, "Synthetic Oligonucleotide Probes Deduced from Amino Acid Sequence Data", J. Mol. Biol., vol. 183, pp. 1-12, 1985.

De Pasquale, et al., "Modulation of HPV16 E7 Translation by tRNAs in Eukaryotic Cell-Free Translation Systems", Biochemistry and Molecular Biology International, vol. 45, No. 5, pp. 1005-1009, Aug. 1998.

Pasquala et al; vol. No. 5, 1998 Biochemistry and Molecular Biology International, pp. 1005-1009.

* cited by examiner

FIGURE 1

SEQ.ID.NO:1 Sequence of the Codon-Optimized HPV16 L1

ATGAGCCTGTGGCTGCCCAGCGAGGCCACCGTGTACCTGCCTCCCGTGCCCG
TGAGCAAGGTGGTGAGCACCGACGAGTACGTGGCCCGCACCAACATCTACTA
CCACGCCGGCACCAGCCGCCTGCTGGCCGTGGGCCACCCCTACTTCCCCATC
AAGAAGCCCAACAACAACAAGATCCTGGTGCCCAAGGTGAGCGGCCTGCAG
TACCGCGTGTTCCGCATCCACCTGCCCGACCCCAACAAGTTCGGCTTCCCCGA
CACAAGCTTCTACAACCCCGACACCCAGCGCCTGGTGTGGGCCTGCGTGGGC
GTGGAGGTGGGCCGCGGCCAGCCCCTGGGCGTGGGCATCAGCGGCCACCCCC
TGCTGAACAAGCTGGACGACACCGAGAACGCCAGCGCCTACGCCGCCAACGC
CGGCGTGGACAACCGCGAGTGCATCAGCATGGACTACAAGCAGACCCAGCTG
TGCCTGATCGGCTGCAAGCCTCCCATCGGCGAGCACTGGGGCAAGGGCAGCC
CCTGCACCAACGTGGCCGTGAACCCCGGCGACTGCCCTCCCCTGGAGCTGAT
CAACACCGTGATCCAGGACGGCGACATGGTGGACACCGGCTTCGGCGCCATG
GACTTCACCACCCTGCAGGCCAACAAGAGCGAGGTGCCCCTGGACATCTGCA
CCAGCATCTGCAAGTACCCCGACTACATCAAGATGGTGAGCGAGCCCTACGG
CGACAGCCTGTTCTTCTACCTGCGCCGCGAGCAGATGTTCGTGCGCCACCTGT
TCAACCGCGCCGGCGCCGTGGGCGAGAACGTGCCCGACGACCTGTACATCAA
GGGCAGCGGCAGCACCGCCAACCTGGCCAGCAGCAACTACTTCCCCACTCCC
AGCGGCAGCATGGTGACCAGCGACGCCCAAATCTTCAACAAGCCCTACTGGC
TGCAGCGCGCCCAGGGCCACAACAACGGCATCTGCTGGGGCAACCAGCTGTT
CGTGACCGTGGTGGACACCACCCGCAGCACCAACATGAGCCTGTGCGCCGCC
ATCAGCACCAGCGAGACCACCTACAAGAACACCAACTTCAAGGAGTACCTGC
GCCACGGCGAGGAGTACGACCTGCAGTTCATCTTCCAGCTGTGCAAGATCAC
CCTGACCGCCGACGTGATGACCTACATCCACAGCATGAACAGCACCATCCTG
GAGGACTGGAACTTCGGCCTGCAGCCCCCTCCCGGCGGTACCCTGGAGGACA
CCTACCGCTTCGTGACCAGCCAGGCCATCGCCTGCCAGAAGCACACCCCTCC
CGCTCCCAAGGAGGATCCCCTGAAGAAGTACACCTTCTGGGAGGTGAACCTG
AAGGAGAAGTTCAGCGCCGACCTGGACCAGTTCCCCCTGGGCCGCAAGTTCC
TGCTGCAGGCCGGCCTGAAGGCCAAGCCCAAGTTCACCCTGGGCAAGCGCAA
GGCCACCCCCACCACCAGCAGCACCAGCACCACCGCCAAGCGCAAGAAGCG
CAAGCTGTAA

FIGURE 2

SEQ.ID.NO:2 Codon-Optimized HPV16 E1-G482D,W439R Mutant:

ATGGCCGACCCCGCCGGCACCAACGGCGAGGAGGGCACCGGCTGCAACGGC
TGGTTCTACGTGGAGGCCGTGGTGGAGAAGAAGACCGGCGACGCCATCAGCG
ACGACGAGAACGAGAACGACAGCGACACCGGCGAGGACCTGGTGGACTTCA
TCGTGAACGACAACGACTACCTGACCCAGGCCGAGACCGAGACCGCCCACGC
CCTGTTCACCGCCCAGGAGGCCAAGCAGCACCGCGACGCCGTGCAGGTGCTG
AAGCGCAAGTACCTGGGCAGCCCCCTGAGCGACATCAGCGGCTGCGTCGACA
ACAACATCAGCCCCCGCCTGAAGGCCATCTGCATCGAGAAGCAGAGCCGCGC
CGCCAAGCGCCGCCTGTTCGAGAGCGAGGACAGCGGCTACGGCAACACCGA
GGTGGAGACCCAGCAGATGCTGCAGGTGGAGGGCCGCCACGAGACCGAGAC
CCCCTGCAGCCAGTACAGCGGCGGCAGCGGCGGCGGCTGCAGCCAGTACAGC
AGCGGCAGCGGCGGCGAGGGCGTGAGCGAGCGCCACACCATCTGCCAGACC
CCTCTGACCAACATCCTGAACGTGCTGAAGACCAGCAACGCCAAGGCCGCCA
TGCTGGCCAAGTTCAAGGAGCTGTACGGCGTGAGCTTCAGCGAGCTGGTGCG
CCCCTTCAAGAGCAACAAGAGCACCTGCTGCGACTGGTGCATCGCCGCCTTC
GGCCTGACCCCCAGCATCGCCGACAGCATCAAGACCCTGCTGCAGCAGTACT
GCCTGTACCTGCACATCCAGAGCCTGGCCTGCAGCTGGGGCATGGTGGTGCT
GCTGCTGGTGCGCTACAAGTGCGGCAAGAACCGCGAGACCATCGAGAAGCTG
CTGAGCAAGCTGCTGTGCGTGAGCCCCATGTGCATGATGATCGAGCCTCCCA
AGCTTCGCAGCACCGCCGCCGCCCTGTACTGGTACAAGACCGGCATCAGCAA
CATCAGCGAGGTGTACGGCGACACCCCCGAGTGGATCCAGCGCCAGACCGTG
CTGCAGCACAGCTTCAACGACTGCACCTTCGAGCTGAGCCAGATGGTGCAGT
GGGCCTACGACAACGACATCGTGGACGACAGCGAGATCGCCTACAAGTACGC
CCAGCTGGCCGACACCAACAGCAACGCCAGCGCCTTCCTGAAGAGCAACAGC
CAGGCCAAGATCGTGAAGGACTGCGCCACCATGTGCCGCCACTACAAGCGCG
CCGAGAAGAAGCAGATGAGCATGAGCCAGTGGATCAAGTACCGCTGCGACC
GCGTGGACGACGGCGGCGACCGCAAGCAGATCGTGATGTTCCTGCGCTACCA
GGGCGTGGAATTCATGAGCTTCCTGACCGCCCTGAAGCGCTTCCTGCAGGGC
ATCCCCAAGAAGAACTGCATCCTGCTGTACGGCGCCGCCAACACCGACAAGA
GCCTGTTCGGCATGAGCCTGATGAAGTTCCTGCAGGGCAGCGTGATCTGCTTC
GTGAACAGCAAGAGCCACTTCTGGCTGCAGCCCCTGGCCGACGCCAAGATCG
GCATGCTGGACGACGCCACCGTGCCCTGCTGGAACTACATCGACGACAACCT
GCGCAACGCCCTGGACGGCAACCTGGTGAGCATGGACGTGAAGCACCGCCCC
CTGGTGCAGCTGAAGTGCCCTCCCCTGCTGATCACCAGCAACATCAACGCCG
GCACCGACAGCCGCTGGCCCTACCTGCACAACCGCCTGGTGGTGTTCACCTTC
CCCAACGAGTTCCCCTTCGACGAGAACGGTAACCCCGTGTACGAGCTGAACG
ACAAGAACTGGAAGAGCTTCTTCAGCCGCACCTGGAGCCGCCTGAGCCTGCA
CGAGGACGAGGACAAGGAGAACGACGGCGACAGCCTGCCCACCTTCAAGTG
CGTGAGCGGCCAGAACACCAACACCCTGTAA

FIGURE 3

SEQ.ID.NO.:3 Sequence of the Codon-Optimized HPV16E2-E39A,I73A Mutant:

ATGGAGACCCTGTGCCAGCGCCTGAACGTGTGCCAGGACAAGATCCTGACCC
ACTACGAGAACGACAGCACCGACCTGCGCGACCACATCGACTACTGGAAGCA
CATGCGCCTGGCCTGCGCCATCTACTACAAGGCCCGCGAGATGGGCTTCAAG
CACATCAACCACCAGGTGGTGCCCACCCTGGCCGTGAGCAAGAACAAGGCCC
TGCAGGCCGCCGAGCTGCAGCTGACCCTGGAGACCATCTACAACAGCCAGTA
CAGCAACGAGAAGTGGACCCTGCAGGACGTGAGCCTGGAGGTGTACCTGACC
GCCCCCACCGGCTGCATCAAGAAGCACGGCTACACCGTGGAGGTGCAGTTCG
ACGGCGACATCTGCAACACCATGCACTACACCAACTGGACCCACATCTACAT
CTGCGAGGAGGCCAGCGTGACCGTGGTGGAGGGCCAGGTGGACTACTACGG
CCTGTACTACGTGCACGAGGGCATCCGCACCTACTTCGTGCAGTTCAAGGAC
GACGCCGAGAAGTACAGCAAGAACAAGGTGTGGGAGGTGCACGCCGGCGGC
CAGGTGATCCTGTGCCCCACCAGCGTGTTCAGCAGCAACGAGGTGAGCAGCC
CCGAGACCATCCGCCAGCACCTGGCCAACCACAGCGCCGCCACCCACACCAA
GGCCGTGGCCCTGGGCACCGAGGAGACCCAGACCACCATCCAGCGCCCCCGC
AGCGAGCCCGACACCGGCAACCCCTGCCACACCACCAAGCTGCTGCACCGCG
ACAGCGTGGACAGCGCCCCCATCCTGACCGCCTTCAACAGCAGCCACAAGGG
CCGCATCAACTGCAACAGCAACACCACCCCCATCGTGCACCTGAAGGGCGAC
GCCAACACCCTGAAGTGCCTGCGCTACCGCTTCAAGAAGCACTGCAAGCTGT
ACACCGCCGTGAGCAGCACCTGGCACTGGACCGGCCACAACGTGAAGCACA
AGAGCGCCATCGTGACCCTGACCTACGACAGCGAGTGGCAGCGCGACCAGTT
CCTGAGCCAGGTGAAGATCCCCAAGACCATCACCGTGAGCACCGGCTTCATG
AGCATCTAA

FIGURE 4

SEQ.ID.NO.:4 Codon-Optimized HPV16E7-C24G,E26G Mutant:

ATGCACGGCGACACCCCCACCCTGCACGAGTACATGCTGGACCTGCAGCCCG
AGACCACCGACCTGTACGGCTACGGCCAGCTGAACGACAGCAGCGAGGAGG
AGGACGAGATCGACGGCCCCGCCGGCCAGGCCGAGCCCGACCGCGCCCACT
ACAACATCGTGACCTTCTGCTGCAAGTGCGACAGCACCCTGCGCCTGTGCGT
GCAGAGCACCCACGTGGACATCCGCACCCTGGAGGACCTGCTGATGGGCACC
CTGGGCATCGTGTGCCCCATCTGCAGCCAGAAGCCCTAA

FIGURE 5

SEQ.ID.NO.:5 Codon-Optimized HPV6a E7 Gene:

ATGCACGGCCGCCACGTGACCCTGAAGGACATCGTGCTGGACCTGCAGCCTC
CCGACCCCGTGGGCCTGCACTGCTACGAGCAGCTGGTGGACAGCAGCGAGGA
CGAGGTGGACGAGGTGGACGGCCAGGACAGCCAGCCCCTGAAGCAGCACTT
CCAGATCGTGACCTGCTGCTGCGGCTGCGACAGCAACGTGCGCCTGGTGGTG
CAGTGCACCGAGACCGACATCCGCGAGGTGCAGCAGCTCCTGCTGGGTACCC
TGAACATCGTGTGCCCCATCTGCGCTCCCAAGACCTAA

FIGURE 6

SEQ.ID.NO.:6 Codon-Optimized HPV18 E7 Gene:

ATGCACGGCCCCAAGGCCACCCTGCAGGACATCGTGCTGCACCTGGAGCCCC
AGAACGAGATCCCCGTGGACCTGCTGTGCCACGAGCAGCTGAGCGACAGCGA
GGAGGAGAACGACGAGATCGACGGCGTGAACCACCAGCACCTGCCCGCTCG
CAGGGCCGAGCCCCAGCGCCACACCATGCTGTGCATGTGCTGCAAGTGCGAG
GCCCGCATCGAGCTGGTGGTGGAGAGCAGCGCTGACGACCTGCGCGCCTTCC
AGCAGCTGTTCCTGAACACCCTGAGCTTCGTGTGCCCCTGGTGCGCCAGCCAG
CAGTAA

FIGURE 7

SEQ.ID.NO.:7 Codon-Optimized HPV6a E2 Gene:

ATGGAGGCCATCGCCAAGCGCCTGGACGCCTGCCAGGAGCAGCTGCTGGAGC
TGTACGAGGAGAACAGCACCGACCTGCACAAGCACGTGCTGCACTGGAAGTG
CATGCGCCACGAGAGCGTGCTGCTGTACAAGGCCAAGCAGATGGGCCTGAGC
CACATCGGCATGCAGGTGGTGCCTCCTCTGAAGGTGAGCGAGGCCAAGGGCC
ACAACGCCATCGAGATGCAGATGCACCTCGAGAGCCTGCTGCGCACCGAGTA
CAGCATGGAGCCCTGGACCCTGCAGGAGACCAGCTACGAGATGTGGCAGACC
CCTCCCAAGCGCTGCTTCAAGAAGCGCGGCAAGACCGTGGAGGTGAAGTTCG
ACGGCTGCGCCAACAACACCATGGACTACGTGGTGTGGACCGACGTGTACGT
GCAGGACAACGACACCTGGGTGAAGGTGCACAGCATGGTGGACGCCAAGGG
CATCTACTACACCTGTGGCCAGTTCAAGACCTACTACGTGAACTTCGTGAAGG
AGGCCGAGAAGTACGGCAGCACCAAGCACTGGGAGGTGTGCTACGGCAGCA
CCGTGATCTGCAGCCCCGCTAGCGTGAGCAGCACCACCCAGGAGGTGAGCAT
CCCCGAGAGCACCACCTACACTCCCGCCCAGACCAGCACCCTGGTGAGCAGC
AGCACCAAGGAGGACGCCGTGCAGACCCCTCCTCGCAAGCGCGCCCGCGGC
GTGCAGCAGAGCCCCTGCAACGCCCTGTGCGTGGCCCACATCGGCCCCGTGG
ATAGCGGCAACCACAACCTGATCACCAACAACCACGACCAGCACCAGCGCC
GCAACAACAGCAACAGCAGCGCCACTCCCATCGTGCAGTTCCAGGGCGAGAG
CAACTGCCTGAAGTGCTTCCGCTACCGCCTGAACGATCGCCACCGCCACCTGT
TCGACCTGATCAGCAGCACCTGGCACTGGGCCAGCAGCAAGGCTCCCCACAA
GCACGCCATCGTGACCGTGACCTACGACAGCGAGGAGCAGCGCCAGCAGTTC
CTGGACGTGGTGAAGATCCCTCCCACCATCAGCCACAAGCTGGGCTTCATGA
GCCTGCACCTGCTGTAA

FIGURE 8

SEQ.ID.NO.:8 Codon-Optimized HPV18 E2 Gene:

ATGCAGACTCCCAAGGAGACCCTGAGCGAGCGCCTGAGCGCCCTGCAGGACA
AGATCATCGACCACTACGAGAACGACAGCAAGGACATCGACAGCCAGATCC
AGTACTGGCAGCTGATCCGCTGGGAGAACGCCATCTTCTTCGCCGCTCGCGA
GCACGGGATCCAGACCCTGAACCACCAGGTGGTGCCCGCCTACAACATCAGC
AAGAGCAAGGCCCACAAGGCCATCGAGCTGCAGATGGCCCTGCAGGGCCTG
GCCCAGAGCGCCTACAAGACCGAGGACTGGACCCTGCAGGACACCTGCGAG
GAGCTGTGGAACACCGAGCCCACCCACTGCTTCAAGAAGGGAGGCCAGACC
GTGCAGGTGTACTTCGACGGCAACAAGGACAACTGCATGAACTACGTGGCCT
GGGACAGCGTGTACTACATGACCGACGCCGGCACCTGGGACAAGACCGCCAC
CTGCGTGAGCCACCGCGGCCTGTACTACGTGAAGGAGGGCTACAACACCTTC
TACATCGAGTTCAAGAGCGAGTGCGAGAAGTACGGCAACACCGGCACCTGG
GAGGTGCACTTCGGCAACAACGTGATCGACTGCAACGACAGCATGTGCAGCA
CCAGCGACGACACCGTGAGCGCCACCCAGCTGGTGAAGCAGCTGCAGCACAC
TCCCAGCCCCTACAGCAGCACCGTGAGCGTGGGCACCGCCAAGACCTACGGC
CAGACCAGCGCCGCCACTCGCCCTGGCCACTGCGGCCTGGCCGAGAAGCAGC
ACTGCGGGCCCGTGAACCCTCTGCTGGGCGCCGCCACCGCCACCGGCAACAA
CAAGCGCCGCAAGCTGTGCAGCGGCAACACCACTCCCATCATCCACCTGAAG
GGCGACCGCAACAGCCTGAAGTGCCTGCGGTACCGCCTGCGCAAGCACAGCG
ACCACTACCGCGACATCAGCAGCACCTGGCACTGGACCGGCGCCGGGAACGA
GAAGACCGGCATCCTGACCGTGACCTACCACAGCGAGACCCAGCGCACCAAG
TTCCTGAACACCGTGGCCATCCCCGACAGCGTGCAGATCCTGGTGGGCTACA
TGACCATGTAA

Comparison of protein expression of native and synthetic HPV16 L1 genes a. mock
b. lacZ
c. synthetic 16 E2 isolate 6
d. synthetic 16 E2 isolate 11
e native 16 E2 xmw98.75 16557-27

Comparison of protein expression of native and synthetic HPV16 E7 genes a. mock
b. lacZ
c. synthetic HPV16 E7 isolate 2
d. synthetic HPV16 E7 isolate 4
e. native HPV16 E7 xmw98.75 16557-27

Expression of synthetic HPV 6 E2 gene

Expression of synthetic HPV 18 E2 gene

FIGURE 17

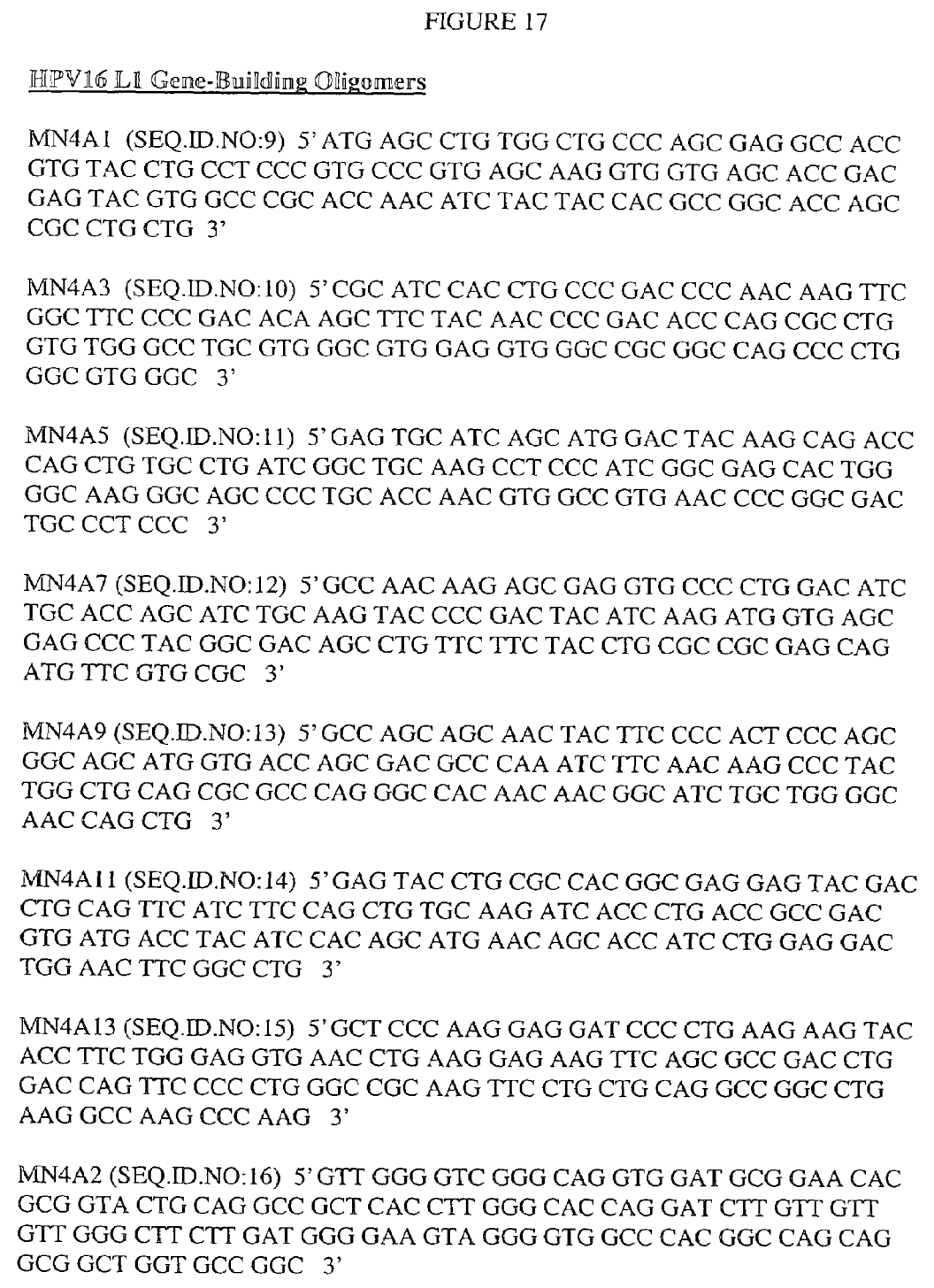

HPV16 L1 Gene-Building Oligomers

MN4A1 (SEQ.ID.NO:9) 5' ATG AGC CTG TGG CTG CCC AGC GAG GCC ACC GTG TAC CTG CCT CCC GTG CCC GTG AGC AAG GTG GTG AGC ACC GAC GAG TAC GTG GCC CGC ACC AAC ATC TAC TAC CAC GCC GGC ACC AGC CGC CTG CTG 3'

MN4A3 (SEQ.ID.NO:10) 5' CGC ATC CAC CTG CCC GAC CCC AAC AAG TTC GGC TTC CCC GAC ACA AGC TTC TAC AAC CCC GAC ACC CAG CGC CTG GTG TGG GCC TGC GTG GGC GTG GAG GTG GGC CGC GGC CAG CCC CTG GGC GTG GGC 3'

MN4A5 (SEQ.ID.NO:11) 5' GAG TGC ATC AGC ATG GAC TAC AAG CAG ACC CAG CTG TGC CTG ATC GGC TGC AAG CCT CCC ATC GGC GAG CAC TGG GGC AAG GGC AGC CCC TGC ACC AAC GTG GCC GTG AAC CCC GGC GAC TGC CCT CCC 3'

MN4A7 (SEQ.ID.NO:12) 5' GCC AAC AAG AGC GAG GTG CCC CTG GAC ATC TGC ACC AGC ATC TGC AAG TAC CCC GAC TAC ATC AAG ATG GTG AGC GAG CCC TAC GGC GAC AGC CTG TTC TTC TAC CTG CGC CGC GAG CAG ATG TTC GTG CGC 3'

MN4A9 (SEQ.ID.NO:13) 5' GCC AGC AGC AAC TAC TTC CCC ACT CCC AGC GGC AGC ATG GTG ACC AGC GAC GCC CAA ATC TTC AAC AAG CCC TAC TGG CTG CAG CGC GCC CAG GGC CAC AAC AAC GGC ATC TGC TGG GGC AAC CAG CTG 3'

MN4A11 (SEQ.ID.NO:14) 5' GAG TAC CTG CGC CAC GGC GAG GAG TAC GAC CTG CAG TTC ATC TTC CAG CTG TGC AAG ATC ACC CTG ACC GCC GAC GTG ATG ACC TAC ATC CAC AGC ATG AAC AGC ACC ATC CTG GAG GAC TGG AAC TTC GGC CTG 3'

MN4A13 (SEQ.ID.NO:15) 5' GCT CCC AAG GAG GAT CCC CTG AAG AAG TAC ACC TTC TGG GAG GTG AAC CTG AAG GAG AAG TTC AGC GCC GAC CTG GAC CAG TTC CCC CTG GGC CGC AAG TTC CTG CTG CAG GCC GGC CTG AAG GCC AAG CCC AAG 3'

MN4A2 (SEQ.ID.NO:16) 5' GTT GGG GTC GGG CAG GTG GAT GCG GAA CAC GCG GTA CTG CAG GCC GCT CAC CTT GGG CAC CAG GAT CTT GTT GTT GTT GGG CTT CTT GAT GGG GAA GTA GGG GTG GCC CAC GGC CAG CAG GCG GCT GGT GCC GGC 3'

Figure 17:
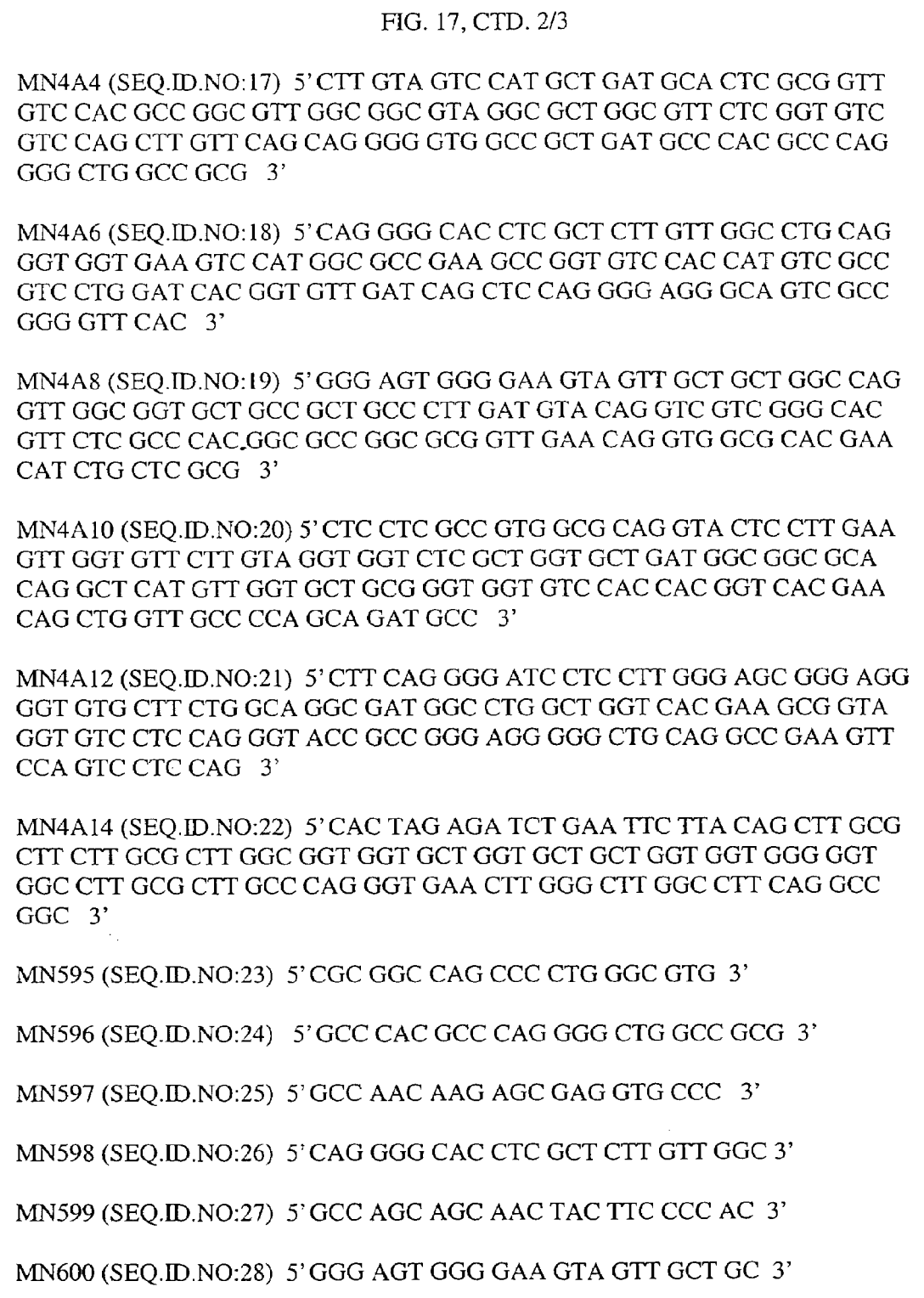

FIG. 17, CTD. 2/3

MN4A4 (SEQ.ID.NO:17) 5' CTT GTA GTC CAT GCT GAT GCA CTC GCG GTT GTC CAC GCC GGC GTT GGC GGC GTA GGC GCT GGC GTT CTC GGT GTC GTC CAG CTT GTT CAG CAG GGG GTG GCC GCT GAT GCC CAC GCC CAG GGG CTG GCC GCG 3'

MN4A6 (SEQ.ID.NO:18) 5' CAG GGG CAC CTC GCT CTT GTT GGC CTG CAG GGT GGT GAA GTC CAT GGC GCC GAA GCC GGT GTC CAC CAT GTC GCC GTC CTG GAT CAC GGT GTT GAT CAG CTC CAG GGG AGG GCA GTC GCC GGG GTT CAC 3'

MN4A8 (SEQ.ID.NO:19) 5' GGG AGT GGG GAA GTA GTT GCT GCT GGC CAG GTT GGC GGT GCT GCC GCT GCC CTT GAT GTA CAG GTC GTC GGG CAC GTT CTC GCC CAC GGC GCC GGC GCG GTT GAA CAG GTG GCG CAC GAA CAT CTG CTC GCG 3'

MN4A10 (SEQ.ID.NO:20) 5' CTC CTC GCC GTG GCG CAG GTA CTC CTT GAA GTT GGT GTT CTT GTA GGT GGT CTC GCT GGT GCT GAT GGC GGC GCA CAG GCT CAT GTT GGT GCT GCG GGT GGT GTC CAC CAC GGT CAC GAA CAG CTG GTT GCC CCA GCA GAT GCC 3'

MN4A12 (SEQ.ID.NO:21) 5' CTT CAG GGG ATC CTC CTT GGG AGC GGG AGG GGT GTG CTT CTG GCA GGC GAT GGC CTG GCT GGT CAC GAA GCG GTA GGT GTC CTC CAG GGT ACC GCC GGG AGG GGG CTG CAG GCC GAA GTT CCA GTC CTC CAG 3'

MN4A14 (SEQ.ID.NO:22) 5' CAC TAG AGA TCT GAA TTC TTA CAG CTT GCG CTT CTT GCG CTT GGC GGT GGT GCT GGT GCT GCT GGT GGT GGG GGT GGC CTT GCG CTT GCC CAG GGT GAA CTT GGG CTT GGC CTT CAG GCC GGC 3'

MN595 (SEQ.ID.NO:23) 5' CGC GGC CAG CCC CTG GGC GTG 3'

MN596 (SEQ.ID.NO:24) 5' GCC CAC GCC CAG GGG CTG GCC GCG 3'

MN597 (SEQ.ID.NO:25) 5' GCC AAC AAG AGC GAG GTG CCC 3'

MN598 (SEQ.ID.NO:26) 5' CAG GGG CAC CTC GCT CTT GTT GGC 3'

MN599 (SEQ.ID.NO:27) 5' GCC AGC AGC AAC TAC TTC CCC AC 3'

MN600 (SEQ.ID.NO:28) 5' GGG AGT GGG GAA GTA GTT GCT GC 3'

Figure 17:
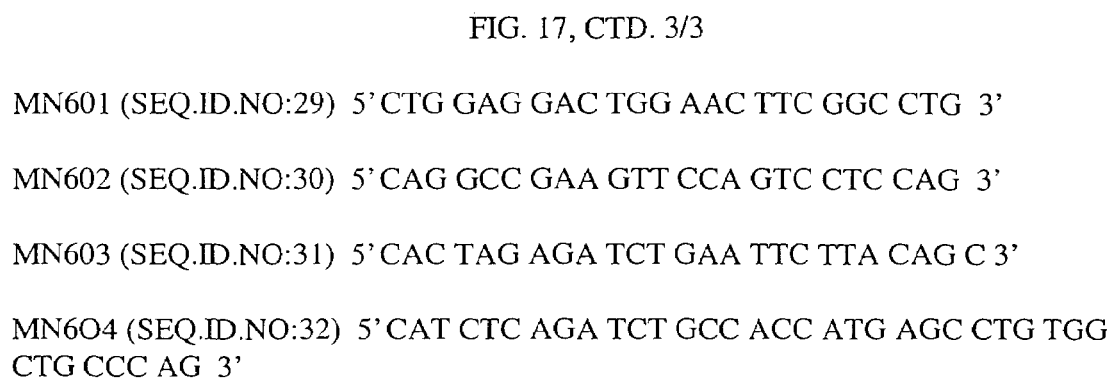

FIG. 17, CTD. 3/3

MN601 (SEQ.ID.NO:29) 5' CTG GAG GAC TGG AAC TTC GGC CTG 3'

MN602 (SEQ.ID.NO:30) 5' CAG GCC GAA GTT CCA GTC CTC CAG 3'

MN603 (SEQ.ID.NO:31) 5' CAC TAG AGA TCT GAA TTC TTA CAG C 3'

MN6O4 (SEQ.ID.NO:32) 5' CAT CTC AGA TCT GCC ACC ATG AGC CTG TGG CTG CCC AG 3'

FIGURE 18

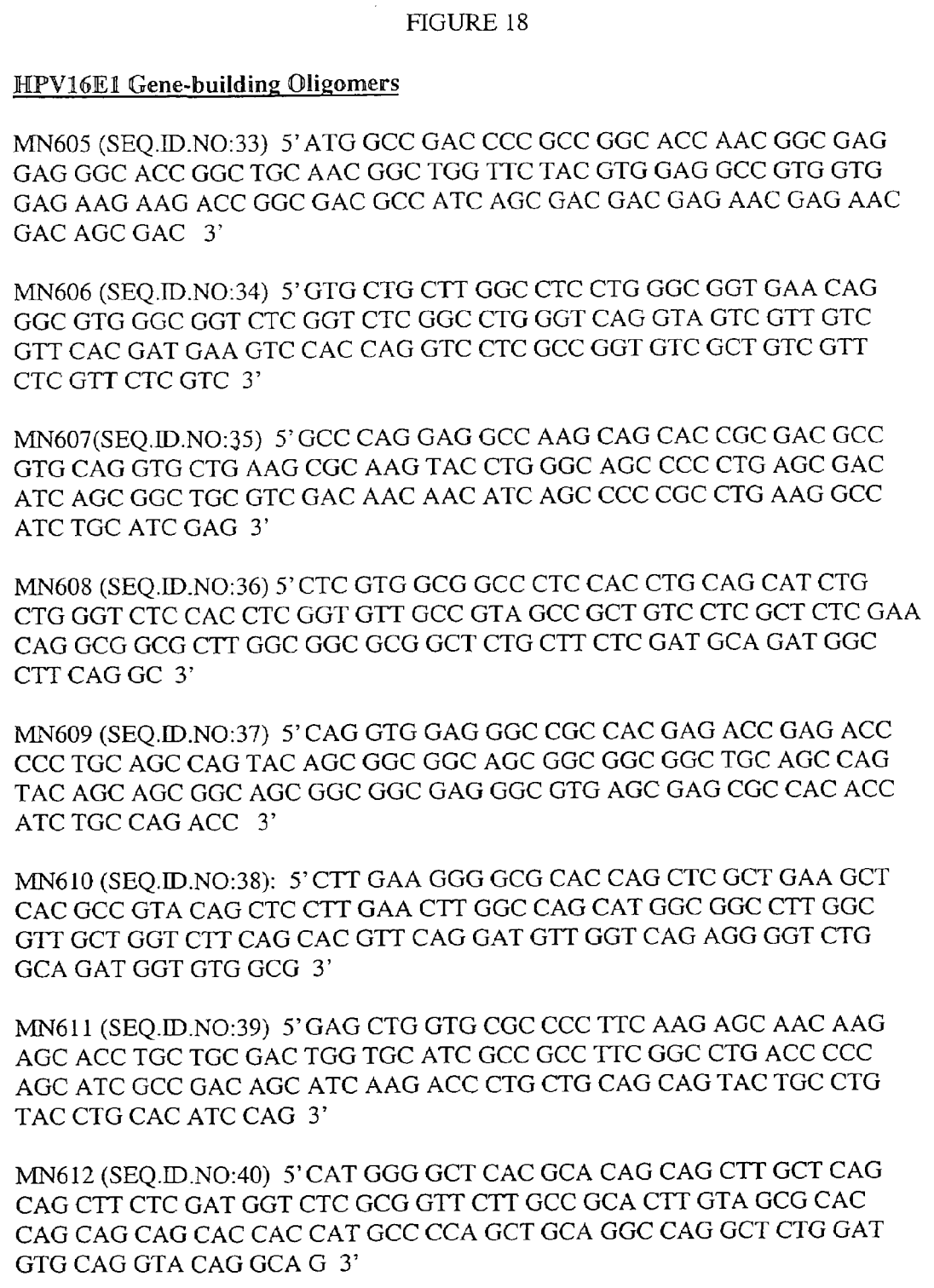

HPV16E1 Gene-building Oligomers

MN605 (SEQ.ID.NO:33) 5' ATG GCC GAC CCC GCC GGC ACC AAC GGC GAG GAG GGC ACC GGC TGC AAC GGC TGG TTC TAC GTG GAG GCC GTG GTG GAG AAG AAG ACC GGC GAC GCC ATC AGC GAC GAC GAG AAC GAG AAC GAC AGC GAC 3'

MN606 (SEQ.ID.NO:34) 5' GTG CTG CTT GGC CTC CTG GGC GGT GAA CAG GGC GTG GGC GGT CTC GGT CTC GGC CTG GGT CAG GTA GTC GTT GTC GTT CAC GAT GAA GTC CAC CAG GTC CTC GCC GGT GTC GCT GTC GTT CTC GTT CTC GTC 3'

MN607(SEQ.ID.NO:35) 5' GCC CAG GAG GCC AAG CAG CAC CGC GAC GCC GTG CAG GTG CTG AAG CGC AAG TAC CTG GGC AGC CCC CTG AGC GAC ATC AGC GGC TGC GTC GAC AAC AAC ATC AGC CCC CGC CTG AAG GCC ATC TGC ATC GAG 3'

MN608 (SEQ.ID.NO:36) 5' CTC GTG GCG GCC CTC CAC CTG CAG CAT CTG CTG GGT CTC CAC CTC GGT GTT GCC GTA GCC GCT GTC CTC GCT CTC GAA CAG GCG GCG CTT GGC GGC GCG GCT CTG CTT CTC GAT GCA GAT GGC CTT CAG GC 3'

MN609 (SEQ.ID.NO:37) 5' CAG GTG GAG GGC CGC CAC GAG ACC GAG ACC CCC TGC AGC CAG TAC AGC GGC GGC AGC GGC GGC GGC TGC AGC CAG TAC AGC AGC GGC AGC GGC GGC GAG GGC GTG AGC GAG CGC CAC ACC ATC TGC CAG ACC 3'

MN610 (SEQ.ID.NO:38): 5' CTT GAA GGG GCG CAC CAG CTC GCT GAA GCT CAC GCC GTA CAG CTC CTT GAA CTT GGC CAG CAT GGC GGC CTT GGC GTT GCT GGT CTT CAG CAC GTT CAG GAT GTT GGT CAG AGG GGT CTG GCA GAT GGT GTG GCG 3'

MN611 (SEQ.ID.NO:39) 5' GAG CTG GTG CGC CCC TTC AAG AGC AAC AAG AGC ACC TGC TGC GAC TGG TGC ATC GCC GCC TTC GGC CTG ACC CCC AGC ATC GCC GAC AGC ATC AAG ACC CTG CTG CAG CAG TAC TGC CTG TAC CTG CAC ATC CAG 3'

MN612 (SEQ.ID.NO:40) 5' CAT GGG GCT CAC GCA CAG CAG CTT GCT CAG CAG CTT CTC GAT GGT CTC GCG GTT CTT GCC GCA CTT GTA GCG CAC CAG CAG CAG CAC CAC CAT GCC CCA GCT GCA GGC CAG GCT CTG GAT GTG CAG GTA CAG GCA G 3'

Figure 18:
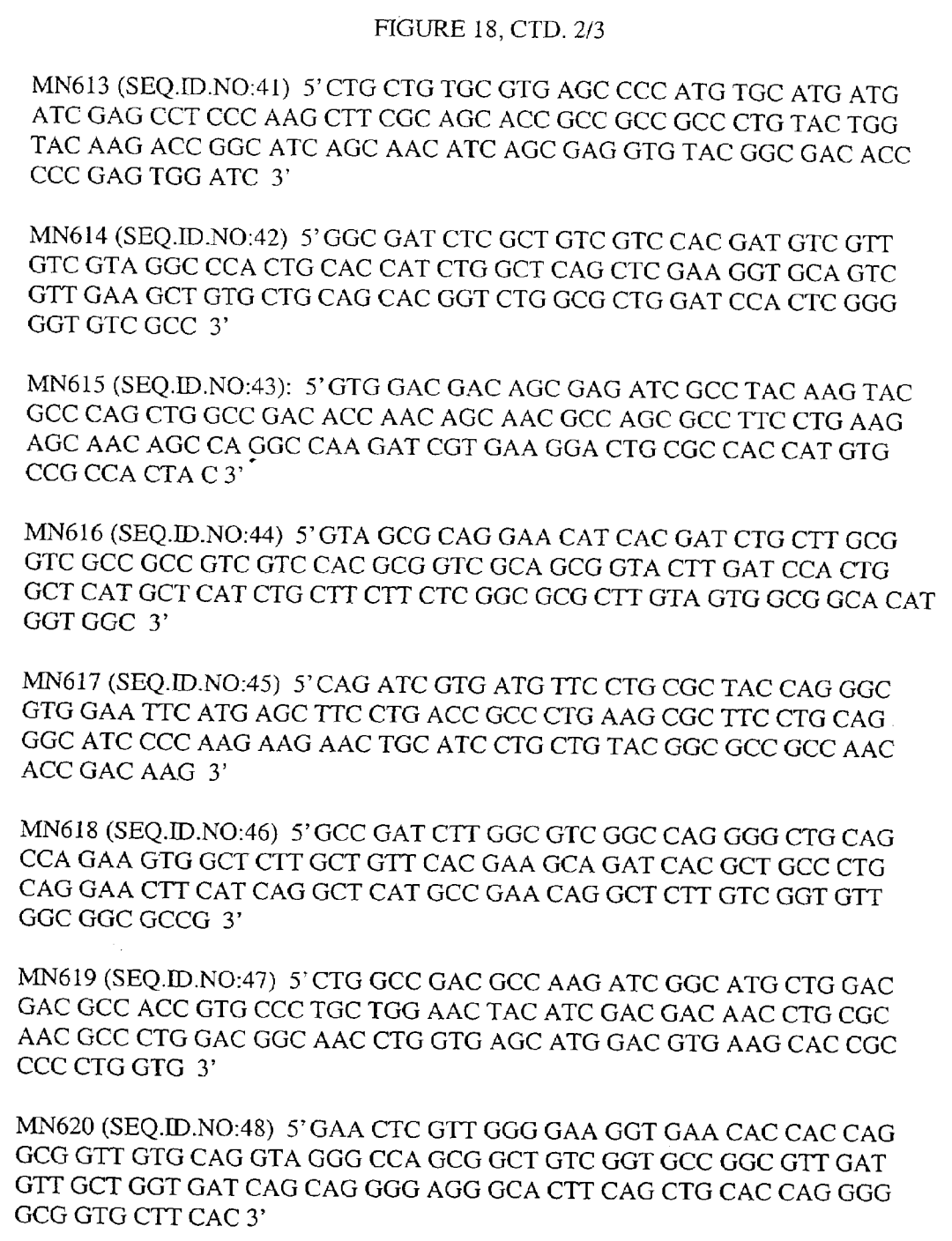

FIGURE 18, CTD. 2/3

MN613 (SEQ.ID.NO:41) 5' CTG CTG TGC GTG AGC CCC ATG TGC ATG ATG ATC GAG CCT CCC AAG CTT CGC AGC ACC GCC GCC GCC CTG TAC TGG TAC AAG ACC GGC ATC AGC AAC ATC AGC GAG GTG TAC GGC GAC ACC CCC GAG TGG ATC 3'

MN614 (SEQ.ID.NO:42) 5' GGC GAT CTC GCT GTC GTC CAC GAT GTC GTT GTC GTA GGC CCA CTG CAC CAT CTG GCT CAG CTC GAA GGT GCA GTC GTT GAA GCT GTG CTG CAG CAC GGT CTG GCG CTG GAT CCA CTC GGG GGT GTC GCC 3'

MN615 (SEQ.ID.NO:43): 5' GTG GAC GAC AGC GAG ATC GCC TAC AAG TAC GCC CAG CTG GCC GAC ACC AAC AGC AAC GCC AGC GCC TTC CTG AAG AGC AAC AGC CA GGC CAA GAT CGT GAA GGA CTG CGC CAC CAT GTG CCG CCA CTA C 3'

MN616 (SEQ.ID.NO:44) 5' GTA GCG CAG GAA CAT CAC GAT CTG CTT GCG GTC GCC GCC GTC GTC CAC GCG GTC GCA GCG GTA CTT GAT CCA CTG GCT CAT GCT CAT CTG CTT CTT CTC GGC GCG CTT GTA GTG GCG GCA CAT GGT GGC 3'

MN617 (SEQ.ID.NO:45) 5' CAG ATC GTG ATG TTC CTG CGC TAC CAG GGC GTG GAA TTC ATG AGC TTC CTG ACC GCC CTG AAG CGC TTC CTG CAG GGC ATC CCC AAG AAG AAC TGC ATC CTG CTG TAC GGC GCC GCC AAC ACC GAC AAG 3'

MN618 (SEQ.ID.NO:46) 5' GCC GAT CTT GGC GTC GGC CAG GGG CTG CAG CCA GAA GTG GCT CTT GCT GTT CAC GAA GCA GAT CAC GCT GCC CTG CAG GAA CTT CAT CAG GCT CAT GCC GAA CAG GCT CTT GTC GGT GTT GGC GGC GCCG 3'

MN619 (SEQ.ID.NO:47) 5' CTG GCC GAC GCC AAG ATC GGC ATG CTG GAC GAC GCC ACC GTG CCC TGC TGG AAC TAC ATC GAC GAC AAC CTG CGC AAC GCC CTG GAC GGC AAC CTG GTG AGC ATG GAC GTG AAG CAC CGC CCC CTG GTG 3'

MN620 (SEQ.ID.NO:48) 5' GAA CTC GTT GGG GAA GGT GAA CAC CAC CAG GCG GTT GTG CAG GTA GGG CCA GCG GCT GTC GGT GCC GGC GTT GAT GTT GCT GGT GAT CAG CAG GGG AGG GCA CTT CAG CTG CAC CAG GGG GCG GTG CTT CAC 3'

Figure 18:
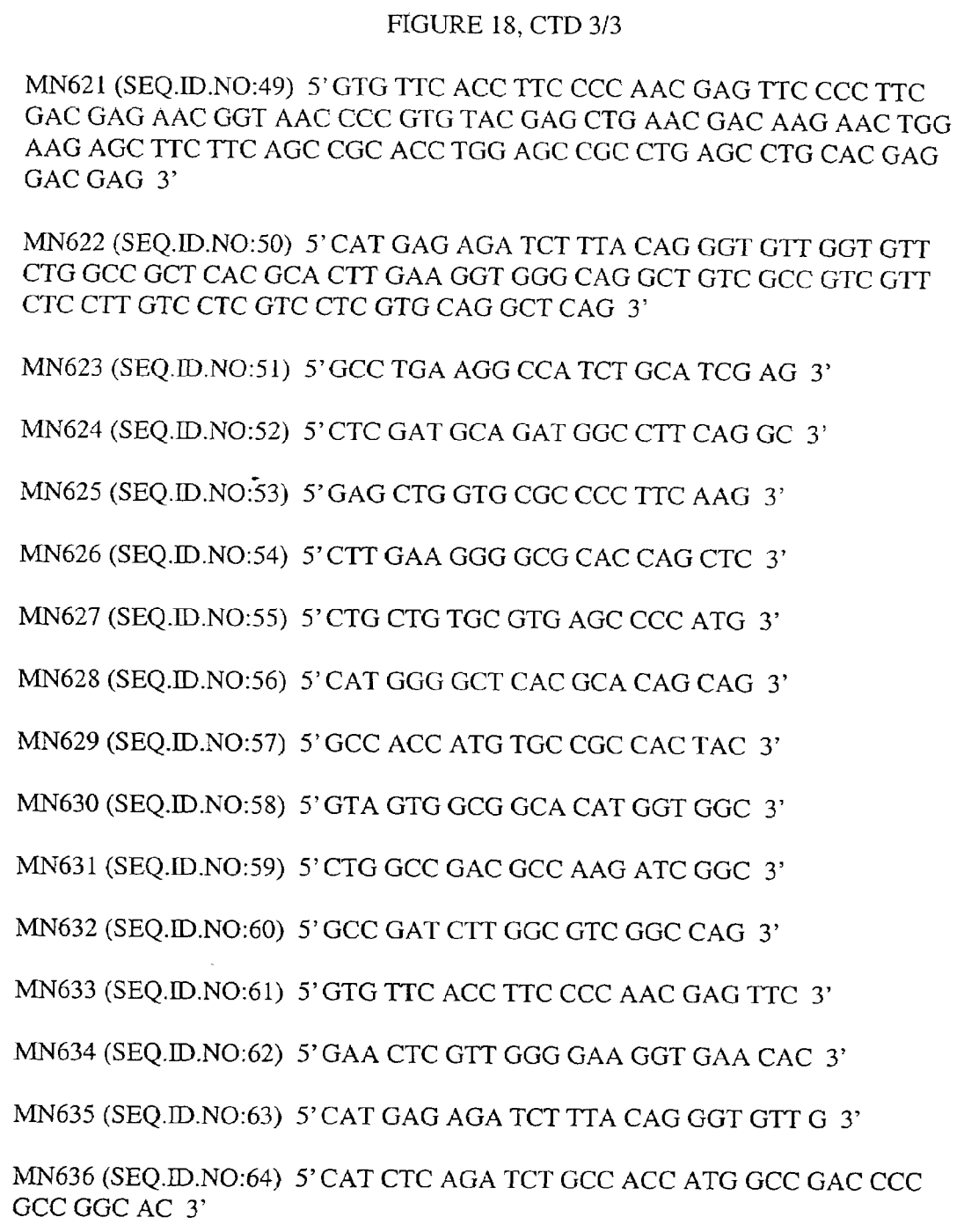

FIGURE 18, CTD 3/3

MN621 (SEQ.ID.NO:49) 5' GTG TTC ACC TTC CCC AAC GAG TTC CCC TTC GAC GAG AAC GGT AAC CCC GTG TAC GAG CTG AAC GAC AAG AAC TGG AAG AGC TTC TTC AGC CGC ACC TGG AGC CGC CTG AGC CTG CAC GAG GAC GAG 3'

MN622 (SEQ.ID.NO:50) 5' CAT GAG AGA TCT TTA CAG GGT GTT GGT GTT CTG GCC GCT CAC GCA CTT GAA GGT GGG CAG GCT GTC GCC GTC GTT CTC CTT GTC CTC GTC CTC GTG CAG GCT CAG 3'

MN623 (SEQ.ID.NO:51) 5' GCC TGA AGG CCA TCT GCA TCG AG 3'

MN624 (SEQ.ID.NO:52) 5' CTC GAT GCA GAT GGC CTT CAG GC 3'

MN625 (SEQ.ID.NO:53) 5' GAG CTG GTG CGC CCC TTC AAG 3'

MN626 (SEQ.ID.NO:54) 5' CTT GAA GGG GCG CAC CAG CTC 3'

MN627 (SEQ.ID.NO:55) 5' CTG CTG TGC GTG AGC CCC ATG 3'

MN628 (SEQ.ID.NO:56) 5' CAT GGG GCT CAC GCA CAG CAG 3'

MN629 (SEQ.ID.NO:57) 5' GCC ACC ATG TGC CGC CAC TAC 3'

MN630 (SEQ.ID.NO:58) 5' GTA GTG GCG GCA CAT GGT GGC 3'

MN631 (SEQ.ID.NO:59) 5' CTG GCC GAC GCC AAG ATC GGC 3'

MN632 (SEQ.ID.NO:60) 5' GCC GAT CTT GGC GTC GGC CAG 3'

MN633 (SEQ.ID.NO:61) 5' GTG TTC ACC TTC CCC AAC GAG TTC 3'

MN634 (SEQ.ID.NO:62) 5' GAA CTC GTT GGG GAA GGT GAA CAC 3'

MN635 (SEQ.ID.NO:63) 5' CAT GAG AGA TCT TTA CAG GGT GTT G 3'

MN636 (SEQ.ID.NO:64) 5' CAT CTC AGA TCT GCC ACC ATG GCC GAC CCC GCC GGC AC 3'

FIGURE 19

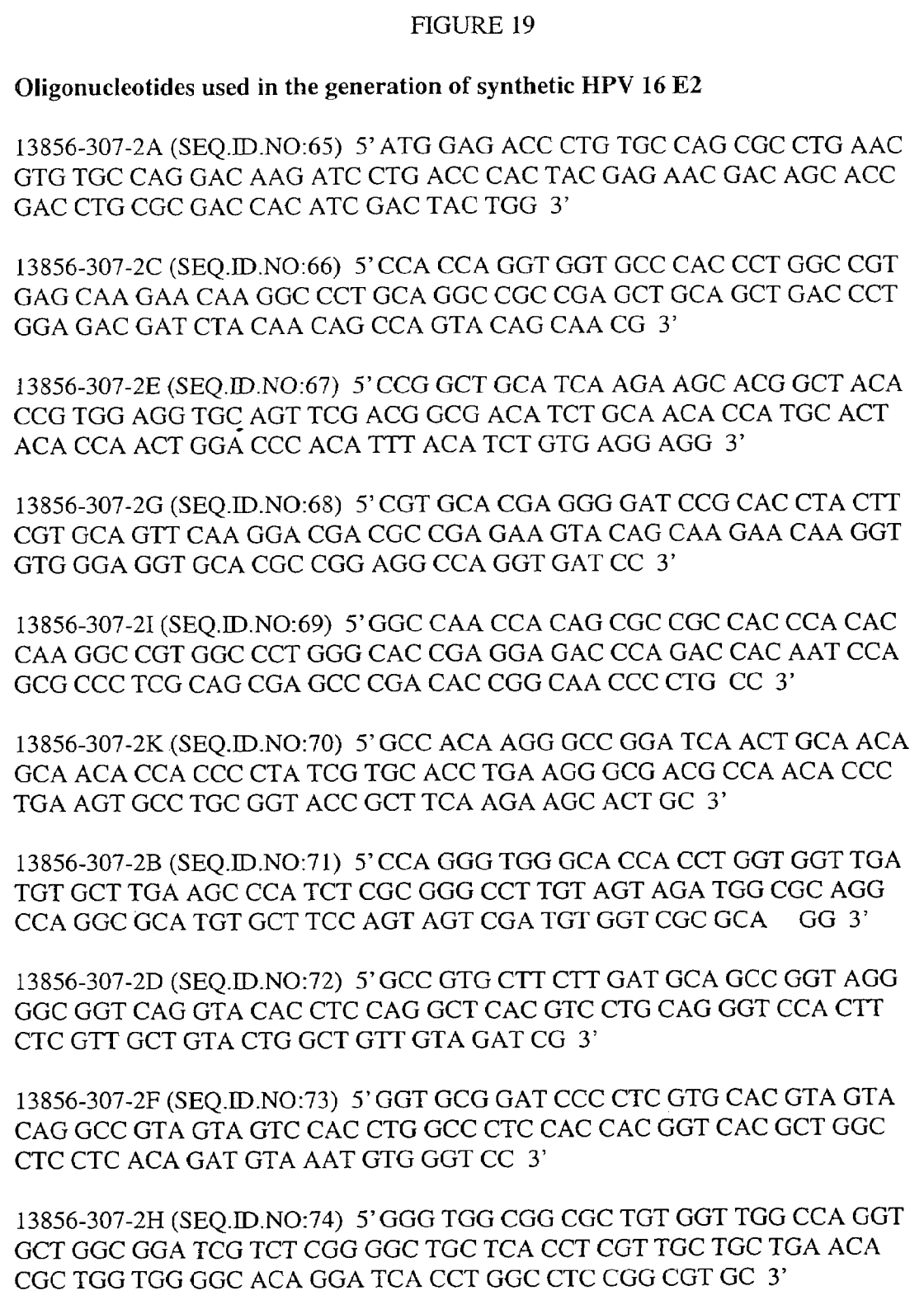

Oligonucleotides used in the generation of synthetic HPV 16 E2

13856-307-2A (SEQ.ID.NO:65) 5' ATG GAG ACC CTG TGC CAG CGC CTG AAC GTG TGC CAG GAC AAG ATC CTG ACC CAC TAC GAG AAC GAC AGC ACC GAC CTG CGC GAC CAC ATC GAC TAC TGG 3'

13856-307-2C (SEQ.ID.NO:66) 5' CCA CCA GGT GGT GCC CAC CCT GGC CGT GAG CAA GAA CAA GGC CCT GCA GGC CGC CGA GCT GCA GCT GAC CCT GGA GAC GAT CTA CAA CAG CCA GTA CAG CAA CG 3'

13856-307-2E (SEQ.ID.NO:67) 5' CCG GCT GCA TCA AGA AGC ACG GCT ACA CCG TGG AGG TGC AGT TCG ACG GCG ACA TCT GCA ACA CCA TGC ACT ACA CCA ACT GGA CCC ACA TTT ACA TCT GTG AGG AGG 3'

13856-307-2G (SEQ.ID.NO:68) 5' CGT GCA CGA GGG GAT CCG CAC CTA CTT CGT GCA GTT CAA GGA CGA CGC CGA GAA GTA CAG CAA GAA CAA GGT GTG GGA GGT GCA CGC CGG AGG CCA GGT GAT CC 3'

13856-307-2I (SEQ.ID.NO:69) 5' GGC CAA CCA CAG CGC CGC CAC CCA CAC CAA GGC CGT GGC CCT GGG CAC CGA GGA GAC CCA GAC CAC AAT CCA GCG CCC TCG CAG CGA GCC CGA CAC CGG CAA CCC CTG CC 3'

13856-307-2K (SEQ.ID.NO:70) 5' GCC ACA AGG GCC GGA TCA ACT GCA ACA GCA ACA CCA CCC CTA TCG TGC ACC TGA AGG GCG ACG CCA ACA CCC TGA AGT GCC TGC GGT ACC GCT TCA AGA AGC ACT GC 3'

13856-307-2B (SEQ.ID.NO:71) 5' CCA GGG TGG GCA CCA CCT GGT GGT TGA TGT GCT TGA AGC CCA TCT CGC GGG CCT TGT AGT AGA TGG CGC AGG CCA GGC GCA TGT GCT TCC AGT AGT CGA TGT GGT CGC GCA GG 3'

13856-307-2D (SEQ.ID.NO:72) 5' GCC GTG CTT CTT GAT GCA GCC GGT AGG GGC GGT CAG GTA CAC CTC CAG GCT CAC GTC CTG CAG GGT CCA CTT CTC GTT GCT GTA CTG GCT GTT GTA GAT CG 3'

13856-307-2F (SEQ.ID.NO:73) 5' GGT GCG GAT CCC CTC GTG CAC GTA GTA CAG GCC GTA GTA GTC CAC CTG GCC CTC CAC CAC GGT CAC GCT GGC CTC CTC ACA GAT GTA AAT GTG GGT CC 3'

13856-307-2H (SEQ.ID.NO:74) 5' GGG TGG CGG CGC TGT GGT TGG CCA GGT GCT GGC GGA TCG TCT CGG GGC TGC TCA CCT CGT TGC TGC TGA ACA CGC TGG TGG GGC ACA GGA TCA CCT GGC CTC CGG CGT GC 3'

Figure 19:
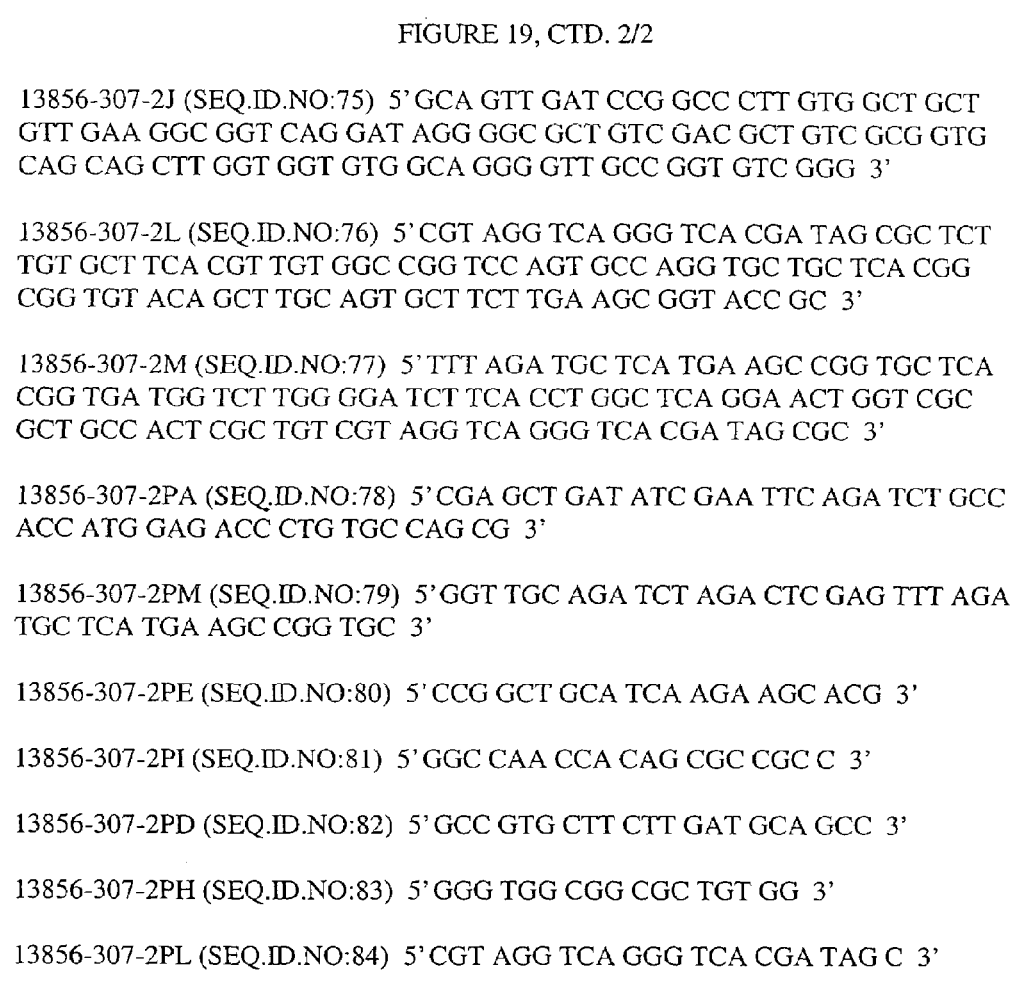

FIGURE 19, CTD. 2/2

13856-307-2J (SEQ.ID.NO:75) 5' GCA GTT GAT CCG GCC CTT GTG GCT GCT GTT GAA GGC GGT CAG GAT AGG GGC GCT GTC GAC GCT GTC GCG GTG CAG CAG CTT GGT GGT GTG GCA GGG GTT GCC GGT GTC GGG 3'

13856-307-2L (SEQ.ID.NO:76) 5' CGT AGG TCA GGG TCA CGA TAG CGC TCT TGT GCT TCA CGT TGT GGC CGG TCC AGT GCC AGG TGC TGC TCA CGG CGG TGT ACA GCT TGC AGT GCT TCT TGA AGC GGT ACC GC 3'

13856-307-2M (SEQ.ID.NO:77) 5' TTT AGA TGC TCA TGA AGC CGG TGC TCA CGG TGA TGG TCT TGG GGA TCT TCA CCT GGC TCA GGA ACT GGT CGC GCT GCC ACT CGC TGT CGT AGG TCA GGG TCA CGA TAG CGC 3'

13856-307-2PA (SEQ.ID.NO:78) 5' CGA GCT GAT ATC GAA TTC AGA TCT GCC ACC ATG GAG ACC CTG TGC CAG CG 3'

13856-307-2PM (SEQ.ID.NO:79) 5' GGT TGC AGA TCT AGA CTC GAG TTT AGA TGC TCA TGA AGC CGG TGC 3'

13856-307-2PE (SEQ.ID.NO:80) 5' CCG GCT GCA TCA AGA AGC ACG 3'

13856-307-2PI (SEQ.ID.NO:81) 5' GGC CAA CCA CAG CGC CGC C 3'

13856-307-2PD (SEQ.ID.NO:82) 5' GCC GTG CTT CTT GAT GCA GCC 3'

13856-307-2PH (SEQ.ID.NO:83) 5' GGG TGG CGG CGC TGT GG 3'

13856-307-2PL (SEQ.ID.NO:84) 5' CGT AGG TCA GGG TCA CGA TAG C 3'

FIGURE 20

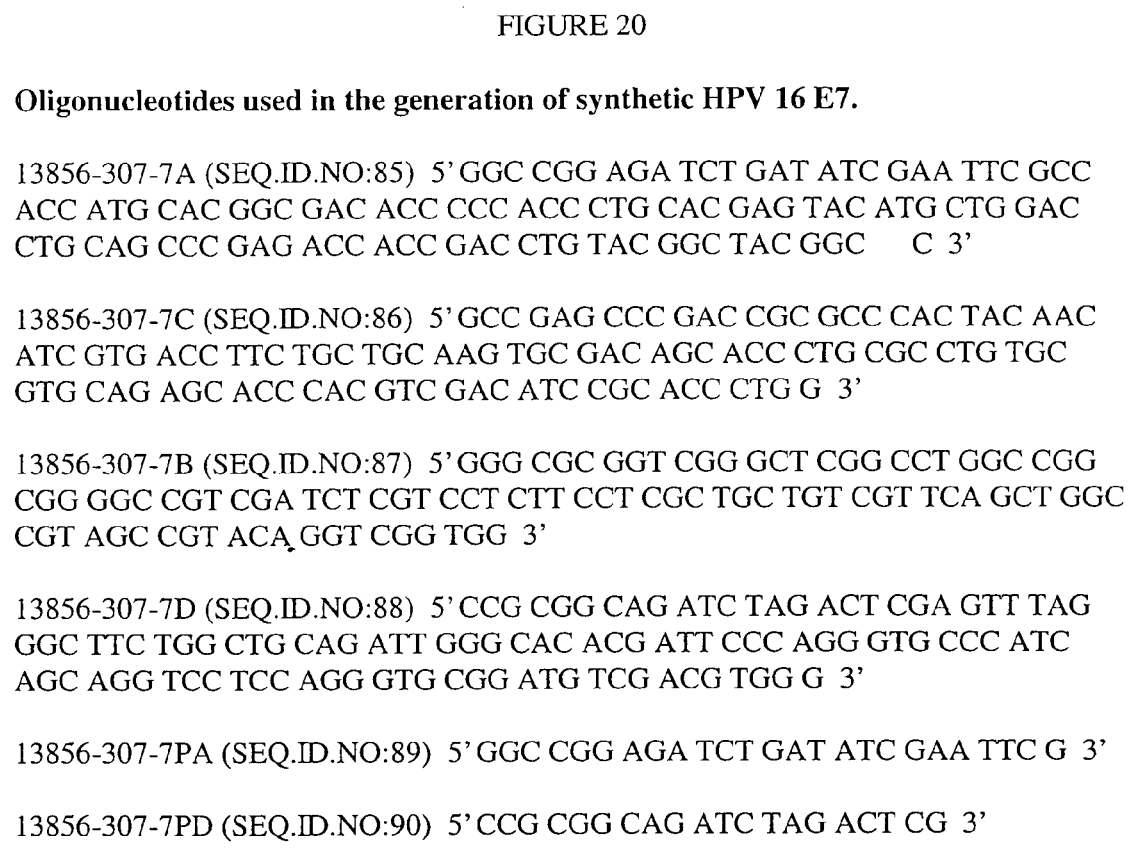

Oligonucleotides used in the generation of synthetic HPV 16 E7.

13856-307-7A (SEQ.ID.NO:85) 5' GGC CGG AGA TCT GAT ATC GAA TTC GCC ACC ATG CAC GGC GAC ACC CCC ACC CTG CAC GAG TAC ATG CTG GAC CTG CAG CCC GAG ACC ACC GAC CTG TAC GGC TAC GGC C 3'

13856-307-7C (SEQ.ID.NO:86) 5' GCC GAG CCC GAC CGC GCC CAC TAC AAC ATC GTG ACC TTC TGC TGC AAG TGC GAC AGC ACC CTG CGC CTG TGC GTG CAG AGC ACC CAC GTC GAC ATC CGC ACC CTG G 3'

13856-307-7B (SEQ.ID.NO:87) 5' GGG CGC GGT CGG GCT CGG CCT GGC CGG CGG GGC CGT CGA TCT CGT CCT CTT CCT CGC TGC TGT CGT TCA GCT GGC CGT AGC CGT ACA GGT CGG TGG 3'

13856-307-7D (SEQ.ID.NO:88) 5' CCG CGG CAG ATC TAG ACT CGA GTT TAG GGC TTC TGG CTG CAG ATT GGG CAC ACG ATT CCC AGG GTG CCC ATC AGC AGG TCC TCC AGG GTG CGG ATG TCG ACG TGG G 3'

13856-307-7PA (SEQ.ID.NO:89) 5' GGC CGG AGA TCT GAT ATC GAA TTC G 3'

13856-307-7PD (SEQ.ID.NO:90) 5' CCG CGG CAG ATC TAG ACT CG 3'

FIGURE 21

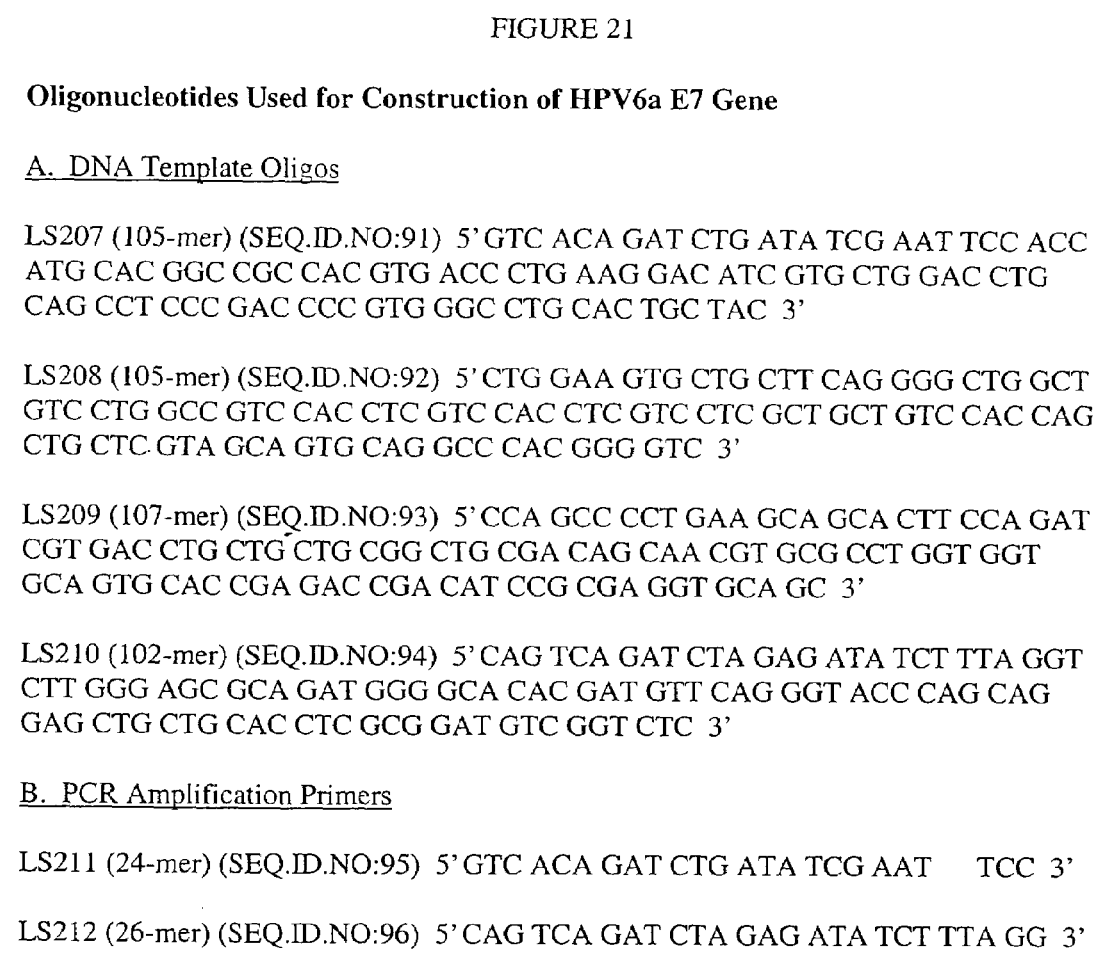

Oligonucleotides Used for Construction of HPV6a E7 Gene

A. DNA Template Oligos

LS207 (105-mer) (SEQ.ID.NO:91) 5' GTC ACA GAT CTG ATA TCG AAT TCC ACC ATG CAC GGC CGC CAC GTG ACC CTG AAG GAC ATC GTG CTG GAC CTG CAG CCT CCC GAC CCC GTG GGC CTG CAC TGC TAC 3'

LS208 (105-mer) (SEQ.ID.NO:92) 5' CTG GAA GTG CTG CTT CAG GGG CTG GCT GTC CTG GCC GTC CAC CTC GTC CAC CTC GTC CTC GCT GCT GTC CAC CAG CTG CTC GTA GCA GTG CAG GCC CAC GGG GTC 3'

LS209 (107-mer) (SEQ.ID.NO:93) 5' CCA GCC CCT GAA GCA GCA CTT CCA GAT CGT GAC CTG CTG CTG CGG CTG CGA CAG CAA CGT GCG CCT GGT GGT GCA GTG CAC CGA GAC CGA CAT CCG CGA GGT GCA GC 3'

LS210 (102-mer) (SEQ.ID.NO:94) 5' CAG TCA GAT CTA GAG ATA TCT TTA GGT CTT GGG AGC GCA GAT GGG GCA CAC GAT GTT CAG GGT ACC CAG CAG GAG CTG CTG CAC CTC GCG GAT GTC GGT CTC 3'

B. PCR Amplification Primers

LS211 (24-mer) (SEQ.ID.NO:95) 5' GTC ACA GAT CTG ATA TCG AAT TCC 3'

LS212 (26-mer) (SEQ.ID.NO:96) 5' CAG TCA GAT CTA GAG ATA TCT TTA GG 3'

FIGURE 22

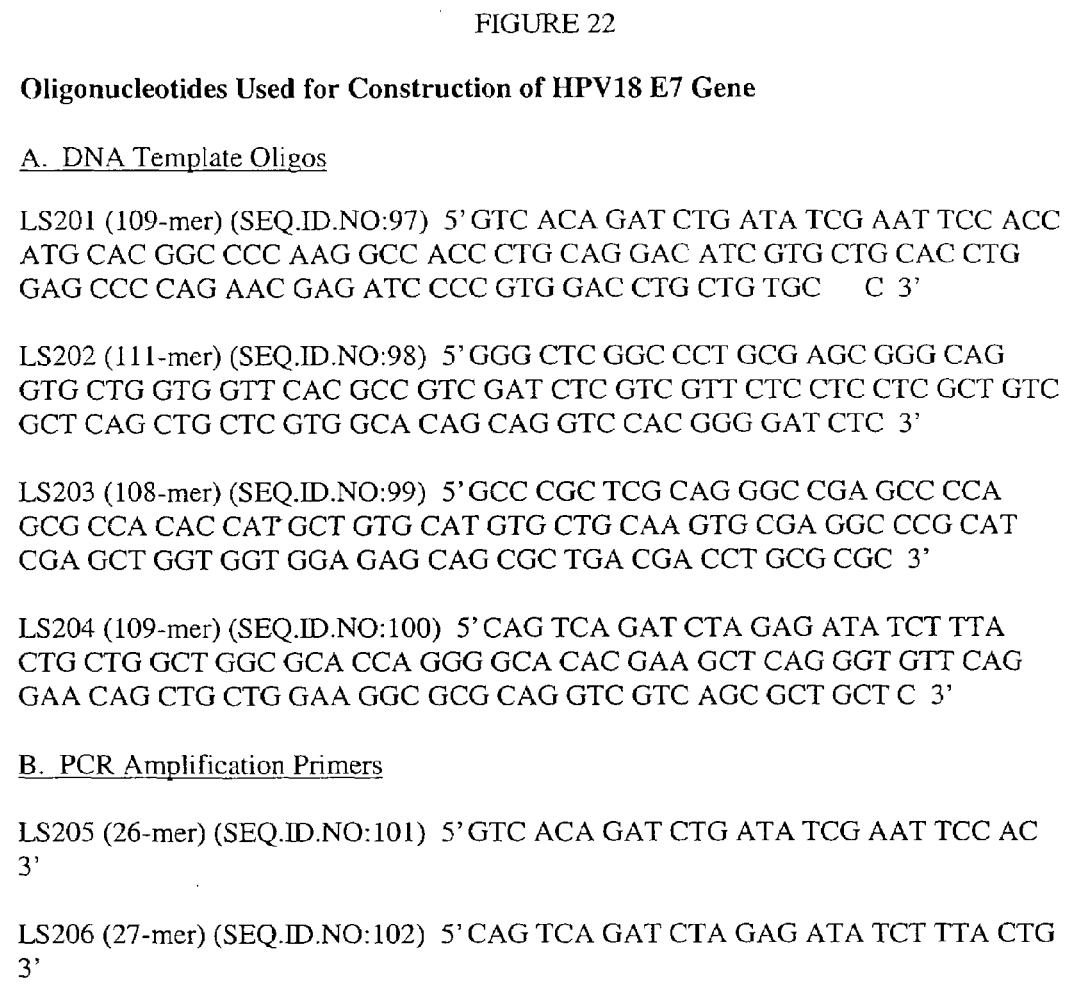

Oligonucleotides Used for Construction of HPV18 E7 Gene

A. DNA Template Oligos

LS201 (109-mer) (SEQ.ID.NO:97) 5' GTC ACA GAT CTG ATA TCG AAT TCC ACC ATG CAC GGC CCC AAG GCC ACC CTG CAG GAC ATC GTG CTG CAC CTG GAG CCC CAG AAC GAG ATC CCC GTG GAC CTG CTG TGC C 3'

LS202 (111-mer) (SEQ.ID.NO:98) 5' GGG CTC GGC CCT GCG AGC GGG CAG GTG CTG GTG GTT CAC GCC GTC GAT CTC GTC GTT CTC CTC CTC GCT GTC GCT CAG CTG CTC GTG GCA CAG CAG GTC CAC GGG GAT CTC 3'

LS203 (108-mer) (SEQ.ID.NO:99) 5' GCC CGC TCG CAG GGC CGA GCC CCA GCG CCA CAC CAT GCT GTG CAT GTG CTG CAA GTG CGA GGC CCG CAT CGA GCT GGT GGT GGA GAG CAG CGC TGA CGA CCT GCG CGC 3'

LS204 (109-mer) (SEQ.ID.NO:100) 5' CAG TCA GAT CTA GAG ATA TCT TTA CTG CTG GCT GGC GCA CCA GGG GCA CAC GAA GCT CAG GGT GTT CAG GAA CAG CTG CTG GAA GGC GCG CAG GTC GTC AGC GCT GCT C 3'

B. PCR Amplification Primers

LS205 (26-mer) (SEQ.ID.NO:101) 5' GTC ACA GAT CTG ATA TCG AAT TCC AC 3'

LS206 (27-mer) (SEQ.ID.NO:102) 5' CAG TCA GAT CTA GAG ATA TCT TTA CTG 3'

FIGURE 23

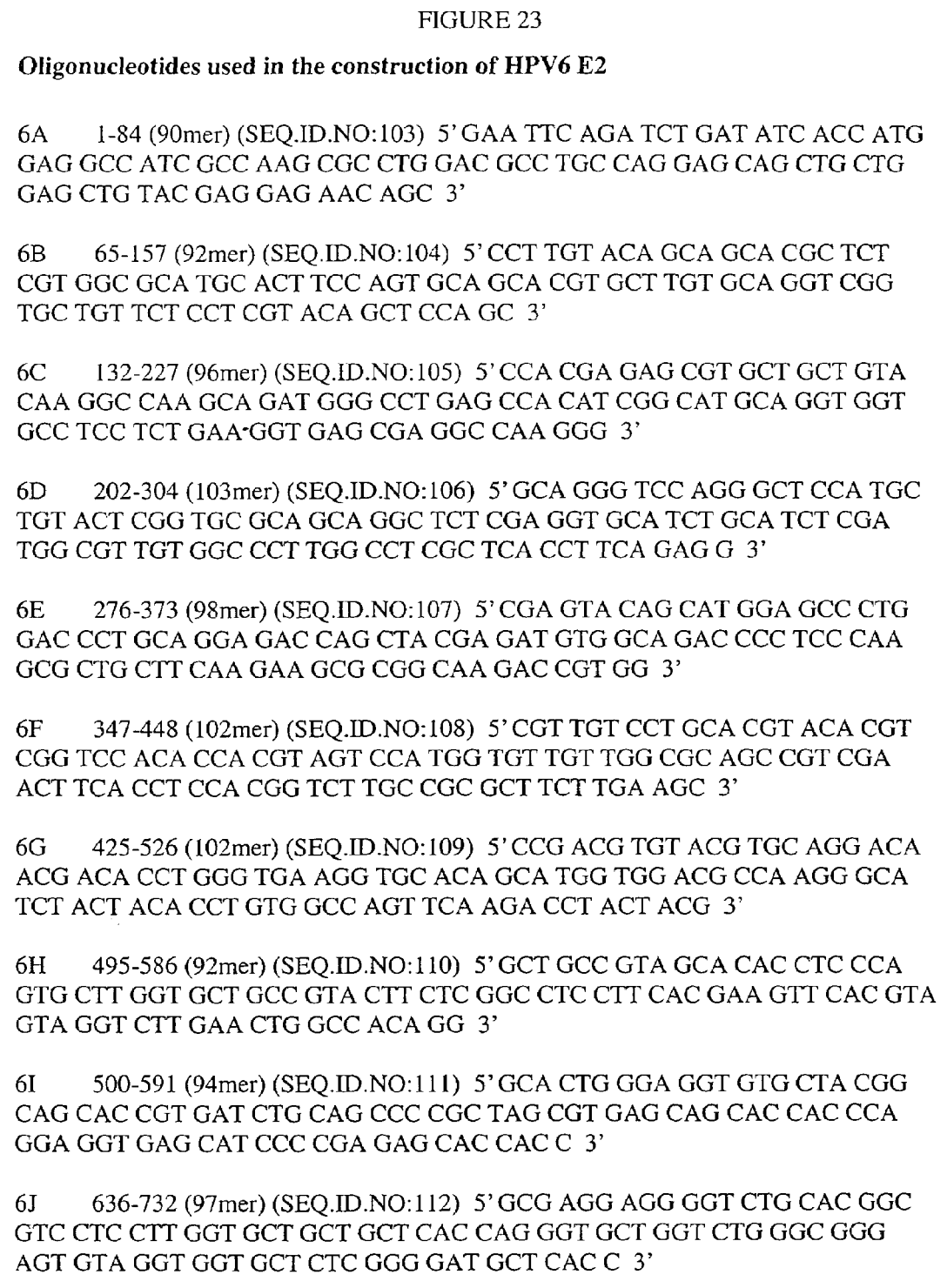

Oligonucleotides used in the construction of HPV6 E2

6A 1-84 (90mer) (SEQ.ID.NO:103) 5' GAA TTC AGA TCT GAT ATC ACC ATG GAG GCC ATC GCC AAG CGC CTG GAC GCC TGC CAG GAG CAG CTG CTG GAG CTG TAC GAG GAG AAC AGC 3'

6B 65-157 (92mer) (SEQ.ID.NO:104) 5' CCT TGT ACA GCA GCA CGC TCT CGT GGC GCA TGC ACT TCC AGT GCA GCA CGT GCT TGT GCA GGT CGG TGC TGT TCT CCT CGT ACA GCT CCA GC 3'

6C 132-227 (96mer) (SEQ.ID.NO:105) 5' CCA CGA GAG CGT GCT GCT GTA CAA GGC CAA GCA GAT GGG CCT GAG CCA CAT CGG CAT GCA GGT GGT GCC TCC TCT GAA GGT GAG CGA GGC CAA GGG 3'

6D 202-304 (103mer) (SEQ.ID.NO:106) 5' GCA GGG TCC AGG GCT CCA TGC TGT ACT CGG TGC GCA GCA GGC TCT CGA GGT GCA TCT GCA TCT CGA TGG CGT TGT GGC CCT TGG CCT CGC TCA CCT TCA GAG G 3'

6E 276-373 (98mer) (SEQ.ID.NO:107) 5' CGA GTA CAG CAT GGA GCC CTG GAC CCT GCA GGA GAC CAG CTA CGA GAT GTG GCA GAC CCC TCC CAA GCG CTG CTT CAA GAA GCG CGG CAA GAC CGT GG 3'

6F 347-448 (102mer) (SEQ.ID.NO:108) 5' CGT TGT CCT GCA CGT ACA CGT CGG TCC ACA CCA CGT AGT CCA TGG TGT TGT TGG CGC AGC CGT CGA ACT TCA CCT CCA CGG TCT TGC CGC GCT TCT TGA AGC 3'

6G 425-526 (102mer) (SEQ.ID.NO:109) 5' CCG ACG TGT ACG TGC AGG ACA ACG ACA CCT GGG TGA AGG TGC ACA GCA TGG TGG ACG CCA AGG GCA TCT ACT ACA CCT GTG GCC AGT TCA AGA CCT ACT ACG 3'

6H 495-586 (92mer) (SEQ.ID.NO:110) 5' GCT GCC GTA GCA CAC CTC CCA GTG CTT GGT GCT GCC GTA CTT CTC GGC CTC CTT CAC GAA GTT CAC GTA GTA GGT CTT GAA CTG GCC ACA GG 3'

6I 500-591 (94mer) (SEQ.ID.NO:111) 5' GCA CTG GGA GGT GTG CTA CGG CAG CAC CGT GAT CTG CAG CCC CGC TAG CGT GAG CAG CAC CAC CCA GGA GGT GAG CAT CCC CGA GAG CAC CAC C 3'

6J 636-732 (97mer) (SEQ.ID.NO:112) 5' GCG AGG AGG GGT CTG CAC GGC GTC CTC CTT GGT GCT GCT GCT CAC CAG GGT GCT GGT CTG GGC GGG AGT GTA GGT GGT GCT CTC GGG GAT GCT CAC C 3'

Figure 23:
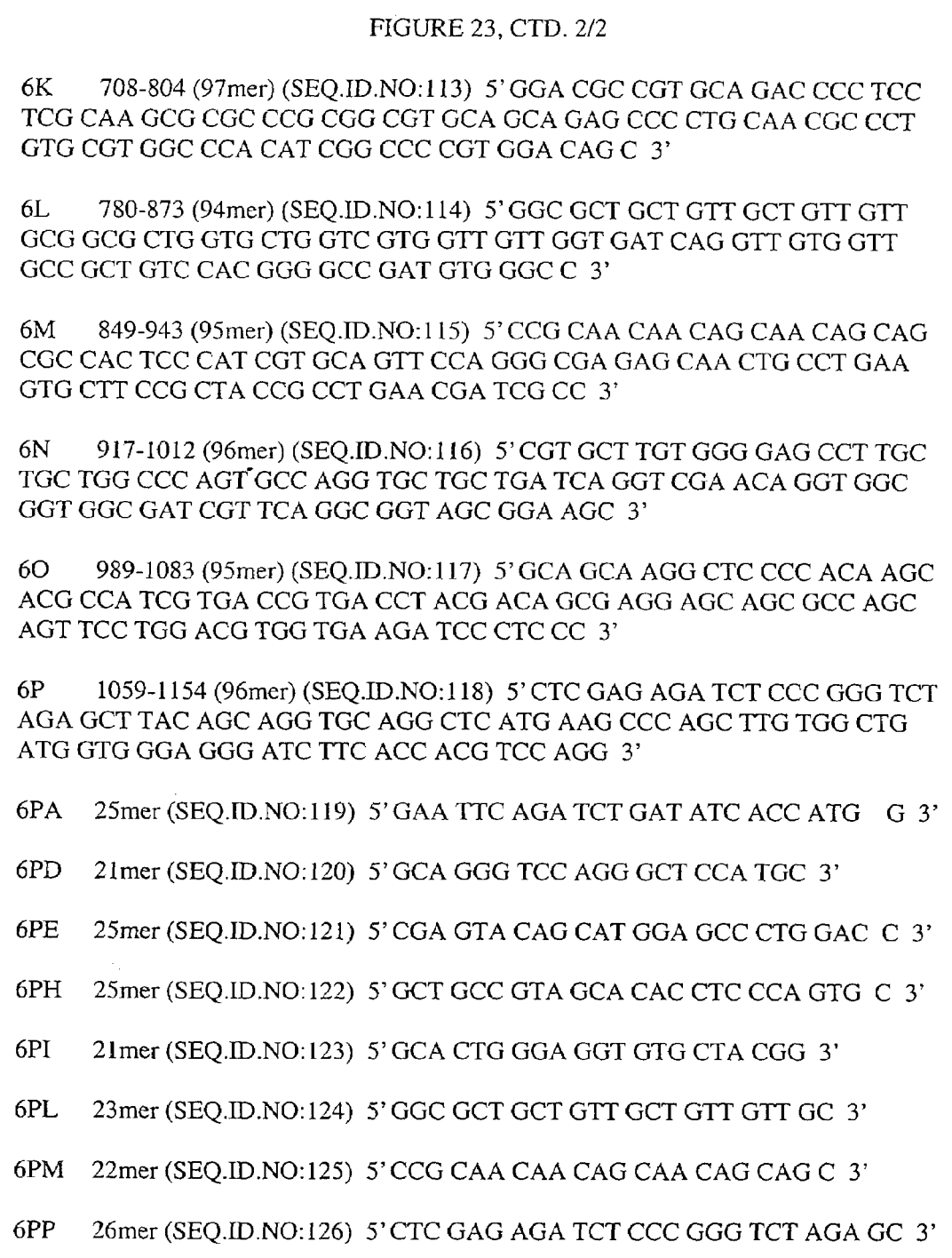

FIGURE 23, CTD. 2/2

6K 708-804 (97mer) (SEQ.ID.NO:113) 5' GGA CGC CGT GCA GAC CCC TCC TCG CAA GCG CGC CCG CGG CGT GCA GCA GAG CCC CTG CAA CGC CCT GTG CGT GGC CCA CAT CGG CCC CGT GGA CAG C 3'

6L 780-873 (94mer) (SEQ.ID.NO:114) 5' GGC GCT GCT GTT GCT GTT GTT GCG GCG CTG GTG CTG GTC GTG GTT GTT GGT GAT CAG GTT GTG GTT GCC GCT GTC CAC GGG GCC GAT GTG GGC C 3'

6M 849-943 (95mer) (SEQ.ID.NO:115) 5' CCG CAA CAA CAG CAA CAG CAG CGC CAC TCC CAT CGT GCA GTT CCA GGG CGA GAG CAA CTG CCT GAA GTG CTT CCG CTA CCG CCT GAA CGA TCG CC 3'

6N 917-1012 (96mer) (SEQ.ID.NO:116) 5' CGT GCT TGT GGG GAG CCT TGC TGC TGG CCC AGT GCC AGG TGC TGC TGA TCA GGT CGA ACA GGT GGC GGT GGC GAT CGT TCA GGC GGT AGC GGA AGC 3'

6O 989-1083 (95mer) (SEQ.ID.NO:117) 5' GCA GCA AGG CTC CCC ACA AGC ACG CCA TCG TGA CCG TGA CCT ACG ACA GCG AGG AGC AGC GCC AGC AGT TCC TGG ACG TGG TGA AGA TCC CTC CC 3'

6P 1059-1154 (96mer) (SEQ.ID.NO:118) 5' CTC GAG AGA TCT CCC GGG TCT AGA GCT TAC AGC AGG TGC AGG CTC ATG AAG CCC AGC TTG TGG CTG ATG GTG GGA GGG ATC TTC ACC ACG TCC AGG 3'

6PA 25mer (SEQ.ID.NO:119) 5' GAA TTC AGA TCT GAT ATC ACC ATG G 3'

6PD 21mer (SEQ.ID.NO:120) 5' GCA GGG TCC AGG GCT CCA TGC 3'

6PE 25mer (SEQ.ID.NO:121) 5' CGA GTA CAG CAT GGA GCC CTG GAC C 3'

6PH 25mer (SEQ.ID.NO:122) 5' GCT GCC GTA GCA CAC CTC CCA GTG C 3'

6PI 21mer (SEQ.ID.NO:123) 5' GCA CTG GGA GGT GTG CTA CGG 3'

6PL 23mer (SEQ.ID.NO:124) 5' GGC GCT GCT GTT GCT GTT GTT GC 3'

6PM 22mer (SEQ.ID.NO:125) 5' CCG CAA CAA CAG CAA CAG CAG C 3'

6PP 26mer (SEQ.ID.NO:126) 5' CTC GAG AGA TCT CCC GGG TCT AGA GC 3'

FIGURE 24

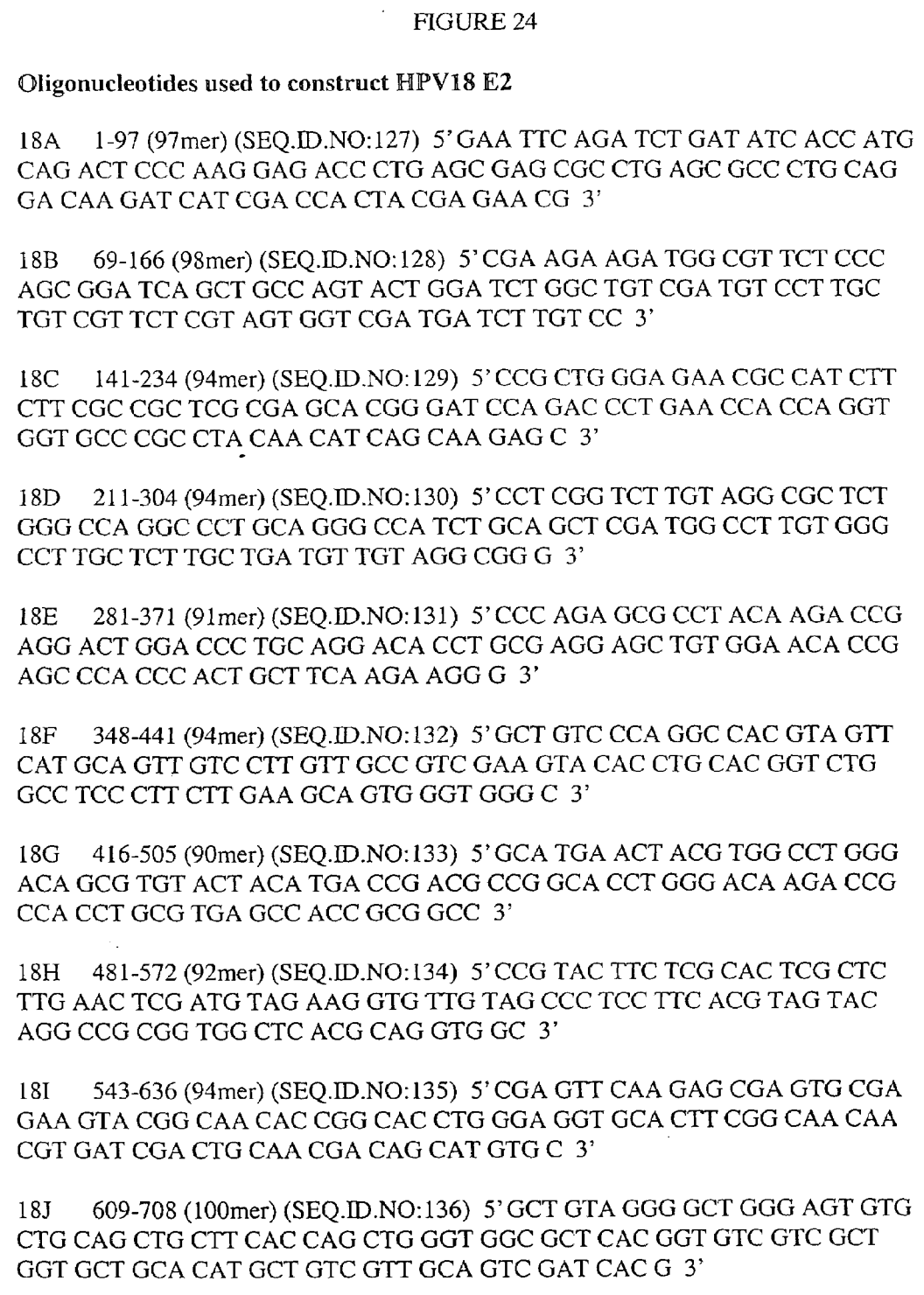

Oligonucleotides used to construct HPV18 E2

18A 1-97 (97mer) (SEQ.ID.NO:127) 5' GAA TTC AGA TCT GAT ATC ACC ATG CAG ACT CCC AAG GAG ACC CTG AGC GAG CGC CTG AGC GCC CTG CAG GA CAA GAT CAT CGA CCA CTA CGA GAA CG 3'

18B 69-166 (98mer) (SEQ.ID.NO:128) 5' CGA AGA AGA TGG CGT TCT CCC AGC GGA TCA GCT GCC AGT ACT GGA TCT GGC TGT CGA TGT CCT TGC TGT CGT TCT CGT AGT GGT CGA TGA TCT TGT CC 3'

18C 141-234 (94mer) (SEQ.ID.NO:129) 5' CCG CTG GGA GAA CGC CAT CTT CTT CGC CGC TCG CGA GCA CGG GAT CCA GAC CCT GAA CCA CCA GGT GGT GCC CGC CTA CAA CAT CAG CAA GAG C 3'

18D 211-304 (94mer) (SEQ.ID.NO:130) 5' CCT CGG TCT TGT AGG CGC TCT GGG CCA GGC CCT GCA GGG CCA TCT GCA GCT CGA TGG CCT TGT GGG CCT TGC TCT TGC TGA TGT TGT AGG CGG G 3'

18E 281-371 (91mer) (SEQ.ID.NO:131) 5' CCC AGA GCG CCT ACA AGA CCG AGG ACT GGA CCC TGC AGG ACA CCT GCG AGG AGC TGT GGA ACA CCG AGC CCA CCC ACT GCT TCA AGA AGG G 3'

18F 348-441 (94mer) (SEQ.ID.NO:132) 5' GCT GTC CCA GGC CAC GTA GTT CAT GCA GTT GTC CTT GTT GCC GTC GAA GTA CAC CTG CAC GGT CTG GCC TCC CTT CTT GAA GCA GTG GGT GGG C 3'

18G 416-505 (90mer) (SEQ.ID.NO:133) 5' GCA TGA ACT ACG TGG CCT GGG ACA GCG TGT ACT ACA TGA CCG ACG CCG GCA CCT GGG ACA AGA CCG CCA CCT GCG TGA GCC ACC GCG GCC 3'

18H 481-572 (92mer) (SEQ.ID.NO:134) 5' CCG TAC TTC TCG CAC TCG CTC TTG AAC TCG ATG TAG AAG GTG TTG TAG CCC TCC TTC ACG TAG TAC AGG CCG CGG TGG CTC ACG CAG GTG GC 3'

18I 543-636 (94mer) (SEQ.ID.NO:135) 5' CGA GTT CAA GAG CGA GTG CGA GAA GTA CGG CAA CAC CGG CAC CTG GGA GGT GCA CTT CGG CAA CAA CGT GAT CGA CTG CAA CGA CAG CAT GTG C 3'

18J 609-708 (100mer) (SEQ.ID.NO:136) 5' GCT GTA GGG GCT GGG AGT GTG CTG CAG CTG CTT CAC CAG CTG GGT GGC GCT CAC GGT GTC GTC GCT GGT GCT GCA CAT GCT GTC GTT GCA GTC GAT CAC G 3'

FIGURE 24, CTD. 2/2

18K 687-779 (93mer) (SEQ.ID.NO:137) 5' GCA CAC TCC CAG CCC CTA CAG CAG CAC CGT GAG CGT GGG CAC CGC CAA GAC CTA CGG CCA GAC CAG CGC CGC CAC TCG CCC TGG CCA CTG CGG 3'

18L 758-853 (96mer) (SEQ.ID.NO:138) 5' GCT TGT TGT TGC CGG TGG CGG TGG CGG CGC CCA GCA GAG GGT TCA CGG GCC CGC AGT GCT GCT TCT CGG CCA GGC CGC AGT GGC CAG GGC GAG TGG 3'

18M 829-925 (97mer) (SEQ.ID.NO:139) 5' GCC ACC GCC ACC GGC AAC AAC AAG CGC CGC AAG CTG TGC AGC GGC AAC ACC ACT CCC ATC ATC CAC CTG AAG GGC GAC CGC AAC AGC CTG AAG TGC C 3'

18N 900-996 (97mer) (SEQ.ID.NO:140) 5' GGC GCC GGT CCA GTG CCA GGT GCT GCT GAT GTC GCG GTA GTG GTC GCT GTG CTT GCG CAG GCG GTA CCG CAG GCA CTT CAG GCT GTT GCG GTC GCC C 3'

18O 974-1072 (99mer) (SEQ.ID.NO:141) 5' GCA CCT GGC ACT GGA CCG GCG CCG GGA ACG AGA AGA CCG GCA TCC TGA CCG TGA CCT ACC ACA GCG AGA CCC AGC GCA CCA AGT TCC TGA ACA CCG TGG 3'

18P 1048-1145 (98mer) (SEQ.ID.NO:142) 5' CTC GAG AGA TCT CCC GGG TCT AGA GCT TAC ATG GTC ATG TAG CCC ACC AGG ATC TGC ACG CTG TCG GGG ATG GCC ACG GTG TTC AGG AAC TTG GTG CG 3'

18PA 25mer (SEQ.ID.NO:143) 5' GAA TTC AGA TCT GAT ATC ACC ATG C 3'

18PD 23mer (SEQ.ID.NO:144) 5' CCT CGG TCT TGT AGG CGC TCT GG 3'

18PE 21mer (SEQ.ID.NO:145) 5' CCC AGA GCG CCT ACA AGA CCG 3'

18PH 21mer (SEQ.ID.NO:146) 5' CCG TAC TTC TCG CAC TCG CTC 3'

18PI 20mer (SEQ.ID.NO:147) 5' CGA GTT CAA GAG CGA GTG CG 3'

18PL 21mer (SEQ.ID.NO:148) 5' GCT TGT TGT TGC CGG TGG CGG 3'

18PM 25mer (SEQ.ID.NO:149) 5' GCC ACC GCC ACC GGC AAC AAC AAG C 3'

18PP 26mer (SEQ.ID.NO:150) 5' CTC GAG AGA TCT CCC GGG TCT AGA GC 3'

SYNTHETIC HUMAN PAPILLOMAVIRUS GENES

This application claims priority from U.S. Provisional Patent Application No. 60/150,728, filed Aug. 25, 1999, and U.S. Provisional Patent Application No. 60/210,143, filed Jun. 7, 2000.

FIELD OF THE INVENTION

This invention relates to human papillomavirus (HPV) genes which have been codon-optimized for expression in a human cellular environment, and their use with adenoviral vectors and or plasmid vectors as vaccines.

BACKGROUND OF THE INVENTION

Papillomavirus infections occur in a variety of animals, including humans, sheep, dogs, cats, rabbits, snakes, monkeys and cows. Papillomaviruses infect epithelial cells, generally inducing benign epithelial or fibroepithelial tumors at the site of infection. Papillomaviruses are species specific infective agents; a human papillomavirus cannot infect a non-human.

Papillomaviruses are small (50–60 nm), nonenveloped, icosahedral DNA viruses what encode up to eight early and two late genes. The open reading frames (ORFs) of the virus are designated E1 to E7 and L1 and L2, where "E" denotes early and "L" denotes late. L1 and L2 code for virus capsid proteins. The early genes are associated with functions such as viral replication and cellular transformation.

In humans, different HPV types cause distinct diseases, ranging from benign warts (for examples HPV types 1, 2, 3) to highly invasive genital and anal carcinomas (HPV types 16 and 18). At present there is not a satisfactory therapeutic regimen for these diseases.

Immunological studies in animals have shown that the production of neutralizing antibodies to papillomavirus antigens prevents infection with the homologous virus. However, development of a vaccine has been hindered by the difficulties associated with culture of the papillomavirus in vitro.

Vaccination is an effective form of disease prevention and has proven successful against several types of viral infection. However, to date, attempts to generate an effective HPV vaccine have not been entirely successful.

SUMMARY OF THE INVENTION

This invention relates to oligonucleotides which encode a human papillomavirus (HPV) protein which has been codon-optimized for efficient expression in a host cell; preferably the oligonucleotides are DNA. In one embodiment, the polynucleotides encode a protein which retains its wild-type amino acid sequence. In an alternate embodiment, the polynucleotides encode a mutated form of a HPV protein which has reduced protein function as compared to wild-type protein, but which maintains immunogenicity. This invention also relates to the mutated HPV proteins so encoded.

In preferred embodiments, the protein is selected from the group consisting of: L1, L2, E1, E2, E4, E5, E6 and E7 proteins. Particularly preferred are L1, L2, E2, and E7 proteins.

Another aspect of this invention is a vector carrying the polynucleotides encoding a codon-optimized HPV protein. Yet another aspect of this invention are host cells containing these vectors.

In a preferred embodiment, the vector is an adenoviral vector. In a particularly preferred embodiment, the adenoviral vector is a vaccine vector comprising an adenoviral genome with a deletion in the E1 region, and an insert in the E1 region, wherein the insert comprises an expression cassette comprising:

a) a polynucleotide encoding an HPV protein selected from the group consisting of L1, E1, E2, and E7 proteins or mutant forms thereof, wherein the polynucleotide is codon-optimized for expression in a human host cell; and b) a promoter operably linked to the polynucleotide.

Another type of vector which is envisioned by this invention is a shuttle plasmid vector comprising a plasmid portion and an adenoviral portion, the adenoviral portion comprising: an adenoviral genome with a deletion in the E1 region, and an insert in the E1 region, wherein the insert comprises an expression cassette comprising:

a) a polynucleotide encoding an HPV protein selected from the group consisting of L1, E1, E2, and E7 proteins, wherein the polynucleotide is codon-optimized for expression in a human host cell; and b) a promoter operably linked to the polynucleotide.

This invention also is directed to plasmid vaccine vectors, which comprise a plasmid portion and an expressible cassette comprising a) a polynucleotide encoding an HPV protein selected from the group consisting of L1, E1, E2, and E7 proteins, wherein the polynucleotide is codon-optimized for expression in a human host cell; and b) a promoter operably linked to the polynucleotide.

This invention also relates to vaccine compositions comprising a vector which carries the oligonucleotides to a human host, and allows for expression of the encoded protein. The protein is expressed in an amount sufficient to induce an immune response. In preferred embodiments, the vector is a plasmid vector or an adenoviral vector.

This invention also relates to a method of making a HPV protein comprising expressing in a host cell a synthetic polynucleotide encoding a human papillomavirus (HPV) protein, or mutated form of a HPV protein which has reduced protein function as compared to wild-type protein, but which maintains immuno-genicity, the polynucleotide sequence comprising codons optimized for expression in a human host.

BRIEF DECRIPTION OF THE DRAWINGS

FIG. 1 is the nucleotide sequence of a codon-optimized HPV16 L1 gene (SEQ.ID.NO:1).

FIG. 2 is the nucleotide sequence of a codon-optimized HPV16 E1 gene (SEQ.ID.NO:2). In this particular sequence, there are further mutations which changes the amino acid sequence of the expressed protein—the glycine residue at position 428 has been converted to aspartic acid, and the tryptophan residue at position 439 is now arginine.

FIG. 3 is the nucleotide sequence of a codon-optimized HPV16 E2 gene (SEQ.ID.NO:3). In this particular sequence, the glutamic acid residue at position 39 has been changed to an alanine, and the isoleucine residue at position 73 has also been changed to an alanine.

FIG. 4 is the nucleotide sequence of a codon-optimized HPV16 E7 gene. (SEQ.ID.NO:4). In this particular sequence, the cysteine residue at position 24 has been changed to glycine, and the glutamic acid residue at position 26 has been changed to a glycine.

FIG. 5 is the nucleotide sequence of a codon-optimized HPV6a E7 gene (SEQ.ID.NO:5).

FIG. 6 is the nucleotide sequence of a codon-optimized HPV18 E7 gene (SEQ.ID.NO:6).

FIG. 7 is the nucleotide sequence of a codon-optimized HPV6a E2 gene (SEQ.ID.NO:7).

FIG. 8 is the nucleotide sequence of a codon-optimized HPV18 E2 gene (SEQ.ID.NO:8).

FIG. 17 is a table of oligonucleotides (SEQ.ID.NOS: 9–32) used to generate synthetic HPV16 L1.

FIG. 18 is a table of oligonucleotides (SEQ.ID.NOS: 33–64) used to generate synthetic HPV16 E1.

FIG. 19 is a table of oligonucleotides (SEQ.ID.NOS: 65–84) used to generate synthetic HPV16 E2.

FIG. 20 is a table of oligonucleotides (SEQ.ID.NOS: 85–90) used to generate synthetic HPV16 E7.

FIG. 21 is a table of oligonucleotides (SEQ.ID.NOS: 91–96) used to generate synthetic HPV6a E7.

FIG. 22 is a table of oligonucleotides (SEQ.ID.NOS: 97–102) used to generate synthetic HPV18 E7.

FIG. 23 is a table of oligonucleotides (SEQ.ID.NOS: 103–126) used to generate synthetic HPV6a E2.

FIG. 24 is a table of oligonucleotides (SEQ.ID.NOS: 127–150) used to generate synthetic HPV 18 E2.

Figure 25:
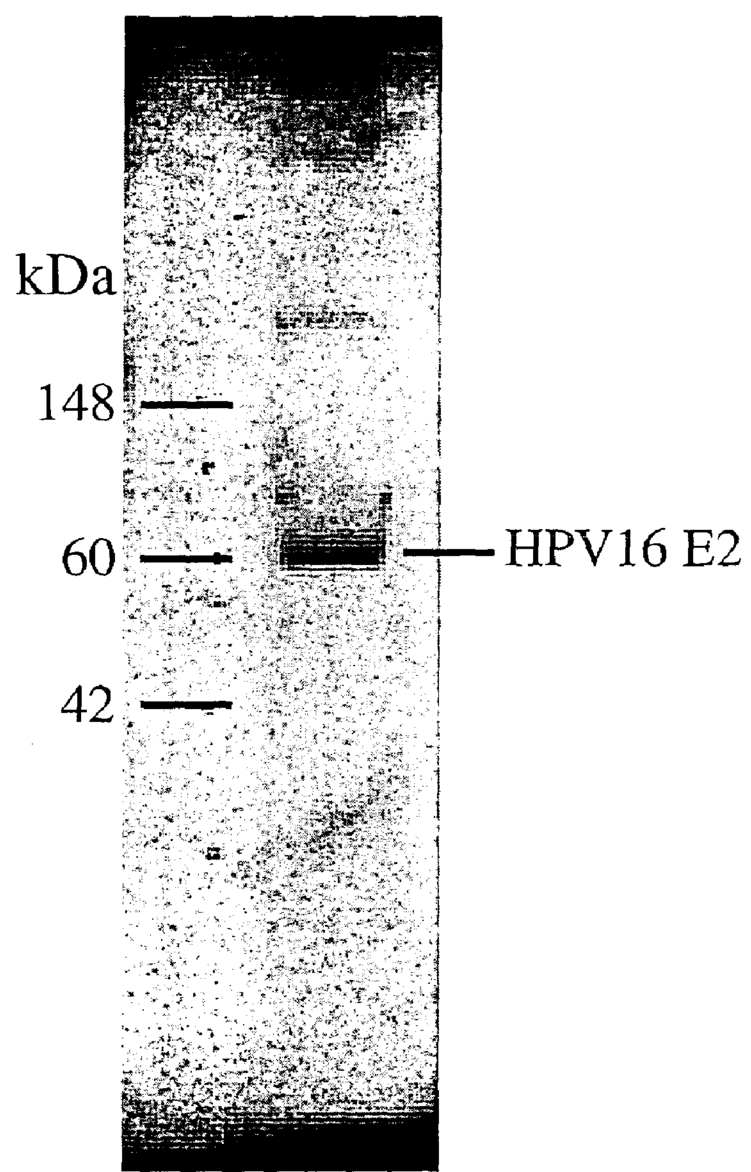

FIG. 25 is a Western blot of JCL-031 cell lysate. Cell lysate was prepared from JCL-031 cells grown in selection medium containing 400 $\mu$g/mL G418. The immunoblot was developed with anti-HPV 16 E2 (goat 248) antisera. Positions of molecular weight markers are indicated.

Figure 26:
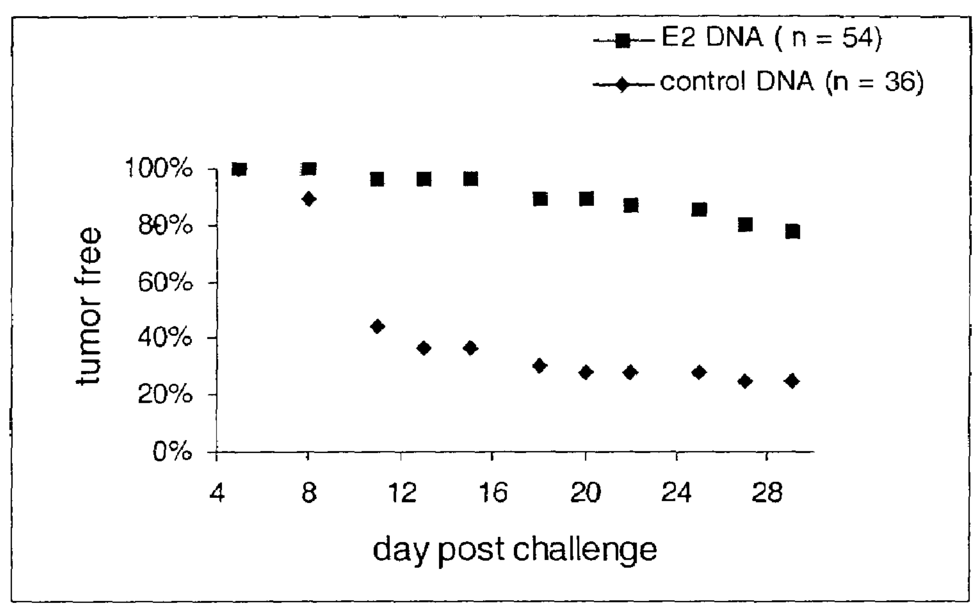

FIG. 26 shows protection from JCL-031 cell-induced tumor outgrowth. E2 DNA- or control DNA-immunized mice were challenged by subcutaneous injection of $5\times10^5$ JCL-031 cells into the left inguinal region. Beginning five days after this challenge, all animals were observed at two or three day intervals until four weeks after inoculation. Tumors were detected and monitored by visual inspection, palpation of the inguinal region, and measurement of tumor diameter with calipers.

The term "promoter" as used herein refers to a recognition site on a DNA strand to which the RNA polymerase binds. The promoter forms an initiation complex with RNA polymerase to initiate and drive transcriptional activity. The complex can be modified by activating sequences termed "enhancers" or inhibiting sequences termed "silencers".

The term "cassette" refers to the sequence of the present invention which contains the nucleic acid sequence which is to be expressed. The cassette is similar in concept to a cassette tape; each cassette has its own sequence. Thus by interchanging the cassette, the vector will express a different sequence. Because of the restrictions sites at the 5' and 3' ends, the cassette can be easily inserted, removed or replaced with another cassette.

The term "vector" refers to some means by which DNA fragments can be introduced into a host organism or host tissue. There are various types of vectors including plasmid, virus (including adenovirus), bacteriophages and cosmids.

The term "effective amount" means sufficient vaccine composition is introduced to produce the adequate levels of the polypeptide, so that an immune response results. One skilled in the art recognizes that this level may vary.

"Synthetic" means that the HPV gene has been modified so that it contains codons which are preferred for human expression. In many cases, the amino acids encoded by the gene remain the same. In some embodiments, the synthetic gene may encode a modified protein.

The term "native" means that the gene contains the DNA sequence as found in occurring in nature. It is a wild type sequence of viral origin.

DETAILED DESCRIPTION OF THE INVENTION

Synthetic DNA molecules encoding various HPV proteins are provided. The codons of the synthetic molecules are designed so as to use the codons preferred by the projected host cell, which is preferred embodiments is a human cell. The synthetic molecules may be used as a polynucleotide vaccine which provides effective immunoprophylaxis against papillomavirus infection through neutralizing antibody and cell-mediated immunity. The synthetic molecules may be used as an immunogenic composition. This invention provides polynucleotides which, when directly introduced into a vertebrate in vivo, including mammals such as primates and humans, induce the expression of encoded proteins within the animal.

The gene encoding a L1, E1, E2 and/or E7 from any serotype HPV can be modified in accordance with this invention. It is preferred that the HPV chosen be one which is known to cause a pathological condition in humans. For this reason, it is preferred that the HPV gene be selected from the group consisting of: HPV6a, HPV6b, HPV11, HPV16, HPV18, HPV31, HPV33, HPV35, HPV39, HPV45, HPV51, HPV52, HPV56, HPV58, HPV68 or variants thereof. The vaccine formulation of this invention may contain a mixture of HPV type protein genes (for example, genes from HPV6, 11, 16 and 18), and/or it may also contain a mixture of protein genes (i.e. L1, E1, E2, and/or E7).

Codon Optimization

The wild-type sequences for many HPV genes are known. In accordance with this invention, HPV gene segments were converted to sequences having identical translated sequences but with alternative codon usage as defined by Lathe, 1985 "Synthetic Oligonucleotide Probes Deduced from Amino Acid Sequence Data: Theoretical and Practical Considerations" *J. Molec. Biol.* 183:1–12, which is hereby incorporated by reference. The methodology may be summarized as follows:

1. Identify placement of codons for proper open reading frame.

2. Compare wild type codon for observed frequency of use by human genes.

3. If codon is not the most commonly employed, replace it with an optimal codon for high expression in human cells.

4. Repeat this procedure until the entire gene segment has been replaced.

5. Inspect new gene sequence for undesired sequences generated by these codon replacements (e.g., "ATTTA" sequences, inadvertent creation of intron splice recognition sites, unwanted restriction enzyme sites, etc.) and substitute codons that eliminate these sequences.

6. Assemble synthetic gene segments and test for improved expression.

In accordance with this invention, it has been found that the use of alternative codons encoding the same protein sequence may remove the constraints on expression of HPV proteins by human cells.

These methods were used to create the following synthetic gene segments for various papillomavirus genes creating a gene comprised entirely of codons optimized for high level expression. While the above procedure provides a summary of our methodology for designing codon-optimized genes for DNA vaccines, it is understood by one skilled in the art that similar vaccine efficacy or increased expression of genes may be achieved by minor variations in the procedure or by minor variations in the sequence.

In some embodiments of this invention, alterations have been made (particularly in the E-protein native protein sequences) to reduce or eliminate protein function while preserving immunogenicity. Mutations which decrease enzymatic function are known. Certain alterations were made for purposes of expanding safety margins and/or improving expression yield. These modifications are accomplished by a change in the codon selected to one that is more highly expressed in mammalian cells. In the case of HPV16 E1, for example two mutations were introduced: glycine at amino acid number 482 was changed to aspartic acid by conversion of GGC to GAC; and tryptophan was changed to arginine at position 439 by conversion of TGG to CGC.

For HPV16 E2, conversion of glutamic acid at position 39 to alanine and isoleucine at position 73 to alanine by conversion of both codons each to GCC.

For HPV16 E7, conversion of cysteine at position 24 to glycine and glutamic acid at position 26 to glycine was permitted by alteration of TGC and the GAG respectively both to GGC.

The codon-optimized genes are then assembled into an expression cassette which comprises sequences designed to provide for efficient expression of the protein in a human cell. The cassette preferably contains the codon-optimized gene, with related transcriptional and translations control sequences operatively linked to it, such as a promoter, and termination sequences. In a preferred embodiment, the promoter is the cytomegalovirus promoter with the intron A sequence (CMV-intA), although those skilled in the art will recognize that any of a number of other known promoters such as the strong immunoglobulin, or other eukaryotic gene promoters may be used. A preferred transcriptional terminator is the bovine growth hormone terminator, although other known transcriptional terminators may also be used. The combination of CMVintA-BGH terminator is particularly preferred.

Examples of preferred gene sequences are given in SEQ.ID.NOS: 1–8.

Vectors

In accordance with this invention, the expression cassette encoding at least one HPV protein is then inserted into a vector. The vector is preferably a plasmid or an adenoviral vector, although linear DNA linked to a promoter, or other vectors, such as adeno-associated virus or a modified vaccinia virus vector may also be used.

If the vector chosen is an adenovirus, it is preferred that the vector be a so-called first-generation adenoviral vector. These adenoviral vectors are characterized by having a non-functional E1 gene region, and preferably a deleted adenoviral E1 gene region. In some embodiments, the expression cassette is inserted in the position where the adenoviral E1 gene is normally located. In addition, these vectors optionally have a non-functional or deleted E3 region. The adenoviruses can be multiplied in known cell lines which express the viral E1 gene, such as 293 cells, or PerC.6 cells.

For convenience in manipulating the adenoviral vector, the adenovirus may be in a shuttle plasmid form. This invention is also directed to a shuttle plasmid vector which comprises a plasmid portion and an adenovirus portion, the adenovirus portion comprising an adenoviral genome which has a deleted E1 and optional E3 deletion, and has an inserted expression cassette comprising at least one codon-optimized HPV gene. In preferred embodiments, there is a restriction site flanking the adenoviral portion of the plasmid so that the adenoviral vector can easily be removed. The shuttle plasmid may be replicated in prokaryotic cells or eukaryotic cells.

Standard techniques of molecular biology for preparing and purifying DNA constructs enable the preparation of the adenoviruses, shuttle plasmids and DNA immunogens of this invention.

If the vector chosen is plasmid DNA, it is preferred that the vector contain one or more promoters recognized by mammalian or insect cells. In a preferred embodiment, the plasmid would contain a strong promoter such as, but not limited to the CMV promoter. The gene to be expressed would be linked to such a promoter. An example of such a plasmid would be the mammalian expression plasmid V1Jns as described (J. Shiver et. al. 1996, in *DNA Vaccines*, eds., M. Liu, et al. N.Y. Acad. Sci., N.Y., 772:198–208 and is herein incorporated by reference).

In some embodiment of this invention, the both the vaccine plasmid and the adenoviral vectors may be administered to a vertebrate in order to induce an immune response. In this case, the two vectors are administered in a "prime and boost" regimen. For example the first type of vector is administered, then after a predetermined amount of time, for example, 1 month, 2 months, six months, or other appropriate interval, a second type of vector is administered. Preferably the vectors carry expression cassettes encoding the same polynucleotide or combination of polynucleotides.

Thus, another aspect of this invention is a method for inducing an immune response against human papillomavirus in a vertebrate, comprising A) introducing into the vertebrate a first vector comprising a polynucleotide encoding an HPV protein selected from the group consisting of L1, E1, E2, and E7 proteins, wherein the polynucleotide is codon-optimized for expression in a human host cell;

B) allowing a predetermined amount of time to pass; and

C) introducing into the vertebrate a second vector comprising adenoviral vaccine vector comprising an adenoviral genome with a deletion in the E1 region, and an insert in the E1 region, wherein the insert comprises an expression cassette comprises i) a polynucleotide encoding an HPV protein selected from the group consisting of L1, E1, E2, and E7 proteins or mutant forms thereof, wherein the polynucleotide is codon-optimized for expression in a human host cell; and ii) a promoter operably linked to the polynucleotide.

In general, is preferred that the first vector be a plasmid vaccine vector and the second vector be an adenoviral vector. Thus this invention is directed to a method for inducing immune responses in a vertebrate comprising:

A) introducing into the vertebrate a plasmid vaccine, wherein the plasmid vaccine comprises a plasmid portion and an expression cassette portion, the expression cassette portion comprising:

i) a polynucleotide encoding an HPV protein selected from the group consisting of L1, E1, E2, and E7 proteins, wherein the polynucleotide is codon-optimized for expression in a human host cell; and ii) a promoter operably linked to the polynucleotide;

B) allowing a predetermined amount of time to pass; and

C) introducing into the vertebrate an adenoviral vaccine vector comprising an adenoviral genome with a deletion in the E1 region, and an insert in the E1 region, wherein the insert comprises an expression cassette comprising:

i) a polynucleotide encoding an HPV protein selected from the group consisting of L1, E1, E2, and E7 proteins or mutant forms thereof, wherein the polynucleotide is codon-optimized for expression in a human host cell; and ii) a promoter operably linked to the polynucleotide.

In yet another embodiment of the invention, the codon-optimized genes may be introduced into a recipient by way of a plasmid or adenoviral vector, as a "prime", and then a "boost" is accomplished by introducing into the recipient a polypeptide or protein which is essentially the same as that which is encoded by the codon-optimized gene. Fragments of a full length protein may be substituted, especially those which are immunogenic and/or include an epitope.

The amount of expressible DNA or transcribed RNA to be introduced into a vaccine recipient will depend partially on the strength of the transcriptional and translational promoters used and on the immunogenicity of the expressed gene product. In general, an immunologically or prophylactically effective dose of about 1 ng to 100 mg, and preferably about 10 $\mu$g to 300 $\mu$g of a plasmid vaccine vector is administered directly into muscle tissue. An effective dose for recombinant adenovirus is approximately $10^6$–$10^{12}$ particles and preferably about $10^7$–$10^{11}$ particles. Subcutaneous injection, intradermal introduction, impression through the skin, and other modes of administration such as intraperitoneal, intravenous, or inhalation delivery are also contemplated. It is also contemplated that booster vaccinations may be provided. Parenteral administration, such as intravenous, intramuscular, subcutaneous or other means of administration with adjuvants such as interleukin-12 protein, concurrently with or subsequent to parenteral introduction of the vaccine of this invention is also advantageous.

The vaccine vectors of this invention may be naked, that is, unassociated with any proteins, adjuvants or other agents which impact on the recipients' immune system. In this case, it is desirable for the vaccine vectors to be in a physiologically acceptable solution, such as, but not limited to, sterile saline or sterile buffered saline or the DNA may be associated with an adjuvant known in the art to boost immune responses, such as a protein or other carrier. Agents which assist in the cellular uptake of DNA, such as, but not limited to, calcium ions, may also be used to advantage. These agents are generally referred to herein as transfection facilitating reagents and pharmaceutically acceptable carriers. Techniques for coating microprojectiles coated with polynucleotide are known in the art and are also useful in connection with this invention.

The following examples are offered by way of illustration and are not intended to limit the invention in any manner.

EXAMPLES

Example 1

Synthetic Gene Construction

Synthetic gene sequences for human papillomavirus proteins L1, E1, E2, and E7 were generated by reverse translation of amino acid sequences using the most frequently used codons found in highly expressed mammalian genes. (R. Lathe, 1985, *J. Mol. Biol.* 183:1–12, which is hereby incorporated by reference). Some adjustments to these codon-optimized sequences were made to introduce or remove restriction sites. Oligonucleotides based on these sequences were chemically synthesized (Midland Certified Reagents; Midland, Tex.) and assembled by PCR amplification. (J. Haas et. al., 1996, *Current Biology* 6:315–324; and *PCR Protocols*, M. Innis, et al, eds., Academic Press, 1990, both of which are hereby incorporated by reference).

Full-length sequences were cloned into the mammalian expression vector V1Jns (J. Shiver et. al. 1996, in *DNA Vaccines*, eds., M. Liu, et al. N.Y. Acad. Sci., N.Y., 772: 198–208, which is hereby incorporated by reference) and sequenced by standard methodology. In cases where the actual sequence differed from the expected and resulted in amino acid substitution, that sequence was corrected by PCR mutagenesis as previously described (*PCR Protocols*, M. Innis, et al, eds., Academic Press, 1990, pg 177–180).

Protein expression was evaluated by transient transfection of equal quantities of plasmid DNA into 293 (transformed embryonic human kidney) cells which were harvested at 48 hr post DNA addition. Cell lysates were normalized to provide equal protein loadings. Analysis was by indirect immunofluorescence or immunoblot (Western) analysis using sera prepared to each of the HPV proteins. (Current Protocols in Molecular Biology, eds., F. Ausabel, et. Al., John Wiley and Sons, 1998, which is hereby incorporated by reference).

Example 2

Synthesis of HPV 16 L1

The gene encoding HPV16 L1 was prepared by the annealing and extension of the 14 oligomers listed in FIG. 17. Five separate extension reactions were performed to create fragments of the gene, designated L1A, L1B, L1C, L1D and L1E by PCR using conditions similar to those described in EXAMPLE 3 and 4, below.

L1A was constructed using oligomer sequences MN4A1 (SEQ.ID.NO:9), MN4A2 (SEQ.ID.NO:16) and MN4A3 (SEQ.ID.NO:10) which were amplified using the oligomers MN604 (SEQ.ID.NO:32) and MN596 (SEQ.ID.NO:24).

L1B was constructed using oligomer sequences MN4A4 (SEQ.ID.NO:17), MN4A5 (SEQ.ID.NO:11) and MN4A6 (SEQ.ID.NO:18) and were amplified using the oligomers MN595 (SEQ.ID.NO:23) and MN598 (SEQ.ID.NO:26).

L1C was created using oligomer sequences MN4A7 (SEQ.ID.NO:12) and MN4A8 (SEQ.ID.NO:19) and were amplified using the oligomers MN597 (SEQ.ID.NO:25) and MN602 (SEQ.ID.NO:30).

L1D was created using oligomer sequences MN4A9 (SEQ.ID.NO:13), MN4A10 (SEQ.ID.NO:20) and MN4A II (SEQ.ID.NO:14) which were amplified using the oligomers MN597 (SEQ.ID.NO:25) and MN602 (SEQ.ID.NO:30).

L1E was created using oligomer sequences MN4A12 (SEQ.ID.NO:21), MN4A13 (SEQ.ID.NO:15) and MN4A14 (SEQ.ID.NO:22) which were amplified using the oligomers MN601 (SEQ.ID.NO:29) and MN603 (SEQ.ID.NO:31).

Fragments L1A, L1B, L1C, L1D and L1E resulting from the PCR reactions were gel separated on low melting point agarose with the appropriately-sized products excised and purified using the Agarase™ method (Boehringer Mannheim Biochemicals) as recommended by the manufacturer. Fragments L1A, L1B and L1C were combined in a subsequent PCR reaction using oligomers MN604 (SEQ.ID.NO:32) and MN600 (SEQ.ID.NO:28) to assemble L1A-B-C; fragments L1D and L1E were assembled to L1D-E by subsequent PCR with the oligomers MN599 (SEQ.ID.NO:27) and MN603 (SEQ.ID.NO:31). The complete gene was then assembled by additional PCR reactions in which fragments L1A-B-C, L1D-E were combined with oligomers MN604 (SEQ.ID.NO:32) and MN603 (SEQ.ID.NO:31) in a final series of PCR reactions. The resulting 1.5 kb product was gel isolated, digested with Bgl II and subcloned into the V1Jns and sequenced. In instances where a mutation was observed, it was corrected by PCR mutagenesis as described in EXAMPLE 1. DNA was isolated from a clone with the correct HPV16 L1 DNA sequence and proper orientation within V1Jns for use in transient transfection assays as described in EXAMPLE 1.

Transfection Results (HPV16 L1)

Figure 9:
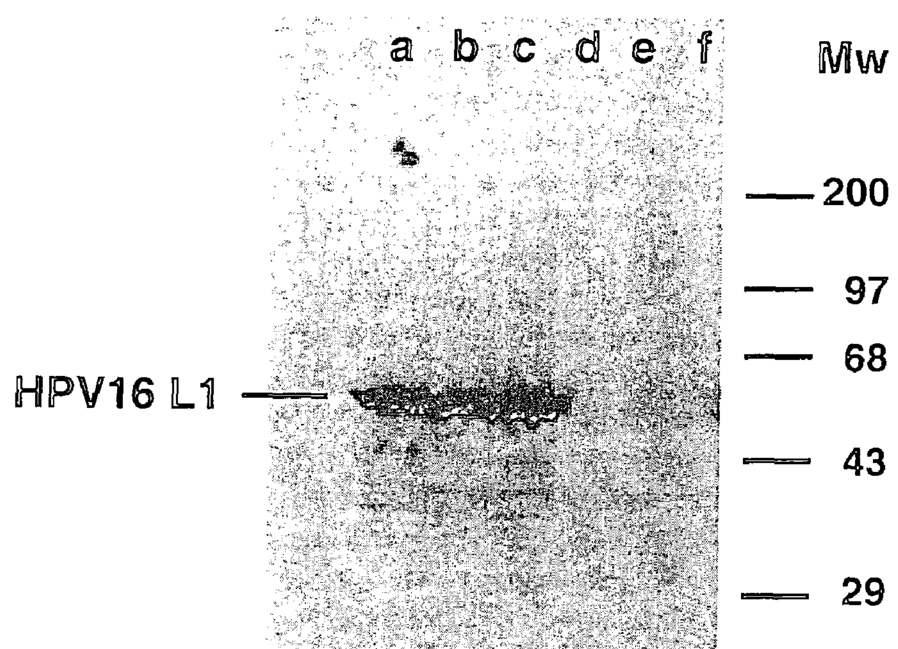
FIG. 9 shows the results of immunoblot analysis of lysates of 293 cells transiently-transfected with native (lanes d, e, f) or synthetic (a, b, c) HPV16 L1 sequences in the expression vector V1Jns.

FIG. 9 shows the HPV16 L1 immunoblot results of lysates of 293 cells transiently-transfected with the V1Jns plasmid containing either the native or the codon-optimized, synthetic HPV16 L1. Lanes a, b and c are the expression levels achieved using the synthetic HPV16 L1 expression construct. High levels of immunoreactive material are apparent in each of these lanes with the predominant band at approximately 55 kDa, consistent with the expected molecular weight for full-length HPV16 L1. In contrast, virtually no immunoreactive material is apparent in the lanes containing lysates transfected with the native HPV16 L1/V1Jns plasmid (lanes d, e, and f). Since all cell lysate loadings were normalized and equivalent DNA amounts were used in the transfections, these findings indicate that the synthetic gene sequence greatly increased the levels of HPV16 L1 protein accumulation relative to that of the native gene sequence.

Example 3

Synthesis of HPV 16 E1

The gene encoding the modified form of HPV16 E1 was assembled from a series of fragments: E1A, E1B, E1C, E1D, E1E and E1F, using the oligomers listed in FIG. 18. E1A was formed by assembly of oligomers MN605 (SEQ.ID.NO:33), MN606 (SEQ.ID.NO:34) and MN607 (SEQ.ID.NO:35) and amplified using oligomers MN636 (SEQ.ID.NO:64) and MN624 (SEQ.ID.NO:52).

E1B was formed by assembly of oligomers MN608 (SEQ.ID.NO:36), MN609 (SEQ.ID.NO:37) and MN610 (SEQ.ID.NO:38) which were amplified with oligomers MN623 (SEQ.ID.NO:51) and MN626 (SEQ.ID.NO:54).

E1C was formed by assembly of oligomers MN611 (SEQ.ID.NO:39) and MN612 (SEQ.ID.NO:40) which were amplified with oligomers MN625 (SEQ.ID.NO:53) and MN628 (SEQ.ID.NO:56).

E1D was formed by assembly of oligomers MN613 (SEQ.ID.NO:41), MN614 (SEQ.ID.NO:42) and MN615 (SEQ.ID.NO:43) which were amplified with oligomers MN627 (SEQ.ID.NO:55) and MN630 (SEQ.ID.NO:58).

E1E was formed by assembly of oligomers MN616 (SEQ.ID.NO:44), MN617 (SEQ.ID.NO:45) and MN618 (SEQ.ID.NO:46) which were amplified with oligomers MN629 (SEQ.ID.NO:57) and MN632 (SEQ.ID.NO:60).

E1F was formed by assembly of oligomers MN619 (SEQ.ID.NO:47), MN620 (SEQ.ID.NO:48) and MN621 (SEQ.ID.NO:49) which were amplified with oligomers MN631 (SEQ.ID.NO:59) and MN635 (SEQ.ID.NO:63).

Products of these PCR reactions were gel isolated and combined in subsequent rounds of PCR to form a 2 kb gene fragment encoding HPV16 E1 using methods described above. The resulting HPV16 E1 was inserted into the V1Jns expression vector as above and utilized in transient transfection studies as described in EXAMPLE 1.

Transfection Results (HPV16 E1)

Figure 10:
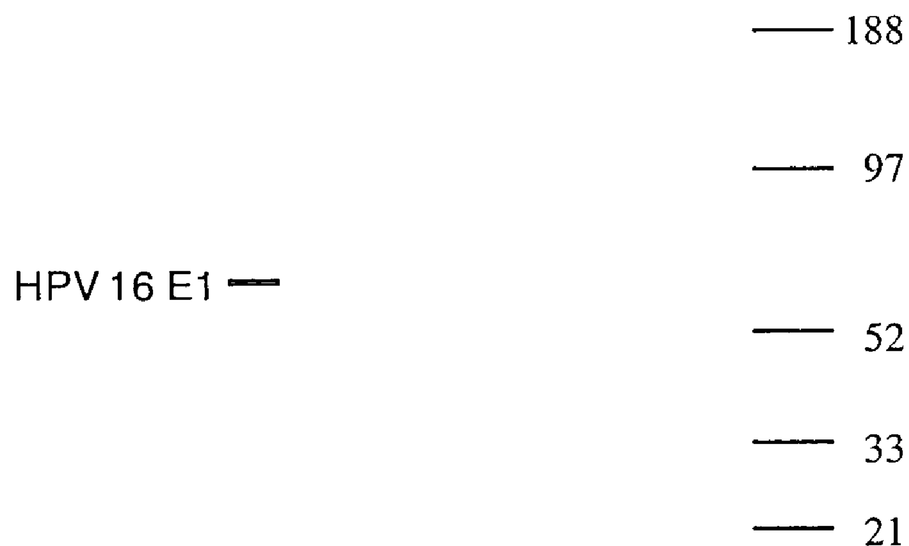
FIG. 10 shows the results of immunoblot analysis of lysates of 293 cells transiently-transfected with native or synthetic HPV16 E1 sequences in the expression vector V1Jns. Lanes a and d contain native HPV16 E1 sequences; lanes b and e contain synthetic HPV16 E1, and lane c is a mock-transfected control.

FIG. 10 shows the HPV16 $\mu l$ immunoblot results of lysates of 293 cells transiently-transfected with the V1Jns plasmid containing either the native, or the codon-optimized, synthetic HPV16 E1. Lanes b and e are the expression levels achieved using the codon-optimized HPV16 E1 expression construct. High levels of HPV16 E1-specific immunostaining are apparent with a predominant band in lanes b and eat 72 kDa, consistent with the expected size for full-length HPV16 $\mu l$. In addition, there a number of smaller immunoreactive products which appear to be E1-specific as they are not observed in the mock transfected control (lane c).

A very different expression profile is observed in lysates of cells transfected with the native HPV16 E1/V1Jns construct, however. As shown in lanes a and d, only minimal amounts of immunoreactive material can be visualized which is not present in the mock transfection control. Since all cell lysate loadings were normalized and equivalent DNA amounts were used in the transfections these findings indicate that the synthetic gene sequence greatly increased the levels of HPV16 E1 protein accumulation relative to that of the native gene sequence.

Example 4

Synthesis of HPV 16 E2

Fragment AD. A 50 μl reaction containing oligonucleotides 13856-307-2A (SEQ.ID.NO:65), 13856-307-2B (SEQ.ID.NO:71), 13856-307-2C (SEQ.ID.NO:66), and 13856-307-2D (SEQ.ID.NO:72), at 150 nM each, dNTPs 0.5 mM each, Native buffer (Stratagene; La Jolla, Calif.) and 1 μL Native Pfu DNA polymerase (Stratagene) was incubated in a GeneAmp 9700 thermocycler (Perkin Elmer Applied Biosystems; Foster City, Calif.) under the following conditions: 95° C., 2 min.; 20 cycles of 95° C., 45 sec.; 55° C., 45 sec.; and 72° C., 2.5 min. Added to the reaction were primers 13856-307-2PA (SEQ.ID.NO:78) and 13856-307-2PD (SEQ.ID.NO:82) to a final concentration of 400 nM each, and 1 μL of Native Pfu DNA polymerase. The mixture was incubated for 2 min at 95° C. and then 25 cycles of 95° C., 45 sec; 55° C., 45 sec; and 72° C., 2.5 min. The gel-isolated full-length fragment AD was amplified for 20 cycles under the same conditions using primers 13856-307-2PA (SEQ.ID.NO:78) and 13856-307-2PD (SEQ.ID.NO:82).

Fragment EH. A 50 μl reaction containing oligonucleotides 13856-307-2E (SEQ.ID.NO:67), 13856-307-2F (SEQ.ID.NO:73), 13856-307-2G (SEQ.ID.NO:68), and 13856-307-2H (SEQ.ID.NO:74) at 150 nM each, dNTPs 0.5 mM each, Native buffer and 1 μL Native Pfu DNA polymerase was incubated under the following conditions: 95° C., 2 min; 20 cycles of 95° C., 2 min.; 45 sec.; 55° C., 45 sec.; and 72° C., 2.5 min. Added to the reaction were primers 13856-307-2PE (SEQ.ID.NO:80) and 13856-307-2PH (SEQ.ID.NO:83) to a final concentration of 400 nM each, and 1 μL of Native Pfu DNA polymerase. The mixture was incubated for 95° C., 2 min.; then 25 cycles of 95° C., 45 sec.; 55° C., 45 sec.; and 72° C., 2.5 min.

Fragment IL. A 50 μl reaction containing oligonucleotides 13856-307-21 (SEQ.ID.NO:69), 13856-307-2J (SEQ.ID.NO:75), 13856-307-2K (SEQ.ID.NO:70), and 13856-307-2L (SEQ.ID.NO:76) at 150 nM each, dNTPs 0.5 mM each, Native buffer and 1 μL Native Pfu DNA polymerase was incubated under the following conditions: 95° C., 2 min; 20 cycles of 95° C., 2 min.; 45 sec.; 55° C., 45 sec.; and 72° C., 2.5 min. Added to the reaction were primers 13856-307-2PI (SEQ.ID.NO:81) and 13856-307-2PL (SEQ.ID.NO.84) to a final concentration of 400 nM each, and 1 μL of Native Pfu DNA polymerase. The mixture was incubated at 95° C., 2 min.; then 25 cycles of 95° C., 45 sec.; 55° C., 45 sec.; and 72° C., 2.5 min.

Fragment AH. A 50 μl reaction containing 1.5 μl each of AD and EH PCR products, dNTPs 0.5 mM each, Native buffer and 1 μL Native Pfu DNA polymerase was incubated under the following conditions: 95° C., 2 min; 20 cycles of 95° C., 45 sec.; 55° C., 45 sec.; and 72° C., 3.5 min. Added to the reaction were primers 13856-307-2PA (SEQ.ID.NO:78) and 13856-307-2PH (SEQ.ID.NO:83) to a final concentration of 400 nM each, and 1 μL of Native Pfu DNA polymerase. The mixture was incubated at 95° C., 2 min.; then 25 cycles of 95° C., 45 sec.; 55° C., 45 sec.; and 72° C., 3.5 min.

Fragment IM. A 50 μl reaction containing 1 μl of IL PCR product, oligonucleotides 13856-307-2M (SEQ.ID.NO:77) and 13856-307-2PI (SEQ.ID.NO:81) each at a final concentration of 400 nM, dNTPs 0.5 mM each, Native buffer and 1 μL Native Pfu DNA polymerase was incubated under the following conditions: 95° C., 2 min; 25 cycles of 95° C., 45 sec.; 55° C., 45 sec.; and 72° C., 4 min.

Assembly of AM, full-length HPV16 E2. A 50 μl reaction containing 1.5 μl each of fragments AH and IM, dNTPs 0.5 mM each, Native buffer and 1 μL Native Pfu DNA polymerase was incubated under the following conditions: 95° C., 2 min; 20 cycles of 95° C., 45 sec.; 55° C., 45 sec.; and 72° C., 4 min. Added to the reaction were primers 13856-307-2PA (SEQ.ID.NO:78) and 13856-307-2PM (SEQ.ID.NO:79) at a final concentration of 400 μM each, and 1 μL of Native Pfu DNA polymerase. The mixture was incubated at 95° C., 2 min.; then 25 cycles of 95° C., 45 sec.; 55° C., 45 sec.; and 72° C., 4 min. The resultant full-length fragment was isolated by electrophoresis through a 1.2% agarose gel the DNA recovered with a QIAquick column (Qiagen; Santa Clarita, Calif.) and subcloned into the expression vector V1Jns for evaluation.

Transfection Results (HPV16 E2)

Figure 11:
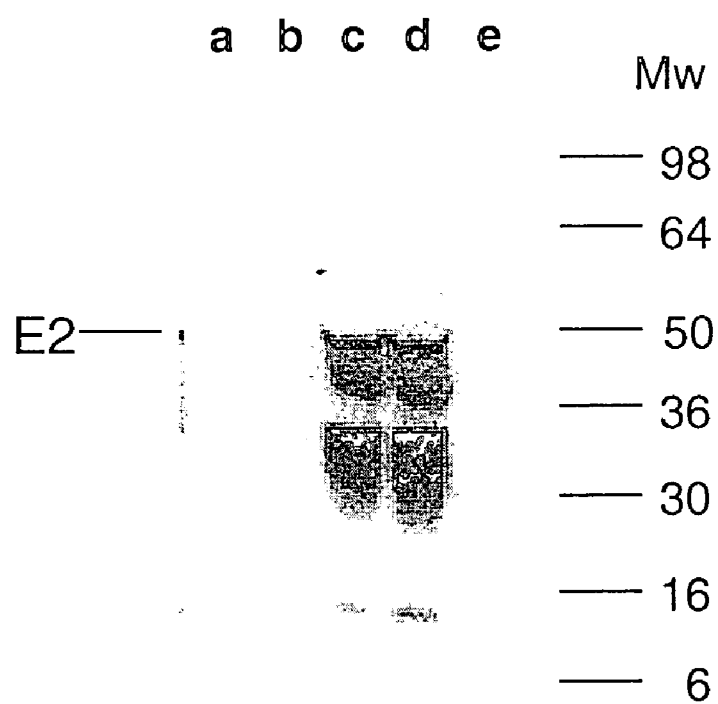
FIG. 11 shows the results of immunoblot analysis of lysates of 293 cells transiently-transfected with native or synthetic HPV16 E2 sequences in the expression vector V1Jns. Lane a is mock-infected; lane b is lacZ control; lane c contains a synthetic HPV16 E2 isolate #6; lane d contains synthetic HPV16 E2 isolate #11, and lane e has native HPV16 E2.

FIG. 11 shows the HPV16 E2 immunoblot results of lysates of 293 cells transiently-transfected with the V1Jns plasmid containing either the native, or the synthetic HPV16 E2. Lanes c and d are the expression levels achieved using the codon-optimized HPV16 E2 expression construct. High levels of HPV16 E2-specific immunostaining are visible which appear to be E2-specific as they are not observed in the mock transfected control (lane c).

A very different expression profile is observed in lysates of cells transfected with the native HPV16 E2/V1Jns construct, however. As shown in lane e, no immunoreactive material can be visualized. Since all cell lysate loadings were normalized and equivalent DNA amounts were used in the transfections, these findings indicate that the synthetic gene sequence greatly increased the levels of HPV16 E2 protein accumulation relative to those of the native gene sequence.

Example 5

Synthesis of HPV 16 E7

The gene encoding HPV16 E7 was assembled from a series of fragments, made using oligomers listed in FIG. 20.

A 50 μl reaction containing oligonucleotides 13856-307-7A (SEQ.ID.NO:85), 13856-307-7B (SEQ.ID.NO:87), 13856-307-7C (SEQ.ID.NO:86), and 13856-307-7D (SEQ.ID.NO:88) at 150 nM each, dNTPs 0.5 mM each, Native buffer (Stratagene; La Jolla, Calif.) and 1 μL Native Pfu DNA polymerase (Stratagene) was incubated in a GeneAmp 9700 thermocycler (Perkin Elmer Applied Biosystems; Foster City, Calif.) under the following conditions: 95° C., 2 min; 20 cycles of 95° C., 45 sec.; 55° C., 45 sec. and 72° C., 2.5 min. Added to the reaction were primers 13856-307-7PA (SEQ.ID.NO:89) and 13856-307-7PD (SEQ.ID.NO:90) to a final concentration of 400 nM), and 1 μL of Native Pfu DNA polymerase. The mixture was incubated for 25 cycles of 95° C., 45 sec.; 55° C., 45 sec. and 72° C., 2.5 min.

The resultant full-length fragment was isolated by electrophoresis through a 1.2% agarose gel in TBE (Current Protocols in Molecular Biology, eds., F. Ausabel, et. al., John Wiley and Sons, 1998, which is hereby incorporated by reference), stained with ethidium bromide, cut from the gel and recovered through a GenElute column (Supleco; Bellefonte, Pa.) and resuspended in 20 μl water. The sequence was further amplified in a 51 μl reaction containing 2 μl of fragment, 0.5 μM each of oligonucleotides 13856-307-7PA (SEQ.ID.NO:89) and 13856-307-7PD, (SEQ.ID.NO:90) dNTPs 0.5 mM each, Native buffer and Native Pfu DNA polymerase. The reaction was subjected to 20 cycles of 95°

C., 45 sec.; 55° C., 45 sec. and 72° C., 2.5 min. The final amplified product isolated by electrophoresis as described above; the DNA recovered with a QIAquick column (Qiagen; Santa Clarita, Calif.) and subcloned into V1Jns.

Transfection Results (HPV16 E7)

Figure 12:
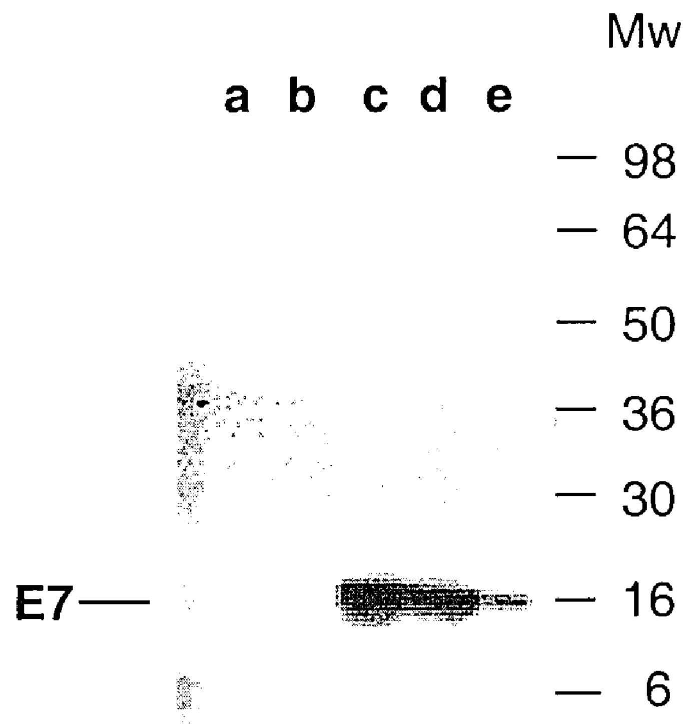
FIG. 12 shows the results of immunoblot analysis of lysates of 293 cells transiently-transfected with native or synthetic HPV16 E7 sequences in the expression vector V1Jns. Lane a is mock-infected; lane b is lacZ control; lane c contains synthetic HPV16 E7 isolate #2; lane d is synthetic HPV16 E7 isolate 4; and lane e is native HPV16 E7.

FIG. 12 shows the HPV16 E7 immunoblot results of lysates of 293 cells transiently-transfected with the V1Jns plasmid containing either the native (lane e) or synthetic HPV16 E7 (lanes c and d). High levels of HPV16 E7-specific immunostaining are visible in the synthetic HPV16 E7 gene cell lysate lanes which are considerably more intense in appearance than that of the native HPV16 E7 gene cell lysate (lane e). Lanes a and b are negative transfection controls which show the antibody staining is specific to HPV16 E7 sequences. Since all cell lysate loadings were normalized and equivalent DNA amounts were used in the transfections, these findings indicate that the synthetic gene sequence greatly increased the levels of HPV16 E2 protein accumulation relative to those of the native gene sequence.

Example 6

Synthesis of the E7 and E2-Encoding Genes from HPV6a and HPV18

The genes encoding HPV6a E7 and HPV 18 E7 were constructed using similar methods as described in EXAMPLE 4, except that the oligomers used to create the HPV6a E7 and HPV 18 E7 genes contain the sequences listed in FIG. 21 and FIG. 22, respectively. The construction of the synthetic genes encoding HPV6a E2 and HPV18 E2 was performed in a similar manner as detailed in EXAMPLE 5 using the oligomer sequences listed in FIG. 23 and FIG. 24 respectively.

Transfection Results: HPV6a E7 and HPV 18 E7

Figure 13:
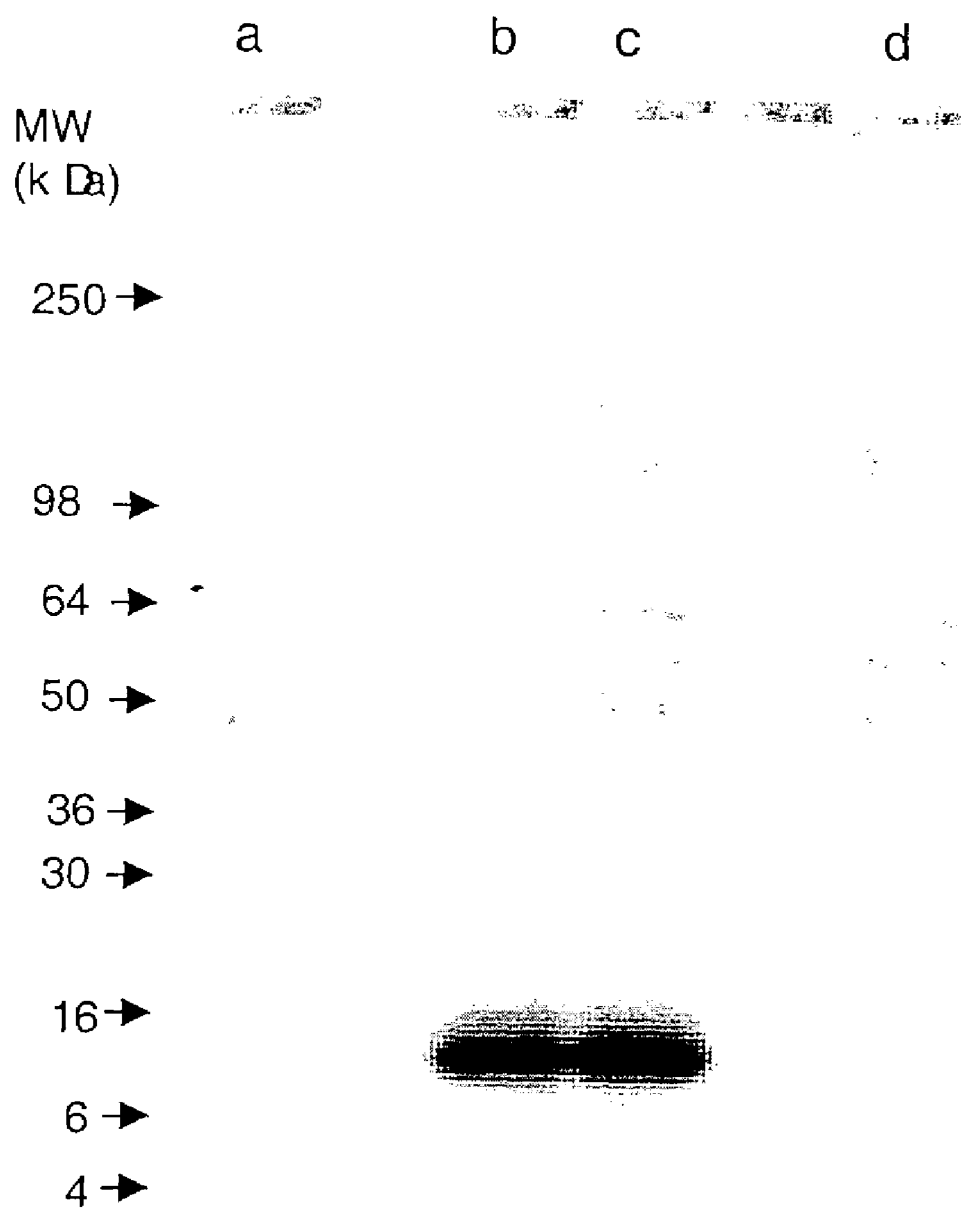
FIG. 13 shows the results of immunoblot analysis of lysates of 293 cells transiently-transfected with synthetic HPV6a E7 sequences in the expression vector V1Jns. Lanes b and c contain synthetic HPV6a E7 sequences; lane d contains a lacZ control, and lane a is a mock-transfected control.
Figure 14:
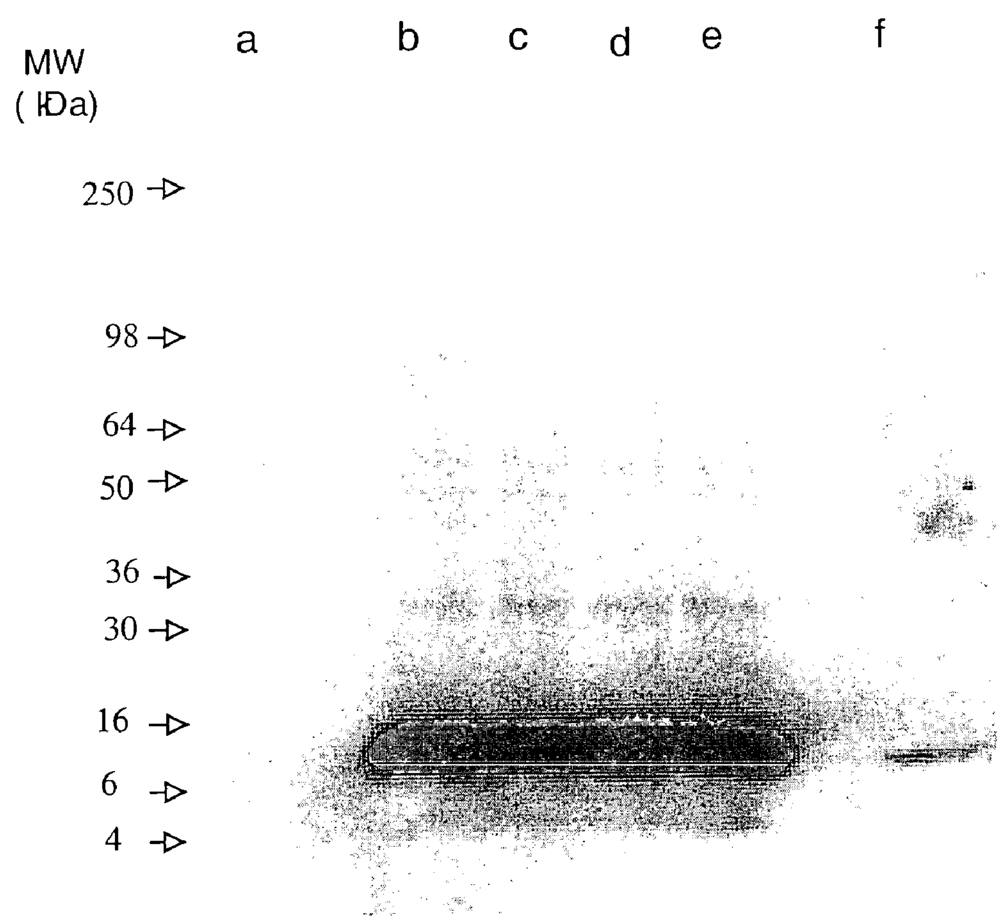
FIG. 14 shows the results of immunoblot analysis of lysates of 293 cells transiently-transfected with synthetic HPV18 E7 sequences in the expression vector V1Jns. Lanes b, c, d, and e contain synthetic HPV18 E7 sequences; lane f contains synthetic HPV16 E7 as an antibody control, and lane a is a mock-transfected control.

FIG. 13 shows the HPV6a E7 immunoblot results of lysates of 293 cells transiently-transfected with the V1Jns plasmid containing synthetic HPV6a E7 (lanes b and c). High levels of HPV6a E7-specific immunostaining are visible in the region expected for full-length HPV6a E7. A similar profile is found in FIG. 14 by HPV18 E7 immunoblot analysis of lysates of 293 cells transiently-transfected with the V1Jns plasmid containing synthetic HPV6a E7 (lanes b, c, d and e). High levels of HPV18 E7-specific immunostaining are visible where full-length HPV18 E7 would be found as indicated by the location of the purified HPV18 protein control (lane f). There does not appear to be any stained material in the negative control lane a which indicates the staining in the other lanes is HPV18 E7-specific.

Figure 15:
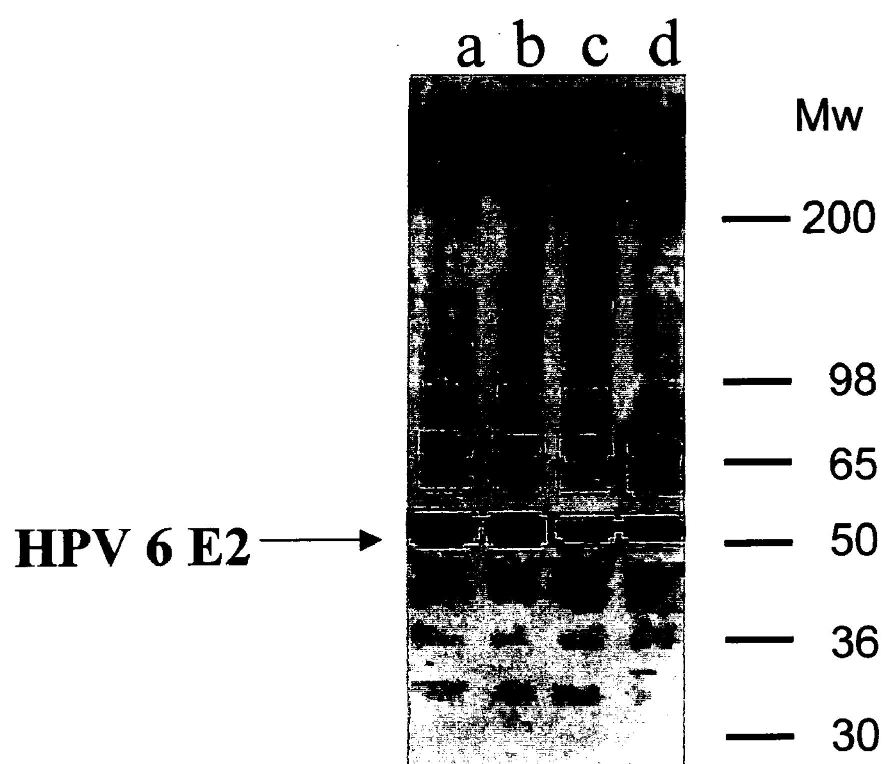
FIG. 15 shows the results of immunoblot analysis of lysates of 293 cells transiently-transfected with synthetic HPV6a E2 sequences in the expression vector V1Jns. Lanes a and b contain synthetic E2 sequences; lane c is a beta-gal control, and lane d is mock-transfected.
Figure 16:
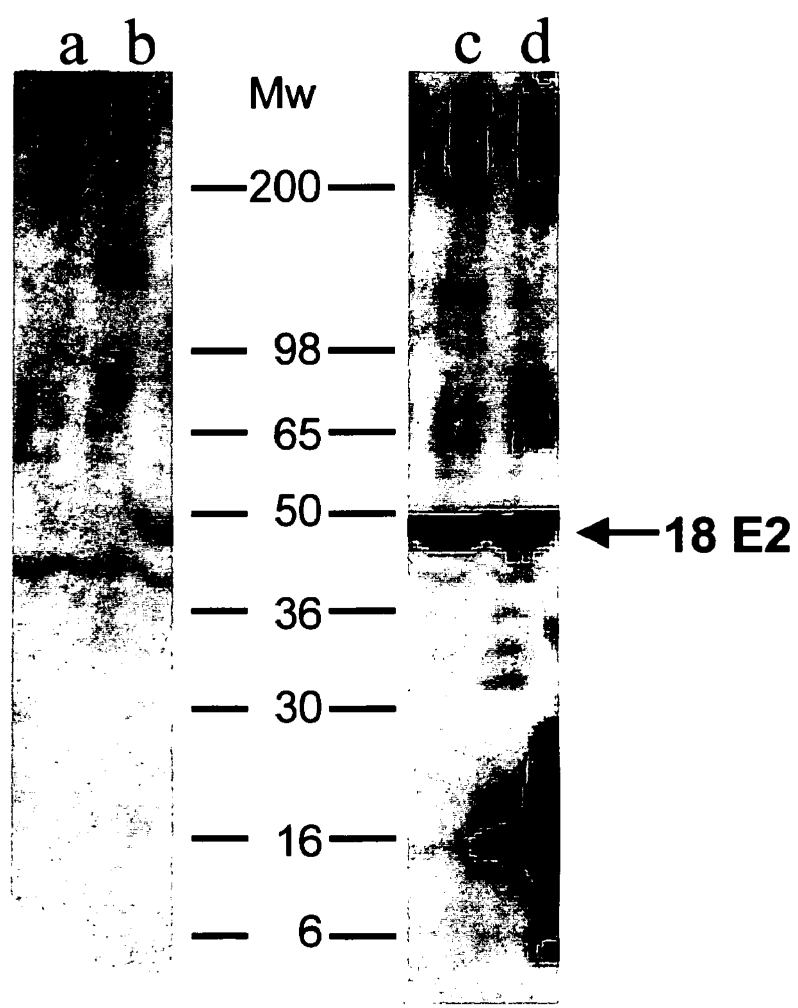
FIG. 16 shows the results of immunoblot analysis of lysates of 293 cells transiently-transfected with synthetic HPV18 E2 sequences in the expression vector V1Jns. Lane a is beta-gal control; lane b is mock transfected; and lanes c and d have synthetic sequences.

Expression of the synthetic gene encoding HPV6a E2 in V1Jns was evaluated by immunoblot analysis of transfected 293 cells which is shown in FIG. 15. Lanes a and b are cell lysates of the synthetic HPV6a E2 transfectants; lanes c and d are negative controls. The analogous experiment is shown for HPV18 E2 expression in FIG. 16. Lanes c and d are the cell lysates of transfections receiving the synthetic HPV18 E2 gene; lanes a and b are the negative controls. Both of these figures show measurable levels of E2 product accumulation when the codon-optimized, synthetic gene is expressed in mammalian cells.

These results indicate that the synthetic gene rebuilding is not limited to HPV16 genes. Rather, codon optimization of other HPV types also permits significant levels of E7 and E2 product accumulation in mammalian cells.

Example 7

Construction of Replication-defective FG-Ad Expressing HPV Antigen

Starting Vectors

Shuttle vector pHCMVIBGHpA1 contains Ad5 sequences from bp1 to bp 341 and bp 3534 to bp 5798 with a expression cassette containing human cytomegalovirus (HCMV) promoter plus intron A and bovine growth hormone polyadenylation signal.

The adenoviral backbone vector pAdE1-E3- (also named as pHVad1) contains all Ad5 sequences except those nucleotides encompassing the E1 and E3 region.

Construction of Ad5. HPV16 E2

1. Construction of adenoviral shuttle plasmid pA1-CMVI-HPV16 E2 containing HPV 16 E2 under the control of human CMV promoter and intron A.

The HPV16 E2 insert was excised from pV1JNS-HPV16 E2 by restriction enzyme Bgl II, EcoRI and then cloned into Bgl II, EcoRI digested shuttle vector pHCMVIBGHpA1.

2. Homologous recombination to generate plasmid form of recombinant adenoviral vector pAd-CMVI-HPV16 E2 containing HPV16 E2 expression cassette.

Shuttle plasmid pA1-CMVI-HPV 16 E2 was digested with restriction enzymes BstZ17 and SgrA1 and then co-transformed into *E. coli* strain BJ5183 with linearized (ClaI digested) adenoviral backbone plasmid pAdE1-E3-. A colony was verified by PCR analysis. The vector was transformed to competent *E. coli* HB 101 for large quantity production of the plasmid.

3. Generation of recombinant adenovirus Ad.CMVI—HPV16 E2 in 293 cells.

The pAd plasmid was linearized by restriction enzyme PacI and transfected to 293 cells using CaPO4 method (Invitrogen kit). Ten days later, 10 plaques were picked and grown in 293 cells in 35-mm plates. PCR analysis of the adenoviral DNA showed virus were positive for HPV16 E2.

4. Evaluation of Large Scale Recombinant Adenovirus Ad.CMVI—HPV 16 E2

A selected clone was grown into large quantities through multiple rounds of amplification in 293 cells. Expression of HPV16 E2 was also verified by ELISA and Western blot analysis of the 293 or COS cells infected with the recombinant adenovirus. The recombinant adenovirus was used for evaluation in mice and rhesus monkeys.

Method of Treatment

A person in need of therapeutic or prophylactic immunization against infection with human papillomavirus virus is injected with HPV DNA encoding all or part of; HPV L1, E1, E2, E4 or E7 and combinations thereof. The injection may be i.p., subcutaneous, intramuscular or intradermal. The HPV DNA may be used as a primer of the immune response or may be used as a booster of the immune response. The injection of DNA may antedate, coincide or follow injection of the person with a pharmaceutical composition comprising HPV virus like particles (containing only L1 protein or containing both L1 and L2 proteins, or containing mutant forms of one or more proteins), capsomeres, inactivated HPV, attenuated HPV, compositions comprising HPV-derived proteins, or combinations thereof.

Example 8

The Use of a Synthetically-expressed HPV E Protein as a Model Tumor Antigen

Generation of a tumor cell line that expresses HPV 16 E2.

A Not I-Hind III restriction digest fragment containing the synthetic coding sequence for HPV 16 E2 (see above) was ligated with Not I, Hind III digested expression vector pBJ/neo/CCR2B which has a neomycin resistance marker and drives the expression of the transgene with the HCMV immediate early promoter. The resultant plasmid, pBJ-16 E2, was characterized by restriction digestion, sequence analysis of the cloning junctions, and the ability to induce E2 protein expression in transiently-transfected A293 or CT26 cells. A stable cell line was generated transfection of CT26 cells using Lipofectamine (Gibco BRL). CT26 cells, a fully-transformed line derived from a BALB/c mouse colon carcinoma, have been widely used to present model tumor antigens. (Brattain et al., 1980 *Cancer Research* 40:2142–2146; Fearon, E. et al.,1988 *Cancer Research,* 48:2975–2980; both of which are incorporated by reference).

After 48 hours, cells were trypsinized, diluted 1:10, 1:100, 1:1000 or 1:10000 into medium and plated in 100 $mm^2$ plates. After 24 hours, the medium was replaced with selection medium containing 400 μg/mL G418. After two to three weeks, well-isolated colonies of cells were recovered using cloning rings and transferred to 48-well plates. One clone was positive for E2 expression by immunoblot analysis and was subjected to two further rounds of cloning by limiting dilution. One G418 resistant, E2-positive clonal isolate was used to established the cell line JCL-031. (FIG. 25).

When inoculated into (syngeneic) BALB/c mice by subcutaneous injection, JCL-031 cell induced tumors with the kinetics similar to those as the parental CT26 line. Cells cultured from recovered tumors were G418 resistant and expressed E2.

Induction of immunity in mice by immunization with V1Jns: E2 DNA.

BALB/c mice were immunized multiple times by intramuscular injection with the DNA V1Jns:16E2. Spleens from two randomly-chosen mice in each dose group were pooled, splenocytes prepared, and assayed in an murine interferon gamma Elispot assay. (Lalvani et al. 1997 *J. Exp. Med.* 186: 859–865; Forsthuber, T., et al 1996 *Science* 271: 1728–1730; Chu, R. et al. 1997. *J. Exp. Med.* 186: 1623–1631, each of which is incorporated by reference.) Splenocyte cultures were incubated at 37° C. for 24 hr. in the presence of a pool of 36 overlapping 20 amino acid residue peptides (final concentration, 4 μg/mL each) scanning the full length of HPV 16 E2. Interferon gamma was captured on the substrate by monoclonal antibody (mAb) R4-6A2 (Pharmagin), and detected with biotinylated mAb XMG1.2 (Pharmagin) and a strepavidin-alkaline phosphatase conjugate (Pharmagin). Results are shown in Table A, below. The immunized mice developed CD4+ immune responses to HPV (Table A, below).

Immunization with E2 DNA did not induce detectable anti-E2 antibody responses.

TABLE A

| Dose Group | Immunization | E2-specific spots (per $10^6$ cells) |
|---|---|---|
| 1 | E2 DNA 1 | 392 |
| 2 | E2 DNA 2 | 96 |
| 3 | E2 DNA 3 | 134 |
| 4 | Control DNA 1 | 0 |
| 5 | Control DNA 2 | 2 |

Protection from challenge with JCL-031 cells.

BALB/c mice, Immunized with V1Jns:E2 DNA, or control DNA, were challenged by subcutaneous injection of $5\times10^5$ JCL-031 cells into the left inguinal region. Tumor growth was monitored by palpation or caliper measurement for a four-week period. FIG. 26 reports the fraction of each dose group that remained tumor free. The group that had been immunized with an E2-expressing plasmid was significantly protected from tumor development compared to the control group.

What is claimed is:

1. A synthetic polynucleotide comprising a nucleotide sequence encoding a codon-optimized human papillomavirus serotype 16 (HPV16) protein, wherein said nucleotide sequence comprises codons that are optimized for expression in a human host, and wherein the protein is selected from the group consisting of: L1, E1, E2, and E7 of HPV16.

2. A polynucleotide according to claim 1, wherein the polynucleotide is DNA.

3. A polynucleotide according to claim 2, wherein the protein is an HPV16 L1 protein.

4. A synthetic polynucleotide comprising a nucleotide sequence encoding a codon-optimized human papillomavirus serotype 16 (HPV16) protein wherein said nucleotide sequence comprises codons that are optimized for expression in a human host, the polynucleotide comprising a sequence of nucleotides as set forth in SEQ.ID.NO: 1, wherein the polynucleotide is DNA.

5. A polynucleotide according to claim 2, wherein the polynucleotide encodes an HPV16 E1 protein.

6. A synthetic polynucleotide which comprises a sequence of nucleotides as set forth in SEQ.ID.NO:2.

7. A synthetic polynucleotide which comprises a sequence of nucleotides as set forth in SEQ. ID.NO: 3.

8. A polynucleotide according to claim 2, wherein the protein is an HPV16 E7 protein.

9. A synthetic polynucleotide which comprises a sequence of nucleotides as set forth in SEQ. ID.NO:4.

10. An adenoviral vaccine vector comprising an adenoviral genome with a deletion in the E1 region, and an insert in the E1 region, wherein the insert comprises an expression cassette comprising:

A) a polynucleotide encoding a codon-optimized HPV16 protein selected from the group consisting of L1, E1, E2, and E7 proteins, wherein said polynucleotide is codon-optimized for expression in a human host cell; and B) a promoter operably linked to the polynucleotide.

11. A vector according to claim 10, wherein the adenoviral genome also contains a deleted E3 region.

12. A shuttle plasmid vector comprising a plasmid portion and an adenoviral portion, the adenoviral portion comprising: an adenoviral genome with a deletion in the E1 region, and an insert in the E1 region, wherein the insert comprises an expression cassette comprising:

A) a polynucleotide encoding a codon-optimized HPV 16 protein selected from the group consisting of L1, E1, E2, and E7 proteins, wherein said polynucleotide is codon-optimized for expression in a human host cell; and B) a promoter operably linked to the polynucleotide.

13. A vaccine plasmid comprising a plasmid portion and an expression cassette portion, wherein the expression cassette portion comprises:

A) a polynucleotide encoding a codon-optimized HPV16 protein selected from the group consisting of L1, E1, E2, and E7 proteins, wherein said polynucleotide is codon-optimized for expression in a human host cell; and B) a promoter operably linked to the polynucleotide.

14. A plasmid according to claim 13, wherein the plasmid portion is V1Jns.

15. A process for expressing an HPV 16 protein in a recombinant host cell, comprising:

(A) introducing a vector comprising the synthetic polynucleotide of claim 1 into a suitable human host cell; and, (B) culturing the host cell under conditions which allow expression of said HPV16 protein.

* * * * *

SEQUENCE LISTING

```
<160> NUMBER OF SEQ ID NOS: 98

<210> SEQ ID NO 1
<211> LENGTH: 3147
<212> TYPE: DNA
<213> ORGANISM: Homo sapiens
<220> FEATURE:
<223> OTHER INFORMATION: TADG-15

<400> SEQUENCE: 1

tcaagagcgg cctcggggta ccatggggag cgatcgggcc cgcaagggcg gagggggccc     60

gaaggacttc ggcgcgggac tcaagtacaa ctcccggcac gagaaagtga atggcttgga    120

ggaaggcgtg gagttcctgc cagtcaacaa cgtcaagaag gtggaaaagc atggcccggg    180

gcgctgggtg gtgctggcag ccgtgctgat cggcctcctc ttggtcttgc tggggatcgg    240

cttcctggtg tggcatttgc agtaccggga cgtgcgtgtc cagaaggtct tcaatggcta    300
```

-continued

```
catgaggatc acaaatgaga attttgtgga tgcctacgag aactccaact ccactgagtt    360
tgtaagcctg gccagcaagg tgaaggacgc gctgaagctg ctgtacagcg gagtcccatt    420
cctgggcccc taccacaagg agtcggctgt gacggccttc agcgagggca gcgtcatcgc    480
ctactactgg tctgagttca gcatcccgca gcacctggtg gaggaggccg agcgcgtcat    540
ggccgaggag cgcgtagtca tgctgccccc gcgggcgcgc tccctgaagt cctttgtggt    600
cacctcagtg gtggctttcc ccacggactc caaaacagta cagaggaccc aggacaacag    660
ctgcagcttt ggcctgcacg cccgcggtgt ggagctgatg cgcttcacca cgcccggctt    720
ccctgacagc ccctaccccg ctcatgcccg ctgccagtgg gccctgcggg gggacgccga    780
ctcagtgctg agcctcacct tccgcagctt tgaccttgcg tcctgcgacg agcgcggcag    840
cgacctggtg acggtgtaca acaccctgag ccccatggag ccccacgccc tggtgcagtt    900
gtgtggcacc taccctccct cctacaacct gaccttccac tcctcccaga acgtcctgct    960
catcacactg ataaccaaca ctgagcggcg gcatcccggc tttgaggcca ccttcttcca   1020
gctgcctagg atgagcagct gtggaggccg cttacgtaaa gcccagggga cattcaacag   1080
cccctactac ccaggccact acccacccaa cattgactgc acatggaaca ttgaggtgcc   1140
caacaaccag catgtgaagg tgagcttcaa attcttctac ctgctggagc ccggcgtgcc   1200
tgcgggcacc tgccccaagg actacgtgga gatcaatggg gagaaatact gcggagagag   1260
gtcccagttc gtcgtcacca gcaacagcaa caagatcaca gttcgcttcc actcagatca   1320
gtcctacacc gacaccggct tcttagctga atacctctcc tacgactcca gtgacccatg   1380
cccggggcag ttcacgtgcc gcacggggcg gtgtatccgg aaggagctgc gctgtgatgg   1440
ctgggccgac tgcaccgacc acagcgatga gctcaactgc agttgcgacg ccggccacca   1500
gttcacgtgc aagaacaagt tctgcaagcc cctcttctgg gtctgcgaca gtgtgaacga   1560
ctgcggagac aacagcgacg agcaggggtg cagttgtccg gcccagacct tcaggtgttc   1620
caatgggaag tgcctctcga aaagccagca gtgcaatggg aaggacgact gtggggacgg   1680
gtccgacgag gcctcctgcc ccaaggtgaa cgtcgtcact tgtaccaaac acacctaccg   1740
ctgcctcaat gggctctgct tgagcaaggg caaccctgag tgtgacggga aggaggactg   1800
tagcgacggc tcagatgaga aggactgcga ctgtgggctg cggtcattca cgagacaggc   1860
tcgtgttgtt gggggcacgg atgcggatga gggcgagtgg ccctggcagg taagcctgca   1920
tgctctgggc cagggccaca tctgcggtgc ttccctcatc tctcccaact ggctggtctc   1980
tgccgcacac tgctacatcg atgacagagg attcaggtac tcagacccca cgcagtggac   2040
ggccttcctg ggcttgcacg accagagcca gcgcagcgcc cctggggtgc aggagcgcag   2100
gctcaagcgc atcatctccc acccctctt caatgacttc accttcgact atgacatcgc   2160
gctgctggag ctggagaaac cggcagagta cagctccatg gtgcggccca tctgcctgcc   2220
ggacgcctcc catgtcttcc ctgccggcaa ggccatctgg gtcacgggct ggggacacac   2280
ccagtatgga ggcactggcg cgctgatcct gcaaaagggt gagatccgcg tcatcaacca   2340
gaccacctgc gagaacctcc tgccgcagca gatcacgccg cgcatgatgt gcgtgggctt   2400
cctcagcggc ggcgtggact cctgccaggg tgattccggg ggacccctgt ccagcgtgga   2460
ggcggatggg cggatcttcc aggccggtgt ggtgagctgg ggagacggct gcgctcagag   2520
gaacaagcca ggcgtgtaca caaggctccc tctgtttcgg gactggatca aagagaacac   2580
tggggtatag ggccggggc cacccaaatg tgtacacctg cggggccacc catcgtccac   2640
cccagtgtgc acgcctgcag gctggagact ggaccgctga ctgcaccagc gcccccagaa   2700
```

-continued

```
catacactgt gaactcaatc tccagggctc caaatctgcc tagaaaacct ctcgcttcct   2760

cagcctccaa agtggagctg ggaggtagaa ggggaggaca ctggtggttc tactgaccca   2820

actgggggca aaggtttgaa gacacagcct cccccgccag ccccaagctg ggccgaggcg   2880

cgtttgtgta tatctgcctc ccctgtctgt aaggagcagc gggaacggag cttcggagcc   2940

tcctcagtga aggtggtggg gctgccggat ctgggctgtg gggcccttgg gccacgctct   3000

tgaggaagcc caggctcgga ggaccctgga aaacagacgg gtctgagact gaaattgttt   3060

taccagctcc cagggtggac ttcagtgtgt gtatttgtgt aaatgggtaa aacaatttat   3120

ttctttttaa aaaaaaaaaa aaaaaaa                                         3147
```

```
<210> SEQ ID NO 2
<211> LENGTH: 855
<212> TYPE: PRT
<213> ORGANISM: Homo sapiens
<220> FEATURE:
<223> OTHER INFORMATION: TADG-15

<400> SEQUENCE: 2

Met Gly Ser Asp Arg Ala Arg Lys Gly Gly Gly Gly Pro Lys Asp
                5                   10                  15

Phe Gly Ala Gly Leu Lys Tyr Asn Ser Arg His Glu Lys Val Asn
                20                  25                  30

Gly Leu Glu Glu Gly Val Glu Phe Leu Pro Val Asn Asn Val Lys
                35                  40                  45

Lys Val Glu Lys His Gly Pro Gly Arg Trp Val Val Leu Ala Ala
                50                  55                  60

Val Leu Ile Gly Leu Leu Leu Val Leu Leu Gly Ile Gly Phe Leu
                65                  70                  75

Val Trp His Leu Gln Tyr Arg Asp Val Arg Val Gln Lys Val Phe
                80                  85                  90

Asn Gly Tyr Met Arg Ile Thr Asn Glu Asn Phe Val Asp Ala Tyr
                95                  100                 105

Glu Asn Ser Asn Ser Thr Glu Phe Val Ser Leu Ala Ser Lys Val
                110                 115                 120

Lys Asp Ala Leu Lys Leu Leu Tyr Ser Gly Val Pro Phe Leu Gly
                125                 130                 135

Pro Tyr His Lys Glu Ser Ala Val Thr Ala Phe Ser Glu Gly Ser
                140                 145                 150

Val Ile Ala Tyr Tyr Trp Ser Glu Phe Ser Ile Pro Gln His Leu
                155                 160                 165

Val Glu Glu Ala Glu Arg Val Met Ala Glu Glu Arg Val Val Met
                170                 175                 180

Leu Pro Pro Arg Ala Arg Ser Leu Lys Ser Phe Val Val Thr Ser
                185                 190                 195

Val Val Ala Phe Pro Thr Asp Ser Lys Thr Val Gln Arg Thr Gln
                200                 205                 210

Asp Asn Ser Cys Ser Phe Gly Leu His Ala Arg Gly Val Glu Leu
                215                 220                 225

Met Arg Phe Thr Thr Pro Gly Phe Pro Asp Ser Pro Tyr Pro Ala
                230                 235                 240

His Ala Arg Cys Gln Trp Ala Leu Arg Gly Asp Ala Asp Ser Val
                245                 250                 255

Leu Ser Leu Thr Phe Arg Ser Phe Asp Leu Ala Ser Cys Asp Glu
```

-continued

```
                260                 265                 270

Arg Gly Ser Asp Leu Val Thr Val Tyr Asn Thr Leu Ser Pro Met
                275                 280                 285

Glu Pro His Ala Leu Val Gln Leu Cys Gly Thr Tyr Pro Pro Ser
                290                 295                 300

Tyr Asn Leu Thr Phe His Ser Ser Gln Asn Val Leu Leu Ile Thr
                305                 310                 315

Leu Ile Thr Asn Thr Glu Arg Arg His Pro Gly Phe Glu Ala Thr
                320                 325                 330

Phe Phe Gln Leu Pro Arg Met Ser Ser Cys Gly Gly Arg Leu Arg
                335                 340                 345

Lys Ala Gln Gly Thr Phe Asn Ser Pro Tyr Tyr Pro Gly His Tyr
                350                 355                 360

Pro Pro Asn Ile Asp Cys Thr Trp Asn Ile Glu Val Pro Asn Asn
                365                 370                 375

Gln His Val Lys Val Ser Phe Lys Phe Phe Tyr Leu Leu Glu Pro
                380                 385                 390

Gly Val Pro Ala Gly Thr Cys Pro Lys Asp Tyr Val Glu Ile Asn
                395                 400                 405

Gly Glu Lys Tyr Cys Gly Glu Arg Ser Gln Phe Val Val Thr Ser
                410                 415                 420

Asn Ser Asn Lys Ile Thr Val Arg Phe His Ser Asp Gln Ser Tyr
                425                 430                 435

Thr Asp Thr Gly Phe Leu Ala Glu Tyr Leu Ser Tyr Asp Ser Ser
                440                 445                 450

Asp Pro Cys Pro Gly Gln Phe Thr Cys Arg Thr Gly Arg Cys Ile
                455                 460                 465

Arg Lys Glu Leu Arg Cys Asp Gly Trp Ala Asp Cys Thr Asp His
                470                 475                 480

Ser Asp Glu Leu Asn Cys Ser Cys Asp Ala Gly His Gln Phe Thr
                485                 490                 495

Cys Lys Asn Lys Phe Cys Lys Pro Leu Phe Trp Val Cys Asp Ser
                500                 505                 510

Val Asn Asp Cys Gly Asp Asn Ser Asp Glu Gln Gly Cys Ser Cys
                515                 520                 525

Pro Ala Gln Thr Phe Arg Cys Ser Asn Gly Lys Cys Leu Ser Lys
                530                 535                 540

Ser Gln Gln Cys Asn Gly Lys Asp Asp Cys Gly Asp Gly Ser Asp
                545                 550                 555

Glu Ala Ser Cys Pro Lys Val Asn Val Val Thr Cys Thr Lys His
                560                 565                 570

Thr Tyr Arg Cys Leu Asn Gly Leu Cys Leu Ser Lys Gly Asn Pro
                575                 580                 585

Glu Cys Asp Gly Lys Glu Asp Cys Ser Asp Gly Ser Asp Glu Lys
                590                 595                 600

Asp Cys Asp Cys Gly Leu Arg Ser Phe Thr Arg Gln Ala Arg Val
                605                 610                 615

Val Gly Gly Thr Asp Ala Asp Glu Gly Glu Trp Pro Trp Gln Val
                620                 625                 630

Ser Leu His Ala Leu Gly Gln Gly His Ile Cys Gly Ala Ser Leu
                635                 640                 645

Ile Ser Pro Asn Trp Leu Val Ser Ala Ala His Cys Tyr Ile Asp
                650                 655                 660
```

-continued

```
Asp Arg Gly Phe Arg Tyr Ser Asp Pro Thr Gln Trp Thr Ala Phe
                665                 670                 675

Leu Gly Leu His Asp Gln Ser Gln Arg Ser Ala Pro Gly Val Gln
                680                 685                 690

Glu Arg Arg Leu Lys Arg Ile Ile Ser His Pro Phe Phe Asn Asp
                695                 700                 705

Phe Thr Phe Asp Tyr Asp Ile Ala Leu Leu Glu Leu Glu Lys Pro
                710                 715                 720

Ala Glu Tyr Ser Ser Met Val Arg Pro Ile Cys Leu Pro Asp Ala
                725                 730                 735

Ser His Val Phe Pro Ala Gly Lys Ala Ile Trp Val Thr Gly Trp
                740                 745                 750

Gly His Thr Gln Tyr Gly Gly Thr Gly Ala Leu Ile Leu Gln Lys
                755                 760                 765

Gly Glu Ile Arg Val Ile Asn Gln Thr Thr Cys Glu Asn Leu Leu
                770                 775                 780

Pro Gln Gln Ile Thr Pro Arg Met Met Cys Val Gly Phe Leu Ser
                785                 790                 795

Gly Gly Val Asp Ser Cys Gln Gly Asp Ser Gly Gly Pro Leu Ser
                800                 805                 810

Ser Val Glu Ala Asp Gly Arg Ile Phe Gln Ala Gly Val Val Ser
                815                 820                 825

Trp Gly Asp Gly Cys Ala Gln Arg Asn Lys Pro Gly Val Tyr Thr
                830                 835                 840

Arg Leu Pro Leu Phe Arg Asp Trp Ile Lys Glu Asn Thr Gly Val
                845                 850                 855


<210> SEQ ID NO 3
<211> LENGTH: 256
<212> TYPE: PRT
<213> ORGANISM: Homo sapiens
<220> FEATURE:
<223> OTHER INFORMATION: Hepsin

<400> SEQUENCE: 3

Arg Ile Val Gly Gly Arg Asp Thr Ser Leu Gly Arg Trp Pro Trp
                5                   10                  15

Gln Val Ser Leu Arg Tyr Asp Gly Ala His Leu Cys Gly Gly Ser
                20                  25                  30

Leu Leu Ser Gly Asp Trp Val Leu Thr Ala Ala His Cys Phe Pro
                35                  40                  45

Glu Arg Asn Arg Val Leu Ser Arg Trp Arg Val Phe Ala Gly Ala
                50                  55                  60

Val Ala Gln Ala Ser Pro His Gly Leu Gln Leu Gly Val Gln Ala
                65                  70                  75

Val Val Tyr His Gly Gly Tyr Leu Pro Phe Arg Asp Pro Asn Ser
                80                  85                  90

Glu Glu Asn Ser Asn Asp Ile Ala Leu Val His Leu Ser Ser Pro
                95                  100                 105

Leu Pro Leu Thr Glu Tyr Ile Gln Pro Val Cys Leu Pro Ala Ala
                110                 115                 120

Gly Gln Ala Leu Val Asp Gly Lys Ile Cys Thr Val Thr Gly Trp
                125                 130                 135

Gly Asn Thr Gln Tyr Tyr Gly Gln Gln Ala Gly Val Leu Gln Glu
                140                 145                 150
```

-continued

```
Ala Arg Val Pro Ile Ile Ser Asn Asp Val Cys Asn Gly Ala Asp
                155                 160                 165

Phe Tyr Gly Asn Gln Ile Lys Pro Lys Met Phe Cys Ala Gly Tyr
                170                 175                 180

Pro Glu Gly Gly Ile Asp Ala Cys Gln Gly Asp Ser Gly Gly Pro
                185                 190                 195

Phe Val Cys Glu Asp Ser Ile Ser Arg Thr Pro Arg Trp Arg Leu
                200                 205                 210

Cys Gly Ile Val Ser Trp Gly Thr Gly Cys Ala Leu Ala Gln Lys
                215                 220                 225

Pro Gly Val Tyr Thr Lys Val Ser Asp Phe Arg Glu Trp Ile Phe
                230                 235                 240

Gln Ala Ile Lys Thr His Ser Glu Ala Ser Gly Met Val Thr Gln
                245                 250                 255

Leu


<210> SEQ ID NO 4
<211> LENGTH: 225
<212> TYPE: PRT
<213> ORGANISM: Homo sapiens
<220> FEATURE:
<223> OTHER INFORMATION: SCCE

<400> SEQUENCE: 4

Lys Ile Ile Asp Gly Ala Pro Cys Ala Arg Gly Ser His Pro Trp
                5                   10                  15

Gln Val Ala Leu Leu Ser Gly Asn Gln Leu His Cys Gly Gly Val
                20                  25                  30

Leu Val Asn Glu Arg Trp Val Leu Thr Ala Ala His Cys Lys Met
                35                  40                  45

Asn Glu Tyr Thr Val His Leu Gly Ser Asp Thr Leu Gly Asp Arg
                50                  55                  60

Arg Ala Gln Arg Ile Lys Ala Ser Lys Ser Phe Arg His Pro Gly
                65                  70                  75

Tyr Ser Thr Gln Thr His Val Asn Asp Leu Met Leu Val Lys Leu
                80                  85                  90

Asn Ser Gln Ala Arg Leu Ser Ser Met Val Lys Lys Val Arg Leu
                95                  100                 105

Pro Ser Arg Cys Glu Pro Pro Gly Thr Thr Cys Thr Val Ser Gly
                110                 115                 120

Trp Gly Thr Thr Thr Ser Pro Asp Val Thr Phe Pro Ser Asp Leu
                125                 130                 135

Met Cys Val Asp Val Lys Leu Ile Ser Pro Gln Asp Cys Thr Lys
                140                 145                 150

Val Tyr Lys Asp Leu Leu Glu Asn Ser Met Leu Cys Ala Gly Ile
                155                 160                 165

Pro Asp Ser Lys Lys Asn Ala Cys Asn Gly Asp Ser Gly Gly Pro
                170                 175                 180

Leu Val Cys Arg Gly Thr Leu Gln Gly Leu Val Ser Trp Gly Thr
                185                 190                 195

Phe Pro Cys Gly Gln Pro Asn Asp Pro Gly Val Tyr Thr Gln Val
                200                 205                 210

Cys Lys Phe Thr Lys Trp Ile Asn Asp Thr Met Lys Lys His Arg
                215                 220                 225
```

<210> SEQ ID NO 5
<211> LENGTH: 225
<212> TYPE: PRT
<213> ORGANISM: Homo sapiens
<220> FEATURE:
<223> OTHER INFORMATION: Trypsin

<400> SEQUENCE: 5

```
Lys Ile Val Gly Gly Tyr Asn Cys Glu Glu Asn Ser Val Pro Tyr
                5                   10                  15

Gln Val Ser Leu Asn Ser Gly Tyr His Phe Cys Gly Gly Ser Leu
                20                  25                  30

Ile Asn Glu Gln Trp Val Val Ser Ala Gly His Cys Tyr Lys Ser
                35                  40                  45

Arg Ile Gln Val Arg Leu Gly Glu His Asn Ile Glu Val Leu Glu
                50                  55                  60

Gly Asn Glu Gln Phe Ile Asn Ala Ala Lys Ile Ile Arg His Pro
                65                  70                  75

Gln Tyr Asp Arg Lys Thr Leu Asn Asn Asp Ile Met Leu Ile Lys
                80                  85                  90

Leu Ser Ser Arg Ala Val Ile Asn Ala Arg Val Ser Thr Ile Ser
                95                  100                 105

Leu Pro Thr Ala Pro Pro Ala Thr Gly Thr Lys Cys Leu Ile Ser
                110                 115                 120

Gly Trp Gly Asn Thr Ala Ser Ser Gly Ala Asp Tyr Pro Asp Glu
                125                 130                 135

Leu Gln Cys Leu Asp Ala Pro Val Leu Ser Gln Ala Lys Cys Glu
                140                 145                 150

Ala Ser Tyr Pro Gly Lys Ile Thr Ser Asn Met Phe Cys Val Gly
                155                 160                 165

Phe Leu Glu Gly Gly Lys Asp Ser Cys Gln Gly Asp Ser Gly Gly
                170                 175                 180

Pro Val Val Cys Asn Gly Gln Leu Gln Gly Val Val Ser Trp Gly
                185                 190                 195

Asp Gly Cys Ala Gln Lys Asn Lys Pro Gly Val Tyr Thr Lys Val
                200                 205                 210

Tyr Asn Tyr Val Lys Trp Ile Lys Asn Thr Ile Ala Ala Asn Ser
                215                 220                 225
```

<210> SEQ ID NO 6
<211> LENGTH: 231
<212> TYPE: PRT
<213> ORGANISM: Homo sapiens
<220> FEATURE:
<223> OTHER INFORMATION: Chymotrypsin

<400> SEQUENCE: 6

```
Arg Ile Val Asn Gly Glu Asp Ala Val Pro Gly Ser Trp Pro Trp
                5                   10                  15

Gln Val Ser Leu Gln Asp Lys Thr Gly Phe His Phe Cys Gly Gly
                20                  25                  30

Ser Leu Ile Ser Glu Asp Trp Val Val Thr Ala Ala His Cys Gly
                35                  40                  45

Val Arg Thr Ser Asp Val Val Val Ala Gly Glu Phe Asp Gln Gly
                50                  55                  60

Ser Asp Glu Glu Asn Ile Gln Val Leu Lys Ile Ala Lys Val Phe
                65                  70                  75
```

```
Lys Asn Pro Lys Phe Ser Ile Leu Thr Val Asn Asn Asp Ile Thr
                80                  85                  90

Leu Leu Lys Leu Ala Thr Pro Ala Arg Phe Ser Gln Thr Val Ser
                95                  100                 105

Ala Val Cys Leu Pro Ser Ala Asp Asp Asp Phe Pro Ala Gly Thr
                110                 115                 120

Leu Cys Ala Thr Thr Gly Trp Gly Lys Thr Lys Tyr Asn Ala Asn
                125                 130                 135

Lys Thr Pro Asp Lys Leu Gln Gln Ala Ala Leu Pro Leu Leu Ser
                140                 145                 150

Asn Ala Glu Cys Lys Lys Ser Trp Gly Arg Arg Ile Thr Asp Val
                155                 160                 165

Met Ile Cys Ala Gly Ala Ser Gly Val Ser Ser Cys Met Gly Asp
                170                 175                 180

Ser Gly Gly Pro Leu Val Cys Gln Lys Asp Gly Ala Trp Thr Leu
                185                 190                 195

Val Gly Ile Val Ser Trp Gly Ser Asp Thr Cys Ser Thr Ser Ser
                200                 205                 210

Pro Gly Val Tyr Ala Arg Val Thr Lys Leu Ile Pro Trp Val Gln
                215                 220                 225

Lys Ile Leu Ala Ala Asn
                230


<210> SEQ ID NO 7
<211> LENGTH: 255
<212> TYPE: PRT
<213> ORGANISM: Homo sapiens
<220> FEATURE:
<223> OTHER INFORMATION: Factor 7

<400> SEQUENCE: 7

Arg Ile Val Gly Gly Lys Val Cys Pro Lys Gly Glu Cys Pro Trp
                5                   10                  15

Gln Val Leu Leu Leu Val Asn Gly Ala Gln Leu Cys Gly Gly Thr
                20                  25                  30

Leu Ile Asn Thr Ile Trp Val Val Ser Ala Ala His Cys Phe Asp
                35                  40                  45

Lys Ile Lys Asn Trp Arg Asn Leu Ile Ala Val Leu Gly Glu His
                50                  55                  60

Asp Leu Ser Glu His Asp Gly Asp Glu Gln Ser Arg Arg Val Ala
                65                  70                  75

Gln Val Ile Ile Pro Ser Thr Tyr Val Pro Gly Thr Thr Asn His
                80                  85                  90

Asp Ile Ala Leu Leu Arg Leu His Gln Pro Val Val Leu Thr Asp
                95                  100                 105

His Val Val Pro Leu Cys Leu Pro Glu Arg Thr Phe Ser Glu Arg
                110                 115                 120

Thr Leu Ala Phe Val Arg Phe Ser Leu Val Ser Gly Trp Gly Gln
                125                 130                 135

Leu Leu Asp Arg Gly Ala Thr Ala Leu Glu Leu Met Val Leu Asn
                140                 145                 150

Val Pro Arg Leu Met Thr Gln Asp Cys Leu Gln Gln Ser Arg Lys
                155                 160                 165

Val Gly Asp Ser Pro Asn Ile Thr Glu Tyr Met Phe Cys Ala Gly
                170                 175                 180
```

-continued

```
Tyr Ser Asp Gly Ser Lys Asp Ser Cys Lys Gly Asp Ser Gly Gly
                185                 190                 195

Pro His Ala Thr His Tyr Arg Gly Thr Trp Tyr Leu Thr Gly Ile
                200                 205                 210

Val Ser Trp Gly Gln Gly Cys Ala Thr Val Gly His Phe Gly Val
                215                 220                 225

Tyr Thr Arg Val Ser Gln Tyr Ile Glu Trp Leu Gln Lys Leu Met
                230                 235                 240

Arg Ser Glu Pro Arg Pro Gly Val Leu Leu Arg Ala Pro Phe Pro
                245                 250                 255


<210> SEQ ID NO 8
<211> LENGTH: 253
<212> TYPE: PRT
<213> ORGANISM: Homo sapiens
<220> FEATURE:
<223> OTHER INFORMATION: Tissue plasminogen activator

<400> SEQUENCE: 8

Arg Ile Lys Gly Gly Leu Phe Ala Asp Ile Ala Ser His Pro Trp
                5                   10                  15

Gln Ala Ala Ile Phe Ala Lys His Arg Arg Ser Pro Gly Glu Arg
                20                  25                  30

Phe Leu Cys Gly Gly Ile Leu Ile Ser Ser Cys Trp Ile Leu Ser
                35                  40                  45

Ala Ala His Cys Phe Gln Glu Arg Phe Pro Pro His His Leu Thr
                50                  55                  60

Val Ile Leu Gly Arg Thr Tyr Arg Val Val Pro Gly Glu Glu Glu
                65                  70                  75

Gln Lys Phe Glu Val Glu Lys Tyr Ile Val His Lys Glu Phe Asp
                80                  85                  90

Asp Asp Thr Tyr Asp Asn Asp Ile Ala Leu Leu Gln Leu Lys Ser
                95                  100                 105

Asp Ser Ser Arg Cys Ala Gln Glu Ser Ser Val Val Arg Thr Val
                110                 115                 120

Cys Leu Pro Pro Ala Asp Leu Gln Leu Pro Asp Trp Thr Glu Cys
                125                 130                 135

Glu Leu Ser Gly Tyr Gly Lys His Glu Ala Leu Ser Pro Phe Tyr
                140                 145                 150

Ser Glu Arg Leu Lys Glu Ala His Val Arg Leu Tyr Pro Ser Ser
                155                 160                 165

Arg Cys Thr Ser Gln His Leu Leu Asn Arg Thr Val Thr Asp Asn
                170                 175                 180

Met Leu Cys Ala Gly Asp Thr Arg Ser Gly Gly Pro Gln Ala Asn
                185                 190                 195

Leu His Asp Ala Cys Gln Gly Asp Ser Gly Gly Pro Leu Val Cys
                200                 205                 210

Leu Asn Asp Gly Arg Met Thr Leu Val Gly Ile Ile Ser Trp Gly
                215                 220                 225

Leu Gly Cys Gly Gln Lys Asp Val Pro Gly Val Tyr Thr Lys Val
                230                 235                 240

Thr Asn Tyr Leu Asp Trp Ile Arg Asp Asn Met Arg Pro
                245                 250


<210> SEQ ID NO 9
```

-continued

```
<211> LENGTH: 2900
<212> TYPE: DNA
<213> ORGANISM: Homo sapiens
<220> FEATURE:
<223> OTHER INFORMATION: SNC-19; GeneBank Accession No. #U20428

<400> SEQUENCE: 9

cgctgggtgg tgctggcagc cgtgctgatc ggcctcctct tggtcttgct ggggatcggc     60

ttcctggtgt ggcatttgca gtaccgggac gtgcgtgtcc agaaggtctt caatggctac    120

atgaggatca caaatgagaa ttttgtggat gcctacgaga actccaactc cactgagttt    180

gtaagcctgg ccagcaaggt gaaggacgcg ctgaagctgc tgtacagcgg agtcccattc    240

ctgggcccct accacaagga gtcggctgtg acggccttca gcgagggcag cgtcatcgcc    300

tactactggt ctgagttcag catcccgcag cacctggttg aggaggccga gcgcgtcatg    360

gccaggagcg cgtagtcatg ctgcccccgc gggcgcgctc cctgaagtcc tttgtggtca    420

cctcagtggt ggctttcccc acggactcca aaacagtaca gaggacccag gacaacagct    480

gcagctttgg cctgcacgcc gcggtgtgga gctgatgcgc ttcaccacgc cggcttccct    540

gacagcccct accccgctca tgcccgctgc cagtgggctg cggggacgcg acgcagtgct    600

gagctactcg agctgactcg cagcttgact gcgcctcgac gagcgcggca gcgacctggt    660

gacgtgtaca acaccctgag ccccatggag ccccacgcct ggtgagtgtg tggcacctac    720

cctccctcct acaacctgac cttccactcc ctcccacgaa cgtcctgctc atcacactga    780

taaccaacac tgacgcggca tcccggcttt gaggccacct tcttccagct gcctaggatg    840

agcagctgtg gaggccgctt acgtaaagcc caggggacat tcaacagccc ctactaccca    900

ggccactacc cacccaacat tgactgcaca tggaaaattg aggtgcccaa caaccagcat    960

gtgaaggtgc gcttcaaatt cttctacctg ctggagcccg gcgtgcctgc gggcacctgc   1020

cccaaggact acgtggagat caatggggag aaatactgcg gagagaggtc ccagttcgtc   1080

gtcaccagca acagcaacaa gatcacagtt cgcttccact cagatcagtc ctacaccgac   1140

accggcttct tagctgaata cctctcctac gactccagtg acccatgccc ggggcagttc   1200

acgtgccgca cggggcggtg tatccggaag gagctgcgct gtgatggctg ggcgactgca   1260

ccgaccacag cgatgagctc aactgcagtt gcgacgccgg ccaccagttc acgtgcaaga   1320

gcaagttctg caagctcttc tgggtctgcg acagtgtgaa cgagtgcgga gacaacagcg   1380

acgagcaggg ttgcatttgt ccggacccag accttcaggt gttccaatgg gaagtgcctc   1440

tcgaaaagcc agcagtgcaa tgggaaggac gactgtgggg acgggtccga cgaggcctcc   1500

tgccccaagg tgaacgtcgt cacttgtacc aaacacacct accgctgcct caatgggctc   1560

tgcttgagca agggcaaccc tgagtgtgac gggaaggagg actgtagcga cggctcagat   1620

gagaaggact gcgactgtgg gctgcggtca ttcacgagac aggctcgtgt tgttgggggc   1680

acggatgcgg atgagggcga gtggccctgg caggtaagcc tgcatgctct gggccagggc   1740

cacatctgcg gtgcttccct catctctccc aactggctgg tctctgccgc acactgctac   1800

atcgatgaca gaggattcag gtactcagac cccacgcagg acggccttcc tgggcttgca   1860

cgaccagagc cagcgcaggc cctggggtgc aggagcgcag gctcaagcgc atcatctccc   1920

accccttctt caatgacttc accttcgact atgacatcgc gctgctggag ctggagaaac   1980

cggcagagta cagctccatg gtgcggccca tctgcctgcc ggacgcctgc catgtcttcc   2040

ctgccggcaa ggccatctgg gtcacgggct ggggacacac ccagtatgga ggcactggcg   2100

cgctgatcct gcaaaagggt gagatccgcg tcatcaacca gaccacctgc gagaacctcc   2160
```

```
tgccgcagca gatcacgccg cgcatgatgt gcgtgggctt cctcagcggc ggcgtggact   2220

cctgccaggg tgattccggg ggacccctgt ccagcgtgga ggcggatggg cggatcttcc   2280

aggccggtgt ggtgagctgg ggagacgctg cgctcagagg aacaagccag gcgtgtacac   2340

aaggctccct ctgtttcggg aatggatcaa agagaacact ggggtatagg ggccggggcc   2400

acccaaatgt gtacacctgc ggggccaccc atcgtccacc ccagtgtgca cgcctgcagg   2460

ctggagactc gcgcaccgtg acctgcacca gcgccccaga acatacactg tgaactcatc   2520

tccaggctca aatctgctag aaaacctctc gcttcctcag cctccaaagt ggagctggga   2580

gggtagaagg ggaggaacac tggtggttct actgacccaa ctggggcaag gtttgaagca   2640

cagctccggc agcccaagtg ggcgaggacg cgtttgtgca tactgccctg ctctatacac   2700

ggaagacctg gatctctagt gagtgtgact gccggatctg gctgtggtcc ttggccacgc   2760

ttcttgagga agcccaggct cggaggaccc tggaaaacag acgggtctga gactgaaaat   2820

ggtttaccag ctcccaggtg acttcagtgt gtgtattgtg taaatgagta aaacatttta   2880

tttcttttta aaaaaaaaaa                                                2900
```

<210> SEQ ID NO 10
<211> LENGTH: 902
<212> TYPE: PRT
<213> ORGANISM: Mus musculus
<220> FEATURE:
<223> OTHER INFORMATION: Epithin

<400> SEQUENCE: 10

```
Met Gly Ser Asn Arg Gly Arg Lys Ala Gly Gly Gly Ser Gln Asp
                5                   10                  15

Phe Gly Ala Gly Leu Lys Tyr Asp Ser Arg Leu Glu Asn Met Asn
                20                  25                  30

Gly Phe Glu Glu Gly Val Glu Phe Leu Pro Ala Asn Asn Ala Lys
                35                  40                  45

Lys Val Glu Lys Arg Gly Pro Arg Arg Trp Val Val Leu Val Ala
                50                  55                  60

Val Leu Phe Ser Phe Leu Leu Leu Ser Leu Met Ala Gly Leu Leu
                65                  70                  75

Val Trp His Phe His Tyr Arg Asn Val Arg Val Gln Lys Val Phe
                80                  85                  90

Asn Gly His Leu Arg Ile Thr Asn Glu Ile Phe Leu Asp Ala Tyr
                95                  100                 105

Glu Asn Ser Thr Ser Thr Glu Phe Ile Ser Leu Ala Ser Gln Val
                110                 115                 120

Lys Glu Ala Leu Lys Leu Leu Tyr Asn Glu Val Pro Val Leu Gly
                125                 130                 135

Pro Tyr His Lys Lys Ser Ala Val Thr Ala Phe Ser Glu Gly Ser
                140                 145                 150

Val Ile Ala Tyr Tyr Trp Ser Glu Phe Ser Ile Pro Pro His Leu
                155                 160                 165

Ala Glu Glu Val Asp Arg Ala Met Ala Val Glu Arg Val Val Thr
                170                 175                 180

Leu Pro Pro Arg Ala Arg Ala Leu Lys Ser Phe Val Leu Thr Ser
                185                 190                 195

Val Val Ala Phe Pro Ile Asp Pro Arg Met Leu Gln Arg Thr Gln
                200                 205                 210
```

-continued

```
Asp Asn Ser Cys Ser Phe Ala Leu His Ala His Gly Ala Ala Val
                215                 220                 225

Thr Arg Phe Thr Thr Pro Gly Phe Pro Asn Ser Pro Tyr Pro Ala
                230                 235                 240

His Ala Arg Cys Gln Trp Val Leu Arg Gly Asp Ala Asp Ser Val
                245                 250                 255

Leu Ser Leu Thr Phe Arg Ser Phe Asp Val Ala Pro Cys Asp Glu
                260                 265                 270

His Gly Ser Asp Leu Val Thr Val Tyr Asp Ser Leu Ser Pro Met
                275                 280                 285

Glu Pro His Ala Val Val Arg Leu Cys Gly Thr Phe Ser Pro Ser
                290                 295                 300

Tyr Asn Leu Thr Phe Leu Ser Ser Gln Asn Val Phe Leu Val Thr
                305                 310                 315

Leu Ile Thr Asn Thr Gly Arg Arg His Leu Gly Phe Glu Ala Thr
                320                 325                 330

Phe Phe Gln Leu Pro Lys Met Ser Ser Cys Gly Gly Val Leu Ser
                335                 340                 345

Asp Thr Gln Gly Thr Phe Ser Ser Pro Tyr Tyr Pro Gly His Tyr
                350                 355                 360

Pro Pro Asn Ile Asn Cys Thr Trp Asn Ile Lys Val Pro Asn Asn
                365                 370                 375

Arg Asn Val Lys Val Arg Phe Lys Leu Phe Tyr Leu Val Asp Pro
                380                 385                 390

Asn Val Pro Val Gly Ser Cys Thr Lys Asp Tyr Val Glu Ile Asn
                395                 400                 405

Gly Glu Lys Gly Ser Gly Glu Arg Ser Gln Phe Val Val Ser Ser
                410                 415                 420

Asn Ser Ser Lys Ile Thr Val His Phe His Ser Asp His Ser Tyr
                425                 430                 435

Thr Asp Thr Gly Phe Leu Ala Glu Tyr Leu Ser Tyr Asp Ser Asn
                440                 445                 450

Asp Pro Cys Pro Gly Met Phe Met Cys Lys Thr Gly Arg Cys Ile
                455                 460                 465

Arg Lys Glu Leu Arg Cys Asp Gly Trp Ala Asp Cys Pro Asp Tyr
                470                 475                 480

Ser Asp Glu Arg Tyr Cys Arg Cys Asn Ala Thr His Gln Phe Thr
                485                 490                 495

Cys Lys Asn Gln Phe Cys Lys Pro Leu Phe Trp Val Cys Asp Ser
                500                 505                 510

Val Asn Asp Cys Gly Asp Gly Ser Asp Glu Glu Gly Cys Ser Cys
                515                 520                 525

Pro Ala Gly Ser Phe Lys Cys Ser Asn Gly Lys Cys Leu Pro Gln
                530                 535                 540

Ser Gln Lys Cys Asn Gly Lys Asp Asn Cys Gly Asp Gly Ser Asp
                545                 550                 555

Glu Ala Ser Cys Asp Ser Val Asn Val Val Ser Cys Thr Lys Tyr
                560                 565                 570

Thr Tyr Arg Cys Gln Asn Gly Leu Cys Leu Ser Lys Gly Asn Pro
                575                 580                 585

Glu Cys Asp Gly Lys Thr Asp Cys Ser Asp Gly Ser Asp Glu Lys
                590                 595                 600

Asn Cys Asp Cys Gly Leu Arg Ser Phe Thr Lys Gln Ala Arg Val
```

-continued

```
                605                 610                 615

Val Gly Gly Thr Asn Ala Asp Glu Gly Glu Trp Pro Trp Gln Val
                620                 625                 630

Ser Leu His Ala Leu Gly Gln Gly His Leu Cys Gly Ala Ser Leu
                635                 640                 645

Ile Ser Pro Asp Trp Leu Val Ser Ala Ala His Cys Phe Gln Asp
                650                 655                 660

Asp Lys Asn Phe Lys Tyr Ser Asp Tyr Thr Met Trp Thr Ala Phe
                665                 670                 675

Leu Gly Leu Leu Asp Gln Ser Lys Arg Ser Ala Ser Gly Val Gln
                680                 685                 690

Glu Leu Lys Leu Lys Arg Ile Ile Thr His Pro Ser Phe Asn Asp
                695                 700                 705

Phe Thr Phe Asp Tyr Asp Ile Ala Leu Leu Glu Leu Glu Lys Ser
                710                 715                 720

Val Glu Tyr Ser Thr Val Val Arg Pro Ile Cys Leu Pro Asp Ala
                725                 730                 735

Thr His Val Phe Pro Ala Gly Lys Ala Ile Trp Val Thr Gly Trp
                740                 745                 750

Gly His Thr Lys Glu Gly Gly Thr Gly Ala Leu Ile Leu Gln Lys
                755                 760                 765

Gly Glu Ile Arg Val Ile Asn Gln Thr Thr Cys Glu Asp Leu Met
                770                 775                 780

Pro Gln Gln Ile Thr Pro Arg Met Met Cys Val Gly Phe Leu Ser
                785                 790                 795

Gly Gly Val Asp Ser Cys Gln Gly Asp Ser Gly Gly Pro Leu Ser
                800                 805                 810

Ser Ala Glu Lys Asp Gly Arg Met Phe Gln Ala Gly Val Val Ser
                815                 820                 825

Trp Gly Glu Gly Cys Ala Gln Arg Asn Lys Pro Gly Val Tyr Thr
                830                 835                 840

Arg Leu Pro Cys Ser Ser Gly Leu Asp Gln Arg Ala His Trp Gly
                845                 850                 855

Ile Ala Ala Trp Thr Asp Ser Arg Pro Gln Thr Pro Thr Gly Met
                860                 865                 870

Pro Asp Met His Thr Trp Ile Gln Glu Arg Asn Thr Asp Asp Ile
                875                 880                 885

Tyr Ala Val Ala Ser Pro Pro Gln His Asn Pro Asp Cys Glu Leu
                890                 895                 900

His Pro
```

<210> SEQ ID NO 11
<211> LENGTH: 23
<212> TYPE: DNA
<213> ORGANISM: Artificial sequence
<220> FEATURE:
<221> NAME/KEY: n=Inosine
<222> LOCATION: 6, 9, 12, 15, 18
<223> OTHER INFORMATION: Degenerate oligonucleotide primer

<400> SEQUENCE: 11
tgggtngtna cngcngcnca ytg 23

<210> SEQ ID NO 12
<211> LENGTH: 20
<212> TYPE: DNA

```
<213> ORGANISM: Artificial sequence
<220> FEATURE:
<221> NAME/KEY: n=Inosine
<222> LOCATION: 3, 6, 9, 12, 18
<223> OTHER INFORMATION: Degenerate oligonucleotide primer

<400> SEQUENCE: 12

arnggnccnc cnswrtcncc                                                  20


<210> SEQ ID NO 13
<211> LENGTH: 12
<212> TYPE: PRT
<213> ORGANISM: Homo sapiens
<220> FEATURE:
<223> OTHER INFORMATION: Fragment of TADG-15

<400> SEQUENCE: 13

Leu Phe Arg Asp Trp Ile Lys Glu Asn Thr Gly Val
                5                   10


<210> SEQ ID NO 14
<211> LENGTH: 20
<212> TYPE: DNA
<213> ORGANISM: Artificial sequence
<220> FEATURE:
<223> OTHER INFORMATION: TADG-15 forward oligonucleotide primer

<400> SEQUENCE: 14

atgacagagg attcaggtac                                                  20


<210> SEQ ID NO 15
<211> LENGTH: 20
<212> TYPE: DNA
<213> ORGANISM: Artificial sequence
<220> FEATURE:
<223> OTHER INFORMATION: TADG-15 reverse oligonucleotide primer

<400> SEQUENCE: 15

gaaggtgaag tcattgaaga                                                  20


<210> SEQ ID NO 16
<211> LENGTH: 20
<212> TYPE: DNA
<213> ORGANISM: Artificial sequence
<220> FEATURE:
<223> OTHER INFORMATION: (-tubulin forward oligonucleotide primer

<400> SEQUENCE: 16

cgcatcaacg tgtactacaa                                                  20


<210> SEQ ID NO 17
<211> LENGTH: 20
<212> TYPE: DNA
<213> ORGANISM: Artificial sequence
<220> FEATURE:
<223> OTHER INFORMATION: (-tubulin reverse oligonucleotide primer

<400> SEQUENCE: 17

tacgagctgg tggactgaga                                                  20


<210> SEQ ID NO 18
<211> LENGTH: 3147
<212> TYPE: RNA
<213> ORGANISM: Artificial sequence
<220> FEATURE:
<223> OTHER INFORMATION: Antisense of TADG-15
```

-continued

<400> SEQUENCE: 18

```
uuuuuuuuuu uuuuuuuuua aaaagaaaua aauuguuuua cccauuuaca      50
caaauacaca cacugaaguc cacccuggga gcugguaaaa caauuucagu     100
cucagacccg ucuguuuucc aggguccucc gagccugggc uuccucaaga     150
gcguggccca agggccccac agcccagauc cggcagcccc accaccuuca     200
cugaggaggc uccgaagcuc cguucccgcu gcuccuuaca gacaggggag     250
gcagauauac acaaacgcgc cucggcccag cuuggggcug gcgggggagg     300
cugugucuuc aaaccuuugc ccccaguugg gucaguagaa ccaccagugu     350
ccucccccuuc uaccucccag cuccacuuug gaggcugagg aagcgagagg     400
uuuucuaggc agauuuggag cccuggagau ugaguucaca guguauguuc     450
ugggggcgcu ggugcaguca gcgguccagu cuccagccug caggcgugca     500
cacuggggug gacgaugggu ggccccgcag guguacacau uugggugccc     550
ccggccccua uaccccagug uucucuuuga uccagucccg aaacagaggg     600
agccuugugu acacgccugg cuuguuccuc ugagcgcagc cgucucccca     650
gcucaccaca ccggccugga agauccgccc auccgccucc acgcuggaca     700
ggggucccccc ggaaucaccc uggcaggagu ccacgccgcc gcugaggaag     750
cccacgcaca ucaugcgcgg cgugaucugc ugcggcagga gguucucgca     800
gguggucugg uugaugacgc ggaucucacc cuuuugcagg aucagcgcgc     850
cagugccucc auacugggug ugucccccagc ccgugaccca gauggccuug     900
ccggcaggga agacauggga ggcguccggc aggcagaugg gccgcaccau     950
ggagcuguac ucugccgguu ucuccagcuc cagcagcgcg augucauagu    1000
cgaaggugaa gucauugaag aaggggugggg agaugaugcg cuugagccug    1050
cgcuccugca ccccaggggc gcugcgcugg cucuggucgu gcaagcccag    1100
gaaggccguc cacugcgugg ggucugagua ccugaauccu cugucaucga    1150
uguagcagug ugcggcagag accagccagu ugggagagau gagggaagca    1200
ccgcagaugu ggcccuggcc cagagcaugc aggcuuaccu gccagggcca    1250
cucgcccuca uccgcauccg ugcccccaac aacacgagcc ugucucguga    1300
augaccgcag cccacagucg caguccuucu caucugagcc gucgcuacag    1350
uccuccuucc cgucacacuc aggguugccc uugcucaagc agagcccauu    1400
gaggcagcgg uaggugugguu ugguacaagu gacgacguuc accuuggggc    1450
aggaggccuc gucggacccg uccccacagu cguccuuccc auugcacugc    1500
uggcuuuucg agaggcacuu cccauuggaa caccugaagg ucugggccgg    1550
acaacugcac cccugcucgu cgcuguuguc uccgcagucg uucacacugu    1600
cgcagaccca gaagaggggc uugcagaacu uguucuugca cgugaacugg    1650
uggccggcgu cgcaacugca guugagcuca ucgcuguggu cggugcaguc    1700
ggcccagcca ucacagcgca gcuccuuccg gauacaccgc cccgugcggc    1750
acgugaacug ccccgggcau gggucacugg agucguagga gagguauuca    1800
gcuaagaagc cggugucggu guaggacuga ucugagugga agcgaacugu    1850
gaucuuguug cuguugcugg ugacgacgaa cugggaccuc ucuccgcagu    1900
auuucucccc auugaucucc acguaguccu uggggcaggu gcccgcaggc    1950
```

-continued

```
acgccgggcu ccagcaggua gaagaauuug aagcucaccu ucacaugcug        2000

guuguugggc accucaaugu uccaugugca gucaauguug gguggguagu        2050

ggccugggua guaggggcug uugaaugucc ccugggcuuu acguaagcgg        2100

ccuccacagc ugcucauccu aggcagcugg aagaaggugg ccucaaagcc        2150

gggaugccgc cgcucagugu ugguuaucag ugugaugagc aggacguucu        2200

gggaggagug gaaggucagg uuguaggagg gaggguaggu gccacacaac        2250

ugcaccaggg cguggggcuc cauggggcuc aggguguugu acaccgucac        2300

caggucgcug ccgcgcucgu cgcaggacgc aaggucaaag cugcggaagg        2350

ugaggcucag cacugagucg gcguccccc gcagggccca cuggcagcgg         2400

gcaugagcgg gguaggggcu gucagggaag ccgggcgugg ugaagcgcau        2450

cagcuccaca ccgcgggcgu gcaggccaaa gcugcagcug uuguccuggg        2500

uccucuguac uguuuuggag uccgugggga aagccaccac ugaggugacc        2550

acaaaggacu ucagggagcg cgcccgcggg ggcagcauga cuacgcgcuc        2600

cucggccaug acgcgcucgg ccuccuccac caggugcugc gggaugcuga        2650

acucagacca guaguaggcg augacgcugc ccucgcugaa ggccgucaca        2700

gccgacuccu ugugguaggg gcccaggaau gggacuccgc uguacagcag        2750

cuucagcgcg uccuucaccu ugcuggccag gcuuacaaac ucaguggagu        2800

uggaguucuc guaggcaucc acaaaauucu cauuugugau ccucauguag        2850

ccauugaaga ccuucuggac acgcacgucc cgguacugca aaugccacac        2900

caggaagccg auccccagca agaccaagag gaggccgauc agcacggcug        2950

ccagcaccac ccagcgcccc gggccaugcu uuuccaccuu cuugacguug        3000

uugacuggca ggaacuccac gccuuccucc aagccauuca cuuucucgug        3050

ccgggaguug uacuugaguc ccgcgccgaa guccuucggg cccccuccgc        3100

ccuugcgggc ccgaucgcuc cccaugguac cccgaggccg cucuuga           3147


<210> SEQ ID NO 19
<211> LENGTH: 9
<212> TYPE: PRT
<213> ORGANISM: Homo sapiens
<220> FEATURE:
<223> OTHER INFORMATION: Residues 68-76 of the TADG-15 protein

<400> SEQUENCE: 19

Val Leu Leu Gly Ile Gly Phe Leu Val
                5


<210> SEQ ID NO 20
<211> LENGTH: 9
<212> TYPE: PRT
<213> ORGANISM: Homo sapiens
<220> FEATURE:
<223> OTHER INFORMATION: Residues 126-134 of the TADG-15 protein

<400> SEQUENCE: 20

Leu Leu Tyr Ser Gly Val Pro Phe Leu
                5


<210> SEQ ID NO 21
<211> LENGTH: 9
<212> TYPE: PRT
```

<213> ORGANISM: Homo sapiens
<220> FEATURE:
<223> OTHER INFORMATION: Residues 644-652 of the TADG-15 protein

<400> SEQUENCE: 21

Ser Leu Ile Ser Pro Asn Trp Leu Val
5

<210> SEQ ID NO 22
<211> LENGTH: 9
<212> TYPE: PRT
<213> ORGANISM: Homo sapiens
<220> FEATURE:
<223> OTHER INFORMATION: Residues 379-387 of the TADG-15 protein

<400> SEQUENCE: 22

Lys Val Ser Phe Lys Phe Phe Tyr Leu
5

<210> SEQ ID NO 23
<211> LENGTH: 9
<212> TYPE: PRT
<213> ORGANISM: Homo sapiens
<220> FEATURE:
<223> OTHER INFORMATION: Residues 386-394 of the TADG-15 protein

<400> SEQUENCE: 23

Tyr Leu Leu Glu Pro Gly Val Pro Ala
5

<210> SEQ ID NO 24
<211> LENGTH: 9
<212> TYPE: PRT
<213> ORGANISM: Homo sapiens
<220> FEATURE:
<223> OTHER INFORMATION: Residues 257-265 of the TADG-15 protein

<400> SEQUENCE: 24

Ser Leu Thr Phe Arg Ser Phe Asp Leu
5

<210> SEQ ID NO 25
<211> LENGTH: 9
<212> TYPE: PRT
<213> ORGANISM: Homo sapiens
<220> FEATURE:
<223> OTHER INFORMATION: Residues 762-770 of the TADG-15 protein

<400> SEQUENCE: 25

Ile Leu Gln Lys Gly Glu Ile Arg Val
5

<210> SEQ ID NO 26
<211> LENGTH: 9
<212> TYPE: PRT
<213> ORGANISM: Homo sapiens
<220> FEATURE:
<223> OTHER INFORMATION: Residues 841-849 of the TADG-15 protein

<400> SEQUENCE: 26

Arg Leu Pro Leu Phe Arg Asp Trp Ile
5

<210> SEQ ID NO 27
<211> LENGTH: 9
<212> TYPE: PRT
<213> ORGANISM: Homo sapiens

<220> FEATURE:
<223> OTHER INFORMATION: Residues 64-72 of the TADG-15 protein

<400> SEQUENCE: 27

Gly Leu Leu Leu Val Leu Leu Gly Ile
5

<210> SEQ ID NO 28
<211> LENGTH: 9
<212> TYPE: PRT
<213> ORGANISM: Homo sapiens
<220> FEATURE:
<223> OTHER INFORMATION: Residues 57-65 of the TADG-15 protein

<400> SEQUENCE: 28

Val Leu Ala Ala Val Leu Ile Gly Leu
5

<210> SEQ ID NO 29
<211> LENGTH: 9
<212> TYPE: PRT
<213> ORGANISM: Homo sapiens
<220> FEATURE:
<223> OTHER INFORMATION: Residues 67-75 of the TADG-15 protein

<400> SEQUENCE: 29

Leu Val Leu Leu Gly Ile Gly Phe Leu
5

<210> SEQ ID NO 30
<211> LENGTH: 9
<212> TYPE: PRT
<213> ORGANISM: Homo sapiens
<220> FEATURE:
<223> OTHER INFORMATION: Residues 379-387 of the TADG-15 protein

<400> SEQUENCE: 30

Lys Val Ser Phe Lys Phe Phe Tyr Leu
5

<210> SEQ ID NO 31
<211> LENGTH: 9
<212> TYPE: PRT
<213> ORGANISM: Homo sapiens
<220> FEATURE:
<223> OTHER INFORMATION: Residues 126-134 of the TADG-15 protein

<400> SEQUENCE: 31

Leu Leu Tyr Ser Gly Val Pro Phe Leu
5

<210> SEQ ID NO 32
<211> LENGTH: 9
<212> TYPE: PRT
<213> ORGANISM: Homo sapiens
<220> FEATURE:
<223> OTHER INFORMATION: Residues 88-96 of the TADG-15 protein

<400> SEQUENCE: 32

Lys Val Phe Asn Gly Tyr Met Arg Ile
5

<210> SEQ ID NO 33
<211> LENGTH: 9
<212> TYPE: PRT
<213> ORGANISM: Homo sapiens
<220> FEATURE:

<223> OTHER INFORMATION: Residues 670-678 of the TADG-15 protein

<400> SEQUENCE: 33

Thr Gln Trp Thr Ala Phe Leu Gly Leu
5

<210> SEQ ID NO 34
<211> LENGTH: 9
<212> TYPE: PRT
<213> ORGANISM: Homo sapiens
<220> FEATURE:
<223> OTHER INFORMATION: Residues 119-127 of the TADG-15 protein

<400> SEQUENCE: 34

Lys Val Lys Asp Ala Leu Lys Leu Leu
5

<210> SEQ ID NO 35
<211> LENGTH: 9
<212> TYPE: PRT
<213> ORGANISM: Homo sapiens
<220> FEATURE:
<223> OTHER INFORMATION: Residues 60-68 of the TADG-15 protein

<400> SEQUENCE: 35

Ala Val Leu Ile Gly Leu Leu Leu Val
5

<210> SEQ ID NO 36
<211> LENGTH: 9
<212> TYPE: PRT
<213> ORGANISM: Homo sapiens
<220> FEATURE:
<223> OTHER INFORMATION: Residues 62-70 of the TADG-15 protein

<400> SEQUENCE: 36

Leu Ile Gly Leu Leu Leu Val Leu Leu
5

<210> SEQ ID NO 37
<211> LENGTH: 9
<212> TYPE: PRT
<213> ORGANISM: Homo sapiens
<220> FEATURE:
<223> OTHER INFORMATION: Residues 57-65 of the TADG-15 protein

<400> SEQUENCE: 37

Val Leu Ala Ala Val Leu Ile Gly Leu
5

<210> SEQ ID NO 38
<211> LENGTH: 9
<212> TYPE: PRT
<213> ORGANISM: Homo sapiens
<220> FEATURE:
<223> OTHER INFORMATION: Residues 61-69 of the TADG-15 protein

<400> SEQUENCE: 38

Val Leu Ile Gly Leu Leu Leu Val Leu
5

<210> SEQ ID NO 39
<211> LENGTH: 9
<212> TYPE: PRT
<213> ORGANISM: Homo sapiens
<220> FEATURE:
<223> OTHER INFORMATION: Residues 146-154 of the TADG-15 protein

<400> SEQUENCE: 39

Phe Ser Glu Gly Ser Val Ile Ala Tyr
5

<210> SEQ ID NO 40
<211> LENGTH: 9
<212> TYPE: PRT
<213> ORGANISM: Homo sapiens
<220> FEATURE:
<223> OTHER INFORMATION: Residues 658-666 of the TADG-15 protein

<400> SEQUENCE: 40

Tyr Ile Asp Asp Arg Gly Phe Arg Tyr
5

<210> SEQ ID NO 41
<211> LENGTH: 9
<212> TYPE: PRT
<213> ORGANISM: Homo sapiens
<220> FEATURE:
<223> OTHER INFORMATION: Residues 449-457 of the TADG-15 protein

<400> SEQUENCE: 41

Ser Ser Asp Pro Cys Pro Gly Gln Phe
5

<210> SEQ ID NO 42
<211> LENGTH: 9
<212> TYPE: PRT
<213> ORGANISM: Homo sapiens
<220> FEATURE:
<223> OTHER INFORMATION: Residues 401-409 of the TADG-15 protein

<400> SEQUENCE: 42

Tyr Val Glu Ile Asn Gly Glu Lys Tyr
5

<210> SEQ ID NO 43
<211> LENGTH: 9
<212> TYPE: PRT
<213> ORGANISM: Homo sapiens
<220> FEATURE:
<223> OTHER INFORMATION: Residues 387-395 of the TADG-15 protein

<400> SEQUENCE: 43

Leu Leu Glu Pro Gly Val Pro Ala Gly
5

<210> SEQ ID NO 44
<211> LENGTH: 9
<212> TYPE: PRT
<213> ORGANISM: Homo sapiens
<220> FEATURE:
<223> OTHER INFORMATION: Residues 553-561 of the TADG-15 protein

<400> SEQUENCE: 44

Gly Ser Asp Glu Ala Ser Cys Pro Lys
5

<210> SEQ ID NO 45
<211> LENGTH: 9
<212> TYPE: PRT
<213> ORGANISM: Homo sapiens
<220> FEATURE:
<223> OTHER INFORMATION: Residues 97-105 of the TADG-15 protein

<400> SEQUENCE: 45

Thr Asn Glu Asn Phe Val Asp Ala Tyr
5

<210> SEQ ID NO 46
<211> LENGTH: 9
<212> TYPE: PRT
<213> ORGANISM: Homo sapiens
<220> FEATURE:
<223> OTHER INFORMATION: Residues 110-118 of the TADG-15 protein

<400> SEQUENCE: 46

Ser Thr Glu Phe Val Ser Leu Ala Ser
5

<210> SEQ ID NO 47
<211> LENGTH: 9
<212> TYPE: PRT
<213> ORGANISM: Homo sapiens
<220> FEATURE:
<223> OTHER INFORMATION: Residues 811-819 of the TADG-15 protein

<400> SEQUENCE: 47

Ser Val Glu Ala Asp Gly Arg Ile Phe
5

<210> SEQ ID NO 48
<211> LENGTH: 9
<212> TYPE: PRT
<213> ORGANISM: Homo sapiens
<220> FEATURE:
<223> OTHER INFORMATION: Residues 666-674 of the TADG-15 protein

<400> SEQUENCE: 48

Tyr Ser Asp Pro Thr Gln Trp Thr Ala
5

<210> SEQ ID NO 49
<211> LENGTH: 9
<212> TYPE: PRT
<213> ORGANISM: Homo sapiens
<220> FEATURE:
<223> OTHER INFORMATION: Residues 709-717 of the TADG-15 protein

<400> SEQUENCE: 49

Asp Tyr Asp Ile Ala Leu Leu Glu Leu
5

<210> SEQ ID NO 50
<211> LENGTH: 9
<212> TYPE: PRT
<213> ORGANISM: Homo sapiens
<220> FEATURE:
<223> OTHER INFORMATION: Residues 408-416 of the TADG-15 protein

<400> SEQUENCE: 50

Lys Tyr Cys Gly Glu Arg Ser Gln Phe
5

<210> SEQ ID NO 51
<211> LENGTH: 9
<212> TYPE: PRT
<213> ORGANISM: Homo sapiens
<220> FEATURE:
<223> OTHER INFORMATION: Residues 754-762 of the TADG-15 protein

<400> SEQUENCE: 51

```
Gln Tyr Gly Gly Thr Gly Ala Leu Ile
                 5


<210> SEQ ID NO 52
<211> LENGTH: 9
<212> TYPE: PRT
<213> ORGANISM: Homo sapiens
<220> FEATURE:
<223> OTHER INFORMATION: Residues 153-161 of the TADG-15 protein

<400> SEQUENCE: 52

Ala Tyr Tyr Trp Ser Glu Phe Ser Ile
                 5


<210> SEQ ID NO 53
<211> LENGTH: 9
<212> TYPE: PRT
<213> ORGANISM: Homo sapiens
<220> FEATURE:
<223> OTHER INFORMATION: Residues 722-730 of the TADG-15 protein

<400> SEQUENCE: 53

Glu Tyr Ser Ser Met Val Arg Pro Ile
                 5


<210> SEQ ID NO 54
<211> LENGTH: 9
<212> TYPE: PRT
<213> ORGANISM: Homo sapiens
<220> FEATURE:
<223> OTHER INFORMATION: Residues 326-334 of the TADG-15 protein

<400> SEQUENCE: 54

Gly Phe Glu Ala Thr Phe Phe Gln Leu
                 5


<210> SEQ ID NO 55
<211> LENGTH: 9
<212> TYPE: PRT
<213> ORGANISM: Homo sapiens
<220> FEATURE:
<223> OTHER INFORMATION: Residues 304-312 of the TADG-15 protein

<400> SEQUENCE: 55

Thr Phe His Ser Ser Gln Asn Val Leu
                 5


<210> SEQ ID NO 56
<211> LENGTH: 9
<212> TYPE: PRT
<213> ORGANISM: Homo sapiens
<220> FEATURE:
<223> OTHER INFORMATION: Residues 707-715 of the TADG-15 protein

<400> SEQUENCE: 56

Thr Phe Asp Tyr Asp Ile Ala Leu Leu
                 5


<210> SEQ ID NO 57
<211> LENGTH: 9
<212> TYPE: PRT
<213> ORGANISM: Homo sapiens
<220> FEATURE:
<223> OTHER INFORMATION: Residues 21-29 of the TADG-15 protein

<400> SEQUENCE: 57
```

Lys Tyr Asn Ser Arg His Glu Lys Val
5

<210> SEQ ID NO 58
<211> LENGTH: 9
<212> TYPE: PRT
<213> ORGANISM: Homo sapiens
<220> FEATURE:
<223> OTHER INFORMATION: Residues 665-673 of the TADG-15 protein

<400> SEQUENCE: 58

Arg Tyr Ser Asp Pro Thr Gln Trp Thr
5

<210> SEQ ID NO 59
<211> LENGTH: 9
<212> TYPE: PRT
<213> ORGANISM: Homo sapiens
<220> FEATURE:
<223> OTHER INFORMATION: Residues 686-694 of the TADG-15 protein

<400> SEQUENCE: 59

Ala Pro Gly Val Gln Glu Arg Arg Leu
5

<210> SEQ ID NO 60
<211> LENGTH: 9
<212> TYPE: PRT
<213> ORGANISM: Homo sapiens
<220> FEATURE:
<223> OTHER INFORMATION: Residues 12-20 of the TADG-15 protein

<400> SEQUENCE: 60

Gly Pro Lys Asp Phe Gly Ala Gly Leu
5

<210> SEQ ID NO 61
<211> LENGTH: 9
<212> TYPE: PRT
<213> ORGANISM: Homo sapiens
<220> FEATURE:
<223> OTHER INFORMATION: Residues 668-676 of the TADG-15 protein

<400> SEQUENCE: 61

Asp Pro Thr Gln Trp Thr Ala Phe Leu
5

<210> SEQ ID NO 62
<211> LENGTH: 9
<212> TYPE: PRT
<213> ORGANISM: Homo sapiens
<220> FEATURE:
<223> OTHER INFORMATION: Residues 461-469 of the TADG-15 protein

<400> SEQUENCE: 62

Thr Gly Arg Cys Ile Arg Lys Glu Leu
5

<210> SEQ ID NO 63
<211> LENGTH: 9
<212> TYPE: PRT
<213> ORGANISM: Homo sapiens
<220> FEATURE:
<223> OTHER INFORMATION: Residues 59-67 of the TADG-15 protein

<400> SEQUENCE: 63

Ala Ala Val Leu Ile Gly Leu Leu Leu

5

<210> SEQ ID NO 64
<211> LENGTH: 9
<212> TYPE: PRT
<213> ORGANISM: Homo sapiens
<220> FEATURE:
<223> OTHER INFORMATION: Residues 379-387 of the TADG-15 protein

<400> SEQUENCE: 64

Lys Val Ser Phe Lys Phe Phe Tyr Leu
5

<210> SEQ ID NO 65
<211> LENGTH: 9
<212> TYPE: PRT
<213> ORGANISM: Homo sapiens
<220> FEATURE:
<223> OTHER INFORMATION: Residues 119-127 of the TADG-15 protein

<400> SEQUENCE: 65

Lys Val Lys Asp Ala Leu Lys Leu Leu
5

<210> SEQ ID NO 66
<211> LENGTH: 9
<212> TYPE: PRT
<213> ORGANISM: Homo sapiens
<220> FEATURE:
<223> OTHER INFORMATION: Residues 780-788 of the TADG-15 protein

<400> SEQUENCE: 66

Leu Pro Gln Gln Ile Thr Pro Arg Met
5

<210> SEQ ID NO 67
<211> LENGTH: 9
<212> TYPE: PRT
<213> ORGANISM: Homo sapiens
<220> FEATURE:
<223> OTHER INFORMATION: Residues 67-75 of the TADG-15 protein

<400> SEQUENCE: 67

Leu Val Leu Leu Gly Ile Gly Phe Leu
5

<210> SEQ ID NO 68
<211> LENGTH: 9
<212> TYPE: PRT
<213> ORGANISM: Homo sapiens
<220> FEATURE:
<223> OTHER INFORMATION: Residues 283-291 of the TADG-15 protein

<400> SEQUENCE: 68

Ser Pro Met Glu Pro His Ala Leu Val
5

<210> SEQ ID NO 69
<211> LENGTH: 9
<212> TYPE: PRT
<213> ORGANISM: Homo sapiens
<220> FEATURE:
<223> OTHER INFORMATION: Residues 12-20 of the TADG-15 protein

<400> SEQUENCE: 69

Gly Pro Lys Asp Phe Gly Ala Gly Leu
5

<210> SEQ ID NO 70
<211> LENGTH: 9
<212> TYPE: PRT
<213> ORGANISM: Homo sapiens
<220> FEATURE:
<223> OTHER INFORMATION: Residues 257-265 of the TADG-15 protein

<400> SEQUENCE: 70

Ser Leu Thr Phe Arg Ser Phe Asp Leu
5

<210> SEQ ID NO 71
<211> LENGTH: 9
<212> TYPE: PRT
<213> ORGANISM: Homo sapiens
<220> FEATURE:
<223> OTHER INFORMATION: Residues 180-188 of the TADG-15 protein

<400> SEQUENCE: 71

Met Leu Pro Pro Arg Ala Arg Ser Leu
5

<210> SEQ ID NO 72
<211> LENGTH: 9
<212> TYPE: PRT
<213> ORGANISM: Homo sapiens
<220> FEATURE:
<223> OTHER INFORMATION: Residues 217-225 of the TADG-15 protein

<400> SEQUENCE: 72

Gly Leu His Ala Arg Gly Val Glu Leu
5

<210> SEQ ID NO 73
<211> LENGTH: 9
<212> TYPE: PRT
<213> ORGANISM: Homo sapiens
<220> FEATURE:
<223> OTHER INFORMATION: Residues 173-181 of the TADG-15 protein

<400> SEQUENCE: 73

Met Ala Glu Glu Arg Val Val Met Leu
5

<210> SEQ ID NO 74
<211> LENGTH: 9
<212> TYPE: PRT
<213> ORGANISM: Homo sapiens
<220> FEATURE:
<223> OTHER INFORMATION: Residues 267-275 of the TADG-15 protein

<400> SEQUENCE: 74

Ser Cys Asp Glu Arg Gly Ser Asp Leu
5

<210> SEQ ID NO 75
<211> LENGTH: 9
<212> TYPE: PRT
<213> ORGANISM: Homo sapiens
<220> FEATURE:
<223> OTHER INFORMATION: Residues 567-575 of the TADG-15 protein

<400> SEQUENCE: 75

Cys Thr Lys His Thr Tyr Arg Cys Leu
5

<210> SEQ ID NO 76
<211> LENGTH: 9
<212> TYPE: PRT
<213> ORGANISM: Homo sapiens
<220> FEATURE:
<223> OTHER INFORMATION: Residues 724-732 of the TADG-15 protein

<400> SEQUENCE: 76

Ser Ser Met Val Arg Pro Ile Cys Leu
5

<210> SEQ ID NO 77
<211> LENGTH: 9
<212> TYPE: PRT
<213> ORGANISM: Homo sapiens
<220> FEATURE:
<223> OTHER INFORMATION: Residues 409-417 of the TADG-15 protein

<400> SEQUENCE: 77

Tyr Cys Gly Glu Arg Ser Gln Phe Val
5

<210> SEQ ID NO 78
<211> LENGTH: 9
<212> TYPE: PRT
<213> ORGANISM: Homo sapiens
<220> FEATURE:
<223> OTHER INFORMATION: Residues 495-503 of the TADG-15 protein

<400> SEQUENCE: 78

Thr Cys Lys Asn Lys Phe Cys Lys Pro
5

<210> SEQ ID NO 79
<211> LENGTH: 9
<212> TYPE: PRT
<213> ORGANISM: Homo sapiens
<220> FEATURE:
<223> OTHER INFORMATION: Residues 427-435 of the TADG-15 protein

<400> SEQUENCE: 79

Val Arg Phe His Ser Asp Gln Ser Tyr
5

<210> SEQ ID NO 80
<211> LENGTH: 9
<212> TYPE: PRT
<213> ORGANISM: Homo sapiens
<220> FEATURE:
<223> OTHER INFORMATION: Residues 695-703 of the TADG-15 protein

<400> SEQUENCE: 80

Lys Arg Ile Ile Ser His Pro Phe Phe
5

<210> SEQ ID NO 81
<211> LENGTH: 9
<212> TYPE: PRT
<213> ORGANISM: Homo sapiens
<220> FEATURE:
<223> OTHER INFORMATION: Residues 664-672 of the TADG-15 protein

<400> SEQUENCE: 81

Phe Arg Tyr Ser Asp Pro Thr Gln Trp
5

<210> SEQ ID NO 82
<211> LENGTH: 9
<212> TYPE: PRT
<213> ORGANISM: Homo sapiens
<220> FEATURE:
<223> OTHER INFORMATION: Residues 220-228 of the TADG-15 protein

<400> SEQUENCE: 82

Ala Arg Gly Val Glu Leu Met Arg Phe
5

<210> SEQ ID NO 83
<211> LENGTH: 9
<212> TYPE: PRT
<213> ORGANISM: Homo sapiens
<220> FEATURE:
<223> OTHER INFORMATION: Residues 492-500 of the TADG-15 protein

<400> SEQUENCE: 83

His Gln Phe Thr Cys Lys Asn Lys Phe
5

<210> SEQ ID NO 84
<211> LENGTH: 9
<212> TYPE: PRT
<213> ORGANISM: Homo sapiens
<220> FEATURE:
<223> OTHER INFORMATION: Residues 53-61 of the TADG-15 protein

<400> SEQUENCE: 84

Gly Arg Trp Val Val Leu Ala Ala Val
5

<210> SEQ ID NO 85
<211> LENGTH: 9
<212> TYPE: PRT
<213> ORGANISM: Homo sapiens
<220> FEATURE:
<223> OTHER INFORMATION: Residues 248-256 of the TADG-15 protein

<400> SEQUENCE: 85

Leu Arg Gly Asp Ala Asp Ser Val Leu
5

<210> SEQ ID NO 86
<211> LENGTH: 9
<212> TYPE: PRT
<213> ORGANISM: Homo sapiens
<220> FEATURE:
<223> OTHER INFORMATION: Residues 572-580 of the TADG-15 protein

<400> SEQUENCE: 86

Tyr Arg Cys Leu Asn Gly Leu Cys Leu
5

<210> SEQ ID NO 87
<211> LENGTH: 9
<212> TYPE: PRT
<213> ORGANISM: Homo sapiens
<220> FEATURE:
<223> OTHER INFORMATION: Residues 692-700 of the TADG-15 protein

<400> SEQUENCE: 87

Arg Arg Leu Lys Arg Ile Ile Ser His
5

<210> SEQ ID NO 88

<211> LENGTH: 9
<212> TYPE: PRT
<213> ORGANISM: Homo sapiens
<220> FEATURE:
<223> OTHER INFORMATION: Residues 24-32 of the TADG-15 protein

<400> SEQUENCE: 88

Ser Arg His Glu Lys Val Asn Gly Leu
5

<210> SEQ ID NO 89
<211> LENGTH: 9
<212> TYPE: PRT
<213> ORGANISM: Homo sapiens
<220> FEATURE:
<223> OTHER INFORMATION: Residues 147-155 of the TADG-15 protein

<400> SEQUENCE: 89

Ser Glu Gly Ser Val Ile Ala Tyr Tyr
5

<210> SEQ ID NO 90
<211> LENGTH: 9
<212> TYPE: PRT
<213> ORGANISM: Homo sapiens
<220> FEATURE:
<223> OTHER INFORMATION: Residues 715-723 of the TADG-15 protein

<400> SEQUENCE: 90

Leu Glu Leu Glu Lys Pro Ala Glu Tyr
5

<210> SEQ ID NO 91
<211> LENGTH: 9
<212> TYPE: PRT
<213> ORGANISM: Homo sapiens
<220> FEATURE:
<223> OTHER INFORMATION: Residues 105-113 of the TADG-15 protein

<400> SEQUENCE: 91

Tyr Glu Asn Ser Asn Ser Thr Glu Phe
5

<210> SEQ ID NO 92
<211> LENGTH: 9
<212> TYPE: PRT
<213> ORGANISM: Homo sapiens
<220> FEATURE:
<223> OTHER INFORMATION: Residues 14-22 of the TADG-15 protein

<400> SEQUENCE: 92

Lys Asp Phe Gly Ala Gly Leu Lys Tyr
5

<210> SEQ ID NO 93
<211> LENGTH: 9
<212> TYPE: PRT
<213> ORGANISM: Homo sapiens
<220> FEATURE:
<223> OTHER INFORMATION: Residues 129-137 of the TADG-15 protein

<400> SEQUENCE: 93

Ser Gly Val Pro Phe Leu Gly Pro Tyr
5

<210> SEQ ID NO 94
<211> LENGTH: 9

-continued

```
<212> TYPE: PRT
<213> ORGANISM: Homo sapiens
<220> FEATURE:
<223> OTHER INFORMATION: Residues 436-444 of the TADG-15 protein

<400> SEQUENCE: 94

Thr Asp Thr Gly Phe Leu Ala Glu Tyr
                1               5


<210> SEQ ID NO 95
<211> LENGTH: 9
<212> TYPE: PRT
<213> ORGANISM: Homo sapiens
<220> FEATURE:
<223> OTHER INFORMATION: Residues 766-774 of the TADG-15 protein

<400> SEQUENCE: 95

Gly Glu Ile Arg Val Ile Asn Gln Thr
                5


<210> SEQ ID NO 96
<211> LENGTH: 9
<212> TYPE: PRT
<213> ORGANISM: Homo sapiens
<220> FEATURE:
<223> OTHER INFORMATION: Residues 402-410 of the TADG-15 protein

<400> SEQUENCE: 96

Val Glu Ile Asn Gly Glu Lys Tyr Cys
                5


<210> SEQ ID NO 97
<211> LENGTH: 9
<212> TYPE: PRT
<213> ORGANISM: Homo sapiens
<220> FEATURE:
<223> OTHER INFORMATION: Residues 482-490 of the TADG-15 protein

<400> SEQUENCE: 97

Asp Glu Leu Asn Cys Ser Cys Asp Ala
                5


<210> SEQ ID NO 98
<211> LENGTH: 9
<212> TYPE: PRT
<213> ORGANISM: Homo sapiens
<220> FEATURE:
<223> OTHER INFORMATION: Residues 82-90 of the TADG-15 protein

<400> SEQUENCE: 98

Arg Asp Val Arg Val Gln Lys Val Phe
                5
```